US011208698B2

(12) United States Patent
Guilford et al.

(10) Patent No.: US 11,208,698 B2
(45) Date of Patent: *Dec. 28, 2021

(54) METHODS FOR DETECTION OF MARKERS BLADDER CANCER AND INFLAMMATORY CONDITIONS OF THE BLADDER AND TREATMENT THEREOF

(71) Applicant: Pacific Edge Limited, Dunedin (NZ)

(72) Inventors: Parry John Guilford, Dunedin (NZ); Mark Dalphin, Dunedin (NZ); Laimonis Kavalieris, Dunedin (NZ); Paul O'Sullivan, Dunedin (NZ)

(73) Assignee: PACIFICEDGE LIMITED, Dunedin (NZ)

( * ) Notice: Subject to any disclaimer, the term of this patent is extended or adjusted under 35 U.S.C. 154(b) by 52 days.

This patent is subject to a terminal disclaimer.

(21) Appl. No.: 15/988,491

(22) Filed: May 24, 2018

(65) Prior Publication Data

US 2018/0298452 A1 Oct. 18, 2018

Related U.S. Application Data

(62) Division of application No. 13/884,681, filed as application No. PCT/NZ2011/000238 on Nov. 11, 2011, now Pat. No. 9,982,305.

(30) Foreign Application Priority Data

Nov. 12, 2010 (NZ) ........................ 589251

(51) Int. Cl.
*C12Q 1/6886* (2018.01)
*G01N 33/566* (2006.01)
*G01N 33/574* (2006.01)

(52) U.S. Cl.
CPC ......... *C12Q 1/6886* (2013.01); *G01N 33/566* (2013.01); *G01N 33/57407* (2013.01); *C12Q 2600/158* (2013.01); *G01N 2333/7155* (2013.01)

(58) Field of Classification Search
None
See application file for complete search history.

(56) References Cited

U.S. PATENT DOCUMENTS

| 6,355,170 B1 | 1/2002 | Orntoft |
| 6,582,908 B2 | 6/2003 | Fodor |
| 7,090,983 B1 * | 8/2006 | Muramatsu ........ G01N 33/574 435/4 |
| 9,702,009 B2 | 7/2017 | Guilford |
| 10,131,955 B2 * | 11/2018 | Darling ............ G01N 33/57484 |
| 2006/0227663 A1 | 10/2006 | Clark |
| 2009/0098553 A1 | 4/2009 | Guilford |
| 2009/0269744 A1 | 10/2009 | Krause |
| 2010/0130527 A1 | 5/2010 | Lehrer |

FOREIGN PATENT DOCUMENTS

| EP | 1930445 | 6/2008 |
| WO | WO 2003/003906 | 1/2003 |
| WO | WO 2005/0103702 | 4/2004 |
| WO | WO 2006/012522 A1 * | 2/2006 |
| WO | WO 2010/078403 | 7/2010 |

OTHER PUBLICATIONS

Holyoake et al Clinical Cancer Research. 2008. 14(3): 742-749 and Supplementary Figure 1 and Table 1 (Year: 2008).*
Sigma-Aldrich. qPCR Technical Guide. 2008 Available via url: <gene-quantification.com/SIAL-qPCR-Technical-Guide.pdf> (Year: 2008).*
Gen Bank Accession No. NM_001168298.1, Nov. 28, 2009.*
O'Sullivan et al BJU International. Mar. 2009. 103:45, abstract #143 (Year: 2009).*
Holyoake, et al (2008) Clincal Cancer Reserch, 14(3):742-749.
Andrew et al, (2009) Human Genetics 125(5-6):527-539.
Kawanishi et al. Clinical Cancer Research (2008) 14(9): 2579-2587.
International Search Report for PCT/NZ2011/000238; dated Jun. 14, 2012.
International Search Report for PCT/NZ2011/000238; dated Oct. 4, 2012;.
Australian Patent Office, P.O. Box 200, Woden Act 2606, Australia.

* cited by examiner

*Primary Examiner* — Carla J Myers
(74) *Attorney, Agent, or Firm* — D. Benjamin Borson; Borson Law Group PC

(57) ABSTRACT

Embodiments of this invention include methods for detection of markers of bladder cancer and inflammatory conditions of the bladder. Particularly, methods include detection of expression of certain genetic markers for bladder cancer and markers for detection of inflammatory conditions of the bladder. These methods provide improved detection of the markers, and provide better detection of bladder cancer and inflammatory conditions of the bladder.

19 Claims, 101 Drawing Sheets

Specification includes a Sequence Listing.

```
LOCUS       NM_001557               2880 bp    mRNA
DEFINITION  Homo sapiens chemokine (C-X-C motif) receptor 2 (CXCR2), transcript variant
            1, mRNA.
ACCESSION   NM_001557
VERSION     NM_001557.3  GI:269973857

Protein sequence: "MEDFNMESDSFEDFWKGEDLSNYSYSSTLPPFLLDAAPCEPESL
EINKYFVVIIYALVFLLSLLGNSLVMLVILYSRVGRSVTDVYLLNLALADLLFALTLP
IWAASKVNGWIFGTFLCKVVSLLKEVNFYSGILLLACISVDRYLAIVHATRTLTQKRY
LVKFICLSIWGLSLLLALPVLLFRRTVYSSNVSPACYEDMGNNTANWRMLLRILPQSF
GFIVPLLIMLFCYGFTIRTLFKAHMGQKHRAMRVIFAVVLIFLLCWLPYNLVLLADTL
MRTQVIQETCERRNHIDRALDATEILGILHSCLNPLIYAFIGQKFRHGLLKILAIHGL
ISKDSLPKDSRPSFVGSSSGHTSTTL"

ORIGIN
    1 aggttcaaaa cattcagaga cagaaggtgg atagacaaat ctccaccttc agactggtag
   61 gctcctccag aagccatcag acaggaagat gtgaaaatcc ccagcactca tcccagaatc
  121 actaagtggc acctgtcctg ggccaaagtc ccaggacaga cctcattgtt cctctgtggg
  181 aatacctccc caggagggca tcctggattt ccccccttgca accaggtca gaagtttcat
  241 cgtcaaggtt gtttcatctt tctaacagct ctgactacca cccaaccttg
  301 aggcacagtg aagacatcgg tggccactcc aataacagca ggtcacagct gctcttctgg
  361 aggtgtccta caggtgaaaa gcccagcgac ccagtcagga tttaagttta cctcaaaaat
  421 ggaagatttt aacatggaga gtgacagctt tgaagatttc tggaaaggtg aagatcttag
  481 taattacagt tacagctcta ccctgcccc ttttctacta gatgccgccc catgtgaacc
  541 agaatccctg gaaatcaaca agtattttgt ggtcattatc tatgccctgg tattcctgct
```

Figure 1

```
 601 gagcctgctg ggaaactccc tcgtgatgct ggtcatctta tacagcaggg tcggccgctc
 661 cgtcactgat gtctacctgc tgaacctagc cttggccgac ctactctttg ccctgacctt
 721 gcccatctgg gccgcctcca agtgaatgg ctggatttt gcacattcc tgtgcaaggt
 781 gtctccactc ctgaaggaag tcaacttcta tagtgcatc ctgctactgg cctgcatcag
 841 tgtggaccgt tacctggcca ttgtccatgc cacacgcaca ctgaccccaga agcgctactt
 901 ggtcaaattc atatgtctca gcatctgggg tctgtcctg ctcctgccc tgcctgtctt
 961 actttccga aggaccgtct actcatccaa tgttagccca gcctgctatg aggacatggg
1021 caacaataca gcaaactggc ggatgctgtt acggatcctg cccagtcct ttgcttcat
1081 cgtgccactg ctgatcatgc tgttctgcta cggattcacc ctgcgtacgc tgtttaaggc
1141 ccacatgggg cagaagcacc gggccatgcg ggtcatcttt gctgtcgtcc tcatcttcct
1201 gctctgctgg ctgccctaca acctgtcct gctgcagac accctcatga ggaccaggt
1261 gatccaggag acctgtgagc gccgcaatca catcgaccgg gtctgtggatg ccaccgagat
1321 tctggcatc cttcacagct gcctcaaccc cctcatctac gccttcattg gccagaagtt
1381 tcgccatgga ctcctcaaga ttctagctat acatggcttg atcagcaagg actccctgcc
1441 caagacagc aggccttcct ttgttggctc ttcttcaggg cacacttcca ctactctcta
1501 agacctcctg cctaagtgca gcccgtggg gttcctccct tctcttcaca gtcacattcc
1561 aagcctcatg tccactggtt cttcttggtc tcagtgtcaa tgcagcccc attgtggtca
1621 caggaagtag aggaggccac gttcttacta gtttccctg catggttag aaagcttgcc
1681 ctgtgcctc accccttgcc ataattacta tgtcatttgc tggagctctg cccatcctgc
1741 ccctgagccc atggcactct atgttctaag aagtgaaaat ctacactcca gtgagacagc
1801 tctgcatact cattaggatg gctagtatca aagaaagaa aatcaggctg gccaacgggg
1861 tgaaaccctg tctctactaa aaatacaaaa aaaaaaaaa attagccggg cgtggtggtg
1921 agtgcctgta atcacagcta cttgggaggc tgagatggga gaatcacttg aacccggag
1981 gcagaggttg cagtgagccg agattgtgcc cctgcactcc agcctgagcg acagtgagac
2041 tctgtctcag tccatgaaga tgtagaggag aaactggaac tctcgagcgt tgctggggg
2101 gattgtaaaa tggtgtgacc actgcagaag acagtatggc agctttcctc aaaacttcag
2161 acatagaatt aacacatgat cctgcaattc cacttatagg aattgaccca caagaaatga
2221 aagcagggac ttgaacccat atttgtacac caatattcat agcagcttat tcacaagacc
2281 caaaaggcag aagcaaccca aatgttcatc aatgaatgaa tgaatgcta agcaaaatgt
2341 gatatgtacc taacgaagta tccttcagcc tgaaagagga atgaagtact catacatgtt
```

Figure 1 (cont)

```
2401  acaacacgga cgaaccttga aaactttatg ctaagtgaaa taagccagac atcaacagat
2461  aaatagttta tgattccacc tacatgaggt actgagagtg aacaaattta cagagacaga
2521  aagcagaaca gtgattacca gggactgagg ggaggggagc atgggaagtg acggtttaat
2581  gggcacaggg tttatgttta ggatgttgaa aaagttctgc agataaaacag tagtgatagt
2641  tgtaccgcaa tgtgacttaa tgccactaaa ttgacactta aaaatggttt aaatggtcaa
2701  ttttgttatg tatattttat atcaattttaa aaaaaaacct gagccccaaa aggtatttta
2761  atcaccaagg ctgattaaac caaggctaga accacctgcc tatatttttt gttaaatgat
2821  ttcattcaat atcttttttt taataaaacca tttttacttg ggtgtttata aaaaaaaaaa
```

Figure 1 (cont)

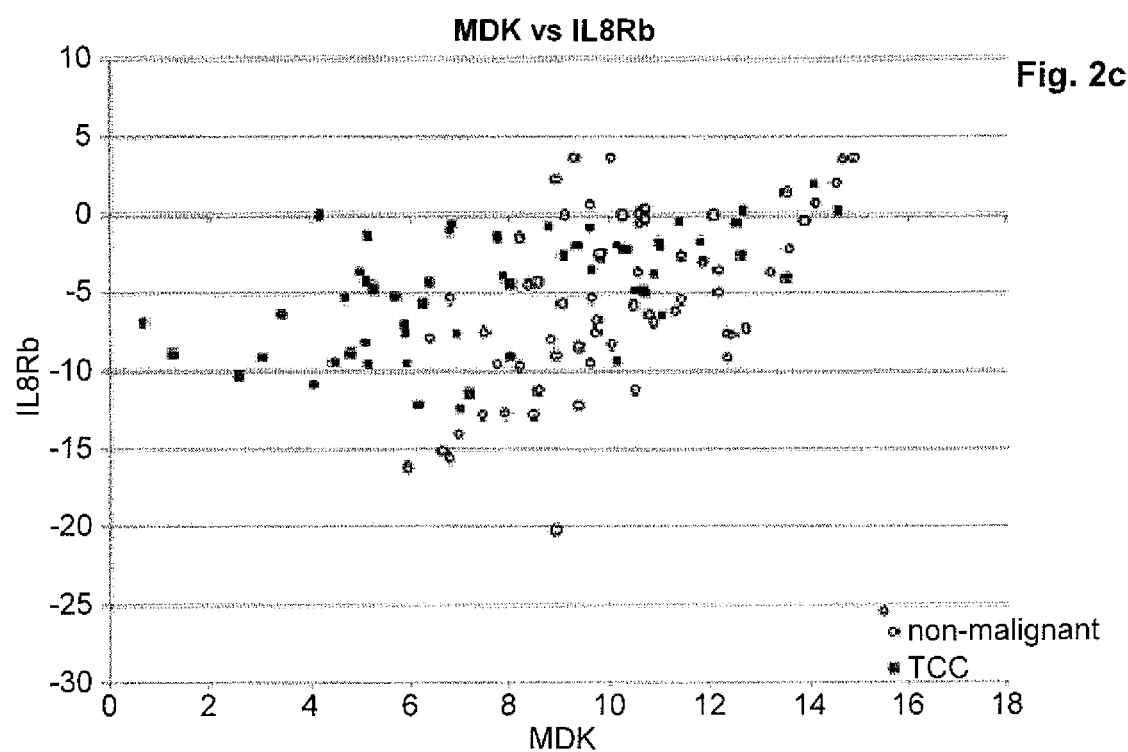

| Gene name/symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ras homolog gene family, member B (RHOB), mRNA | NP_004031.1 | NM_004040.2 | mwghuman3 0K#A:08114 | -2.684592 | 2.13794E-10 | 2.25758E-09 | -10.53678 | 38 | 8789.5 | 4176 | 23 |
| hypothetical protein FLJ21511 (FLJ21511), mRNA | NP_079363.1 | NM_025087.1 | mwghuman3 0K#A:00410 | -2.080908 | 2.54894E-11 | 3.22908E-08 | -6.925773 | 68 | 14455 | 9272.5 | 0 |
| paired box gene 8 (PAX8), transcript variant PAX8A, mRNA | NP_003457.1 | NM_003466.3 | mwghuman3 0K#B:3648 | -1.961896 | 4.71674E-11 | 4.07014E-08 | -6.806281 | 82 | 19419 | 12999.5 | 0 |
| UPF3 regulator of nonsense transcripts homolog A (yeast) (UPF3A), transcript variant 1, mRNA | NP_075387.1 | NM_023011.2 | mwghuman3 0K#A:06295 | -3.84007 | 1.03703E-13 | 3.34027E-08 | -7.811653 | 96.5 | 5663.5 | 1825 | 0 |
| leukotriene B4 12-hydroxydehydrogenase (LTB4DH), mRNA | NP_036344.1 | NM_012212.2 | mwghuman3 0K#B:8686 | -5.034613 | 3.08873E-10 | 1.41836E-07 | -6.436167 | 122.5 | 11340.5 | 3138 | 0 |

Figure 6

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| RAB11 family interacting protein 2 (class I) (RAB11FIP2), mRNA | NP_055719.1 | NM_014904.1 | mwghuman3 0K#A:10479 | -1.993629 | 4.57925E-09 | 5.83951E-08 | -7.711624 | 156 | 19636.5 | 12951 | 0 |
| TSC22 domain family, member 1 (TSC22D1), transcript variant 2, mRNA | NP_006013.1 | NM_006022.2 | mwghuman3 0K#A:00577 | -2.133065 | 1.12033E-07 | 1.8543E-07 | -7.698568 | 156.5 | 8415 | 6130 | 1 |
| sulfite oxidase (SUOX), nuclear gene encoding mitochondrial protein, transcript variant 1, mRNA | NP_000447.2 | NM_000456.2 | mwghuman3 0K#A:05512 | -1.622803 | 4.52404E-10 | 5.29156E-09 | -6.728892 | 223 | 11312.5 | 8789.5 | 0 |
| tetratricopeptide repeat domain 21A (TTC21A), mRNA | NP_665698.1 | NM_145755.1 | mwghuman3 0K#B:6976 | -2.976809 | 2.11314E-07 | 4.28806E-07 | -6.286432 | 225 | 8375.5 | 3870.5 | 1 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| RAS p21 protein activator (GTPase activating protein) 1 (RASA1), transcript variant 2, mRNA | NP_072179.1 | NM_022650.1 | mwghuman3 0K#A:08292 | -1.947454 | 3.74564E-09 | 2.68048E-06 | -5.99299 | 235 | 6895.5 | 5277.5 | 7 |
| ensembl genscan prediction | | AC024384.3.1 079975.119435 .1 | mwghuman3 0K#C:6641 | -2.471322 | 4.47058E-08 | 1.54585E-06 | -6.085076 | 255.5 | 3327.5 | 1537 | |
| ensembl genscan prediction | | AL031669.28. 1.94224.1 | mwghuman3 0K#C:0930 | -1.774123 | 6.77812E-09 | 1.13272E-06 | -5.56116 | 288.5 | 4367 | 3218 | |
| geminin, DNA replication inhibitor (GMNN), mRNA | NP_056979.1 | NM_015895.3 | mwghuman3 0K#A:03435 | -2.046753 | 1.94846E-07 | 4.07898E-06 | -5.99032 | 311 | 11844 | 8413.75 | 2 |
| fatty acid binding protein 1, liver (FABP1), mRNA | NP_001434.1 | NM_001443.1 | mwghuman3 0K#A:09506 | -1.985247 | 2.20148E-06 | 6.83453E-07 | -6.750782 | 312.5 | 25595 | 19500.75 | 0 |
| v-jun sarcoma virus 17 oncogene homolog (avian) (JUN), mRNA | NP_002219.1 | NM_002228.3 | mwghuman3 0K#A:04848 | -3.222311 | 6.2171E-07 | 4.59274E-06 | -6.383849 | 318.5 | 12139 | 5321.5 | 11 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| transmembrane and coiled-coil domains 4 (TMCO4), mRNA | NP_859070.2 | NM_181719.2 | mwghuman30K#B:3094 | -1.799143 | 8.41415E-09 | 3.21175E-06 | -5.702577 | 322.5 | 4584.5 | 3158 | 5 |
| ensembl genscan prediction | | AP002080.2.37398.74587.1 | mwghuman30K#C:4035 | -1.860121 | 5.75299E-08 | 1.01121E-07 | -7.300326 | 332.5 | 4972.5 | 2643 | |
| synaptotagmin-like 2 (SYTL2), transcript variant b, mRNA | NP_115755.2 | NM_032379.3 | mwghuman30K#B:9411 | -2.343357 | 4.07526E-10 | 9.87494E-09 | -7.993821 | 342 | 19920 | 12053.5 | 0 |
| cyclin G1 (CCNG1), transcript variant 1, mRNA | NP_004051.1 | NM_004060.3 | mwghuman30K#B:5261 | -1.83737 | 2.79204E-08 | 4.64998E-07 | -6.214776 | 365 | 9269.5 | 4453 | 7 |
| F-box protein 34 (FBXO34), mRNA | NP_060413.2 | NM_017943.2 | mwghuman30K#B:4885 | -1.801846 | 1.15594E-06 | 1.13272E-06 | -7.165506 | 365.5 | 17957.5 | 13192.75 | 5 |
| hypothetical protein xp_097916 loc150582 | | XM_097916 | mwghuman30K#B:6228 | -2.291304 | 2.69775E-08 | 3.84322E-06 | -5.299383 | 375 | 3591 | 1276 | |
| RNA pseudouridylate synthase domain containing 4 (RPUSD4), mRNA | NP_116184.1 | NM_032795.1 | mwghuman30K#B:6888 | -1.588438 | 2.0145E-10 | 1.14227E-08 | -8.404434 | 407 | 15747.5 | 11247 | 5 |

Figure 6 (cont)

| Gene name/symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| WD repeat domain 33 (WDR33), transcript variant 2, mRNA | NP_001006623.1 | NM_001006622.1 | mwghuman30K#A:08115 | -1.765322 | 1.47232E-07 | 1.45307E-06 | -6.190057 | 413 | 14876 | 13787.5 | 8 |
| FLJ20859 gene (FLJ20859), transcript variant 1, mRNA | NP_001025162.1 | NM_001029991.1 | mwghuman30K#A:10470 | -1.708985 | 8.133E-08 | 1.13272E-06 | -6.182853 | 420.5 | 3781 | 2693.75 | |
| activating transcription factor 3 (ATF3), transcript variant 2, mRNA | NP_004015.3 | NM_004024.3 | mwghuman30K#A:00568 | -3.134291 | 8.40437E-06 | 1.51698E-07 | -7.446028 | 421 | 13832.5 | 5301.25 | 3 |
| cytochrome P450, family 3, subfamily A, polypeptide 5 (CYP3A5), mRNA | NP_000768.1 | AL161725.13.1.181179.3 | mwghuman30K#A:04559 | -2.482162 | 7.0225E-08 | 1.9772E-06 | -4.813425 | 451.5 | 20350.5 | 12190.5 | 2 |
| ensembl genscan prediction | | | mwghuman30K#C:3443 | -1.955495 | 1.19555E-09 | 9.24336E-06 | -5.681512 | 455 | 2738.5 | 1799 | |
| KIT ligand (KITLG), transcript variant b, mRNA | NP_000890.1 | NM_000899.3 | mwghuman30K#A:07355 | -4.28251 | 3.8867E-06 | 7.23184E-07 | -5.884133 | 470 | 19497 | 10599.75 | 2 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| decay accelerating factor for complement (CD55, Cromer blood group system) (DAF), mRNA | NP_000565.1 | NM_000574.2 | mwghuman3 0K#A:06760 | -2.146033 | 1.44112E-06 | 6.53282E-06 | -5.668164 | 471.5 | 9806.5 | 4753.25 | 10 |
| solute carrier family 25 (mitochondrial carrier; phosphate carrier), member 23 (SLC25A23), mRNA | NP_077008.2 | NM_024103.2 | mwghuman3 0K#A:05530 | -1.465915 | 7.79426E-09 | 8.80903E-07 | -5.741772 | 497 | 16285.5 | 12418.75 | 4 |
| wingless-type MMTV integration site family, member 2B (WNT2B), transcript variant WNT-2B1, mRNA | NP_004176.2 | NM_004185.2 | mwghuman3 0K#A:05696 | -10.745275 | 2.92382E-12 | 3.19726E-07 | -6.175471 | 501 | 10716 | 2016.25 | 0 |
| protocadherin gamma subfamily A, 12 (PCDHGA12), transcript variant 1, mRNA | NP_003726.1 | NM_003735.2 | mwghuman3 0K#A:03393 | -2.070447 | 2.89557E-07 | 6.92439E-06 | -4.982742 | 511 | 2537 | 1931.5 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC010828.3.125573.158193.2 | mwghuman30K#C:4737 | -1.679465 | 2.34945E-07 | 6.18322E-07 | -5.341693 | 511 | 26962 | 25287.75 | |
| olfactory receptor, family 1, subfamily D, member 5 (OR1D5), mRNA | NP_055381.1 | NM_014566.1 | mwghuman30K#A:08766 | -1.640751 | 5.38884E-08 | 4.32856E-06 | -5.134756 | 539.5 | 1644 | 1134 | 0 |
| G protein-coupled receptor 126 (GPR126), transcript variant b1, mRNA | NP_940971.1 | NM_198569.1 | mwghuman30K#B:2989 | -2.181735 | 3.9002E-07 | 1.05021E-05 | -5.047901 | 549 | 15965.5 | 8040.75 | 0 |
| similar to ba408e5.4 novel protein dmpk-like cdc42-binding kinase beta cdc42bpb loc144850 | | XM_090553 | mwghuman30K#B:9158 | -4.265957 | 2.3863E-08 | 5.29006E-07 | -6.259229 | 573 | 1784 | 632 | |
| ubiquitin specific peptidase 9, Y-linked (fat facets-like, Drosophila) (USP9Y), mRNA | NP_004645.2 | NM_004654.3 | mwghuman30K#A:10655 | -1.584065 | 3.40815E-07 | 8.23838E-06 | -5.287284 | 587 | 10035.5 | 7858.25 | 1 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC022554.2.1 1725.14597.1 | mwghuman3 OK#C:7523 | -2.800527 | 1.74508E-07 | 6.41199E-07 | -5.902891 | 597 | 3330 | 1296 | |
| solute carrier family 35 (CMP-sialic acid transporter), member A1 (SLC35A1), mRNA | NP_006407.1 | NM_006416.2 | mwghuman3 OK#B:6203 | -1.879113 | 1.20877E-06 | 5.4811 8E-06 | -5.297694 | 606 | 20639 | 15436.75 | 1 |
| cell line sc30 t receptor alpha chain v-j junctional region tcr v 29.1 j 11 coding sequence reported spans from nucleotide position | | U14083 | mwghuman3 OK#B:9790 | -2.442854 | 9.94216E-08 | 1.14277E-08 | -7.365379 | 617 | 6673 | 2661.5 | |
| chromosome 2 open reading frame 33 (C2orf33), mRNA | NP_064579.3 | NM_020194.4 | mwghuman3 OK#A:06988 | -1.615311 | 3.24982E-07 | 9.24336E-06 | -5.392632 | 624 | 11555.5 | 8868.25 | 4 |
| ensembl genscan prediction | | AC073108.7.1 14033.192530.1 | mwghuman3 OK#C:4991 | -2.137812 | 1.453E-05 | 1.06394E-06 | -6.345675 | 650.5 | 9963.5 | 5676.75 | |

Figure 6 (cont)

| Gene name/symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| UDP-N-acetyl-alpha-D-galactosamine: polypeptide N-acetylgalactosaminyltransferase 7 (GalNAc-T7) (GALNT7), mRNA | NP_059119.1 | NM_017423.1 | mwghuman3 0K#A:01420 | -1.401046 | 7.53042E-08 | 1.13272E-06 | -6.143981 | 656.5 | 10573 | 8997.75 | 2 |
| chromosome 11 open reading frame 1 (C11orf1), mRNA | NP_073598.1 | NM_022761.1 | mwghuman3 0K#A:01834 | -1.81726 | 1.38032E-06 | 1.22937E-05 | -5.104229 | 673.5 | 12025.5 | 9585.25 | 0 |
| heterogeneous nuclear ribonucleoprotein H2 (H') (HNRPH2), transcript variant 1, mRNA | NP_062543.1 | NM_019597.3 | mwghuman3 0K#A:08547 | -2.03901 | 2.40065E-06 | 6.16248E-06 | -5.465662 | 684 | 777 | 472 | 9 |
| Werner syndrome (WRN), mRNA | NP_000544.1 | NM_0005553.2 | mwghuman3 0K#A:03163 | -1.605462 | 7.49706E-08 | 6.16248E-06 | -4.681771 | 696 | 4585 | 4351.25 | 3 |
| ensembl genscan prediction | | AC040160.3.6 1245.138821.5 | mwghuman3 0K#C:7317 | -4.953847 | 7.54477E-12 | 1.43666E-08 | -6.602968 | 706.5 | 4523.5 | 744.5 | |

Figure 6 (cont)

| Gene name/ symbol | protein accession | mRNA ref seq accession | MWG Probe name | median fold change | t-test | WIlcoxon test | SAM | rank score | tumour tissue median intensity rank | non-malignant tissue median intensity rank | blood |
|---|---|---|---|---|---|---|---|---|---|---|---|
| adducin 3 (gamma) (ADD3), transcript variant 1, mRNA | NP_058432.1 | NM_016824.3 | mwghuman3 0K#B:5211 | -2.092475 | 1.34331E-05 | 1.16156E-05 | -5.883251 | 716 | 7668.5 | 4808.75 | 8 |
| hydroxysteroid dehydrogenase like 2 (HSDL2), mRNA | NP_115679.2 | NM_032303.2 | mwghuman3 0K#B:3888 | -2.1317 | 9.39999E-07 | 5.81228E-06 | -5.58267 | 732.5 | 7276.5 | 5055 | 2 |
| DNA-damage-inducible transcript 4 (DDIT4), mRNA | NP_061931.1 | NM_019058.2 | mwghuman3 0K#B:2115 | -2.660775 | 6.68834E-05 | 5.16818E-06 | -5.969252 | 750 | 10960.5 | 5062.75 | 12 |
| RNA binding protein, autoantigenic (hnRNP-associated with lethal yellow homolog (mouse)) (RALY), transcript variant 1, mRNA | NP_057951.1 | NM_016732.1 | mwghuman3 0K#A:06376 | -1.901576 | 1.7076E-07 | 4.32856E-06 | -4.392163 | 750.5 | 977 | 386.5 | 26 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| acyl-CoA synthetase medium-chain family member 3 (ACSM3), transcript variant 1, mRNA | NP_005613.2 | NM_005622.3 | mwghuman30K#B:9076 | -1.967123 | 1.7751E-05 | 7.33836E-06 | -5.050721 | 765.5 | 18906.5 | 12252.25 | 3 |
| BCL2-associated athanogene (BAG1), mRNA | NP_004314.3 | NM_004323.3 | mwghuman30K#A:09581 | -2.525417 | 2.13163E-08 | 5.29006E-07 | -5.934904 | 776 | 9031 | 4503.5 | 1 |
| neural precursor cell expressed, developmentally down-regulated 4 (NEDD4), transcript variant 1, mRNA | NP_006145.1 | NM_006154.1 | mwghuman30K#B:7862 | -1.900818 | 3.7763E-06 | 8.23334E-06 | -5.249282 | 781 | 15497 | 12075 | 2 |
| chromosome 7 open reading frame 19 (C7orf19), mRNA | NP_116220.1 | NM_032831.1 | mwghuman30K#B:2324 | -1.780735 | 4.63759E-06 | 0.000016624 | -5.43532 | 783 | 11586.5 | 6704.75 | 16 |
| calpain 13 (CAPN13), mRNA | NP_653176.2 | NM_144575.2 | mwghuman30K#B:6754 | -1.542431 | 4.41704E-06 | 5.81228E-06 | -4.843249 | 808.5 | 23318 | 19953.5 | 0 |
| homeo box B2 (HOXB2), mRNA | NP_002136.1 | NM_002145.2 | mwghuman30K#A:01639 | -2.702649 | 2.94498E-11 | 5.08294E-08 | -6.774876 | 814.5 | 11537.5 | 6408 | 3 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| coiled-coil domain containing 28A (CCDC28A), mRNA | NP_056254.1 | NM_015439.2 | mwghuman30K#B:3128 | -1.960606 | 1.97345E-06 | 5.48118E-06 | -5.330597 | 826 | 19022 | 14223.75 | 4 |
| myofibrillogenesis regulator 1 (MR-1), transcript variant 1, mRNA | NP_056303.2 | NM_015488.3 | mwghuman30K#B:3179 | -1.526799 | 1.22924E-05 | 6.92439E-06 | -5.874478 | 832 | 13007 | 10755.75 | 6 |
| guanine nucleotide binding protein (G protein), beta polypeptide 2-like 1 (GNB2L1), mRNA | NP_006089.1 | NM_006098.4 | mwghuman30K#C:0841 | -1.789085 | 2.16356E-06 | 4.35419E-05 | -4.900058 | 844.5 | 1710 | 1178 | 106 |
| spectrin repeat containing, nuclear envelope 1 (SYNE1), transcript variant beta, mRNA | NP_056108.1 | NM_015293.1 | mwghuman30K#B:9104 | -1.414534 | 7.52733E-07 | 3.02433E-06 | -5.983107 | 851 | 20159.5 | 17233.75 | 64 |
| ensembl genscan prediction | | AL021155.1.1.107603.5 | mwghuman30K#C:7334 | -1.766409 | 2.12121E-06 | 2.01355E-05 | -4.468876 | 853 | 1264 | 847.5 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| bone morphogenetic protein receptor, type IA (BMPR1A), mRNA | NP_004320.2 | NM_004329.2 | mwghuman3 0K#A:02484 | -1.558632 | 2.22237E-07 | 1.29937E-05 | -4.618211 | 874.5 | 5116 | 5037.5 | 4 |
| IQ motif containing B1 (IQCB1), transcript variant 1, mRNA | NP_0010188 64.1 | NM_0010235 70.1 | mwghuman3 0K#B:4020 | -1.646698 | 2.79495E-05 | 1.62908E-05 | -5.169855 | 882.5 | 10922 | 8773.5 | 2 |
| ensembl genscan prediction | | AC069502.9.1 .18380.1 | mwghuman3 0K#C:3663 | -1.464573 | 6.94397E-07 | 2.53657E-05 | -4.951029 | 901 | 21078 | 19035 | |
| similar to death-associated protein (LOC92196), mRNA | NP_0010179 20.1 | NM_0010179 20.1 | mwghuman3 0K#B:6718 | -2.553467 | 5.76345E-07 | 7.76152E-07 | -5.221107 | 907 | 23255 | 15868 | 0 |
| ensembl genscan prediction | | AC012203.4.1 05191.123571 .1 | mwghuman3 0K#C:4578 | -1.438718 | 3.21936E-05 | 4.85862E-07 | -5.989899 | 907 | 27071.5 | 25867.5 | |
| ensembl genscan prediction mwg oligo matches these RefSeq numbers NM_000986 | | AL158153.8.4 5139.113162. 3 | mwghuman3 0K#C:2173 | -2.089238 | 4.80586E-07 | 4.32856E-06 | -5.395407 | 909.5 | 1290 | 1010.25 | |

Figure 6 (cont)

| Gene name/symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| growth arrest and DNA-damage-inducible, alpha (GADD45A), mRNA | NP_001915.1 | NM_001924.2 | mwghuman3 0K#A:04346 | -1.68216 | 7.53906E-06 | 2.67916E-05 | -4.924921 | 916.5 | 11634.5 | 8596.75 | 3 |
| stress 70 protein chaperone, microsome-associated, 60kDa (STCH), mRNA | NP_008879.3 | NM_006948.4 | mwghuman3 0K#A:05064 | -1.761334 | 4.58163E-05 | 1.72268E-05 | -5.784774 | 916.5 | 10794 | 6231.25 | 5 |
| ensembl genscan prediction | | Z84474.1.1.1 07526.2 | mwghuman3 0K#C:0911 | -1.884499 | 1.62444E-08 | 2.23413E-06 | -5.434325 | 933.5 | 1974 | 1488.5 | |
| family with sequence similarity 44, member B (FAM44B), mRNA | NP_612378.1 | NM_138369.1 | mwghuman3 0K#B:4192 | -1.357114 | 7.91633E-07 | 1.64431E-06 | -6.047548 | 942.5 | 15308.5 | 13004.75 | 1 |
| ensembl genscan prediction | | AC078789.15.1.55074.2 | mwghuman3 0K#C:6283 | -1.786484 | 1.80836E-06 | 3.70831E-05 | -4.861731 | 948 | 25553.5 | 22990.75 | |
| citrate lyase beta like (CLYBL), transcript variant 1, mRNA | NP_612124.3 | NM_138280.3 | mwghuman3 0K#B:8855 | -1.444822 | 1.17336E-06 | 5.16818E-06 | -5.775319 | 953 | 21231 | 19330.25 | 1 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AP001015.3.6 6054.115655.1 | mwghuman3 OK#C:3998 | -1.709242 | 1.48259E-07 | 7.36585E-05 | -4.504002 | 972.5 | 3374.5 | 2739.5 | |
| ensembl genscan prediction | | AL159169.14. 1.86155.2 | mwghuman3 OK#C:4465 | -1.474035 | 8.96434E-07 | 3.25437E-06 | -5.020854 | 998.5 | 28575 | 28030 | |
| chromosome 6 open reading frame 130 (C6orf130), mRNA | NP_659500.1 | NM_145063.2 | mwghuman3 OK#B:4652 | -1.674296 | 1.77778E-05 | 3.32944E-05 | -4.846371 | 1011.5 | 14804 | 10754.75 | 3 |
| methyltransfera se like 1 (METTL1), transcript variant 1, mRNA | NP_005362.1 | NM_005371.3 | mwghuman3 OK#A:00607 | -1.464425 | 1.73108E-07 | 5.48118E-06 | -5.447819 | 1026 | 943 | 645.5 | 2 |
| nucleosome assembly protein 1-like 4 (NAP1L4), mRNA | NP_005960.1 | NM_005969.3 | mwghuman3 OK#A:00706 | -1.902267 | 1.44614E-05 | 6.99321E-05 | -4.962357 | 1042.5 | 10336.5 | 8978.5 | 12 |
| tumor protein D52 (TPD52), transcript variant 3, mRNA | NP_005070.1 | NM_005079.2 | mwghuman3 OK#A:05633 | -1.55805 | 1.79544E-06 | 3.15409E-05 | -4.599069 | 1070 | 19033 | 14646.75 | 4 |
| EH-domain containing 4 (EHD4), mRNA | NP_644670.1 | NM_139265.2 | mwghuman3 OK#B:5911 | -1.64935 | 1.97896E-05 | 3.70831E-05 | -4.903865 | 1077 | 12134 | 9187.5 | 4 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| fibroblast growth factor receptor 4 (FGFR4), transcript variant 2, mRNA | NP_075252.2 | NM_022963.2 | mwghuman3 0K#B:8174 | -2.638426 | 2.02402E-06 | 3.21175E-06 | -6.251766 | 1087.5 | 17096 | 9762.5 | 0 |
| KIAA0674 (KIAA0674), mRNA | XP_376903.2 | XM_376903.2 | mwghuman3 0K#B:0240 | -1.362276 | 3.68739E-06 | 3.62055E-06 | -5.432041 | 1092.5 | 10744 | 9097.25 | 4 |
| chromosome 16 bac clone cit987sk-a-363e6 | | U91321 | mwghuman3 0K#B:5375 | -1.568388 | 5.91844E-05 | 6.53282E-06 | -6.349455 | 1114.5 | 10576.5 | 6083.25 | |
| ensembl genscan prediction | | AC073610.11. 63494.102478.3 | mwghuman3 0K#C:1337 | -1.828108 | 1.68631E-06 | 1.30096E-05 | -5.253574 | 1114.5 | 1434.5 | 737 | |
| androgen receptor (AR), transcript variant 1, mRNA | NP_000035.2 | NM_000044.2 | mwghuman3 0K#A:01003 | -1.575215 | 1.18973E-07 | 1.54035E-05 | -4.291628 | 1120.5 | 18067.5 | 15252.5 | 0 |
| thyroid transcription factor 1 (TITF1), mRNA | NP_003308.1 | NM_003317.3 | mwghuman3 0K#A:07197 | -1.466987 | 8.57665E-07 | 1.54585E-06 | -6.023277 | 1124.5 | 2139 | 1026.25 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| spectrin repeat containing, nuclear envelope 1 (SYNE1), transcript variant longest, mRNA | NP_892006.1 | NM_182961.1 | mwghuman30K#C:2340 | -1.440164 | 6.37872E-05 | 2.15085E-05 | -5.805222 | 1124.5 | 26092.5 | 21681.5 | 64 |
| ensembl genscan prediction | | AC019084.7.93515.134992.2 | mwghuman30K#C:5482 | -1.55364 | 1.48892E-06 | 7.77593E-06 | -5.043927 | 1126.5 | 8785.5 | 8789.5 | |
| ensembl genscan prediction | | AC026235.12.9210.157122.4 | mwghuman30K#C:3969 | -1.693854 | 8.74991E-08 | 0.000122803 | -4.393663 | 1136.5 | 804 | 493.5 | |
| ensembl genscan prediction | | AP002840.1.99623.121675.1 | mwghuman30K#C:5950 | -1.784079 | 2.96992E-05 | 7.75722E-05 | -4.69759 | 1156 | 16693.5 | 14033.25 | |
| CDC-like kinase 1 (CLK1), transcript variant 1, mRNA | NP_004062.2 | NM_004071.2 | mwghuman30K#A:07840 | -2.034707 | 6.15281E-05 | 6.99321E-05 | -5.146308 | 1157.5 | 12199 | 7934.75 | 4 |
| lipin 1 (LPIN1), mRNA | NP_663731.1 | NM_145693.1 | mwghuman30K#B:8172 | -1.851742 | 1.40757E-07 | 2.98753E-05 | -4.301729 | 1159.5 | 3757 | 2609 | 2 |
| lamin A/C (LMNA), transcript variant 2, mRNA | NP_005563.1 | NM_005572.2 | mwghuman30K#A:08943 | -1.724223 | 9.63727E-05 | 5.67358E-05 | -5.305029 | 1162.5 | 4447 | 3295 | 10 |
| ensembl genscan prediction | | AC079456.15.119608.151490.1 | mwghuman30K#C:3309 | -1.39662 | 6.38081E-06 | 4.32856E-06 | -6.439308 | 1169.5 | 26755.5 | 26493.5 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| similar to riken cdna 1500002b03 clone mgc:12928 image:429841 4 | | BC007768 | mwghuman3 0K#B:4242 | -1.518362 | 5.21322E-06 | 3.51403E-05 | -4.463332 | 1171 | 21159 | 20375 | |
| ensembl genscan prediction | | AC027086.2.2 3033.31927.1 | mwghuman3 0K#C:6982 | -1.659003 | 1.16113E-11 | 3.82785E-07 | -6.295271 | 1172.5 | 2757 | 2062.75 | |
| hyaluronogluco saminidase 3 (HYAL3), mRNA | NP_003540.2 | NM_003549.2 | mwghuman3 0K#A:09529 | -2.01277 | 6.70905E-08 | 1.16156E-05 | -4.684969 | 1175 | 4326 | 3464.5 | 4 |
| ensembl genscan prediction | | AC083822.10. 126464.12912 2.1 | mwghuman3 0K#C:9101 | -1.479602 | 6.01319E-06 | 2.53657E-05 | -4.526959 | 1177 | 22091.5 | 20578.5 | |
| VprBP protein (VprBP), mRNA | NP_055518.1 | NM_014703.1 | mwghuman3 0K#B:0332 | -1.720326 | 3.28082E-05 | 2.40122E-05 | -5.246863 | 1178 | 17312.5 | 14031 | 0 |
| nuclear RNA export factor 1 (NXF1), mRNA | NP_006353.2 | NM_006362.3 | mwghuman3 0K#B:1047 | -1.485619 | 7.48559E-05 | 1.62908E-05 | -5.176445 | 1195.5 | 15210 | 14049.75 | 20 |
| empty spiracles homolog 2 (Drosophila) (EMX2), mRNA | NP_004089.1 | NM_004098.2 | mwghuman3 0K#B:9279 | -1.745086 | 9.4996E-09 | 5.64117E-07 | -5.709572 | 1199.5 | 19380 | 10749.25 | 0 |
| homeo box D8 (HOXD8), mRNA | NP_062458.1 | NM_019558.2 | mwghuman3 0K#B:3465 | -1.41555 | 6.70306E-08 | 2.1019E-06 | -5.674131 | 1206 | 9672.5 | 7512.25 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| pro2591 predicted protein of hq2591 | | AF119886 | mwghuman3 0K#B:1001 | -1.487408 | 7.83971E-05 | 1.30297E-05 | -4.929888 | 1212 | 27543.5 | 26699 | 0 |
| ensembl genscan prediction | | AC016432.3.1 6946.19371.1 | mwghuman3 0K#C:6058 | -3.528975 | 4.33482E-13 | 5.08294E-08 | -6.731611 | 1216.5 | 3962.5 | 1303 | |
| ensembl genscan prediction | | AF286885.1.7 6372.115954.3 | mwghuman3 0K#C:7800 | -1.83051 | 1.14443E-05 | 5.11795E-05 | -4.359199 | 1218 | 21163.5 | 21224.5 | |
| zinc finger protein 25 (KOX 19) (ZNF25), mRNA | NP_659448.1 | NM_145011.2 | mwghuman3 0K#C:1648 | -1.473477 | 6.43814E-09 | 4.35863E-07 | -5.84264 | 1253.5 | 21026.5 | 19171 | 1 |
| zinc finger protein 626 (ZNF626), mRNA | NP_660340.1 | NM_145297.2 | mwghuman3 0K#B:4148 | -1.773183 | 2.31455E-06 | 6.63845E-05 | -4.294361 | 1266 | 14806.5 | 10341 | 1 |
| growth arrest and DNA-damage-inducible, beta (GADD45B), mRNA | NP_056490.1 | NM_015675.1 | mwghuman3 0K#A:00537 | -1.950707 | 0.000200032 | 2.03519E-05 | -5.558029 | 1270.5 | 13309 | 8615.5 | 5 |
| nebulette (NEBL), transcript variant 1, mRNA | NP_006384.1 | NM_006393.1 | mwghuman3 0K#A:10459 | -1.513391 | 1.95755E-05 | 3.15409E-05 | -4.789714 | 1276 | 22936 | 20052.5 | 1 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein pro2832 pro2832 | | NM_018541 | mwghuman3 0K#A:00371 | -1.457098 | 3.06355E-05 | 6.99321E-05 | -5.164495 | 1289.5 | 16692.5 | 14266.5 | |
| ring finger protein 44 (RNF44), mRNA | NP_055716.1 | NM_014901.4 | mwghuman3 0K#A:10680 | -1.353366 | 7.76079E-07 | 2.37433E-06 | -5.842265 | 1292 | 6288.5 | 4664.5 | 1 |
| REX1, RNA exonuclease 1 homolog (S. cerevisiae) (REXO1), mRNA | NP_065746.2 | NM_020695.2 | mwghuman3 0K#B:8218 | -1.36867 | 1.73225E-05 | 2.38069E-05 | -5.111364 | 1305.5 | 4933 | 3309.5 | 6 |
| pyrimidinergic receptor P2Y, G-protein coupled, 4 (P2RY4), mRNA | NP_002556.1 | NM_002565.3 | mwghuman3 0K#A:00433 | -1.732075 | 5.0193E-08 | 2.68048E-06 | -5.510614 | 1309 | 18307 | 12139.5 | 0 |
| ensembl genscan prediction | | AL023804.2.1 .96460.1 | mwghuman3 0K#C:5405 | -1.533348 | 1.03637E-06 | 2.806E-05 | -4.693772 | 1313 | 28610 | 27980.5 | |
| ensembl genscan prediction | | AL139823.3.4 9422.51911.1 | mwghuman3 0K#C:8800 | -1.894452 | 4.41409E-05 | 0.000129 14 | -4.650026 | 1320 | 11214.5 | 7548 | |
| similar to hypothetical protein (LOC440804), mRNA | XP_036936.3 | XM_036936.3 | mwghuman3 0K#B:4832 | -4.049648 | 5.38047E-11 | 1.51698E-07 | -6.579174 | 1332 | 3647 | 996.5 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome X open reading frame 41 (CXorf41), mRNA | NP_775765.1 | NM_173494.1 | mwghuman3 0K#C:1526 | -1.448331 | 1.77872E-05 | 2.53657E-05 | -5.140193 | 1334 | 27414 | 24062.75 | 0 |
| chromosome 20 open reading frame 152 (C20orf152), mRNA | NP_543024.1 | NM_080834.1 | mwghuman3 0K#B:3251 | -1.948612 | 6.84261E-06 | 1.82138E-05 | -4.987586 | 1349 | 10775 | 8652.5 | 0 |
| ensembl genscan prediction | | AL390766.11. 35686.142382 .1 | mwghuman3 0K#C:4546 | -1.516487 | 5.60986E-05 | 4.81914E-05 | -4.642986 | 1352 | 28469.5 | 27078.25 | |
| phosphorylase, glycogen; liver (Hers disease, glycogen storage disease type VI) (PYGL), mRNA | NP_002854.3 | NM_002863.3 | mwghuman3 0K#A:04342 | -2.190281 | 5.14475E-06 | 0.000269936 | -4.316788 | 1388.5 | 10289.5 | 7222 | 21 |
| ensembl genscan prediction | | AC013764.3.1 17501.157349 .1 | mwghuman3 0K#C:3627 | -1.671949 | 8.77886E-06 | 7.36585E-05 | -4.28185 | 1395.5 | 1205 | 826.5 | |
| follistatin-like 4 (FSTL4), mRNA | NP_055897.1 | NM_015082.1 | mwghuman3 0K#B:0510 | -1.544042 | 4.79688E-05 | 4.35419E-05 | -4.607654 | 1405.5 | 17051 | 12319 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome 14 open reading frame 168 (C14orf168), mRNA | NP_113615.1 | NM_031427.1 | mwghuman3 0K#B:4011 | -1.512002 | 1.56095E-05 | 5.97939E-05 | -4.695177 | 1414 | 15738 | 14705.75 | 1 |
| aldehyde dehydrogenase 7 family, member A1 (ALDH7A1), mRNA | NP_001173.1 | NM_001182.2 | mwghuman3 0K#A:08361 | -1.837545 | 4.80787E-07 | 0.000105 506 | -3.903403 | 1433 | 20103.5 | 14345.5 | 2 |
| ensembl genscan prediction | | AC010904.9.3 83.204857.4 | mwghuman3 0K#C:7433 | -1.40403 | 4.74755E-05 | 3.07694E-05 | -4.852328 | 1444 | 27423.5 | 25979.25 | |
| kallikrein 8 (neuropsin/ova sin) (KLK8), transcript variant 2, mRNA | NP_653088.1 | NM_144505.1 | mwghuman3 0K#B:0129 | -2.091505 | 3.56009E-06 | 2.61655E-06 | -5.991679 | 1449.5 | 8391 | 6488 | 0 |
| leucine zipper, down-regulated in cancer 1-like (LDOC1L), mRNA | NP_115663.2 | NM_032287.2 | mwghuman3 0K#B:8710 | -1.501021 | 2.6566E-06 | 1.22937E-05 | -4.280727 | 1454.5 | 16509.5 | 14157 | 0 |
| two pore segment channel 1 (TPCN1), mRNA | NP_060371.2 | NM_017901.3 | mwghuman3 0K#B:7759 | -1.497443 | 4.32588E-06 | 3.29944E-05 | -4.567011 | 1460.5 | 17545 | 11635.75 | 8 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein MGC11242 (MGC11242), mRNA | NP_077296.1 | NM_024320.2 | mwghuman3 0K#A:05130 | -1.527839 | 2.70218E-05 | 1.72268E-05 | -4.004461 | 1463.5 | 17565 | 13134.5 | 0 |
| phosphofurin acidic cluster sorting protein 1 (PACS1), mRNA | NP_060496.2 | NM_018026.2 | mwghuman3 0K#B:7703 | -1.494259 | 5.23361E-05 | 7.36585E-05 | -4.899266 | 1482.5 | 9352 | 7757.75 | 19 |
| hypothetical protein xp_036406 loc91138 | | XM_036406 | mwghuman3 0K#B:8080 | -1.533764 | 1.02161E-05 | 4.59223E-05 | -4.93538 | 1486.5 | 15372.5 | 14652 | |
| KIAA1274 (KIAA1274), mRNA | NP_055246.1 | NM_014431.1 | mwghuman3 0K#B:8047 | -1.41942 | 7.87044E-05 | 2.27276E-05 | -5.659345 | 1488.5 | 8059 | 5065 | 0 |
| ensembl genscan prediction | | AC090651.1.9 901.36661.2 | mwghuman3 0K#C:6027 | -1.525691 | 2.39913E-05 | 7.36585E-05 | -4.620984 | 1489.5 | 21092 | 20253 | |
| hypothetical protein FLJ13111 (FLJ13111), mRNA | NP_079358.1 | NM_025082.1 | mwghuman3 0K#A:02690 | -1.496988 | 3.69096E-05 | 7.08197E-05 | -4.489468 | 1494 | 4861 | 7579.25 | 10 |
| glycophorin C (Gerbich blood group) (GYPC), transcript variant 1, mRNA | NP_002092.1 | NM_002101.3 | mwghuman3 0K#A:01278 | -1.628829 | 9.49623E-06 | 0.000135 784 | -4.110107 | 1502 | 8042 | 6771 | 2 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical LOC401510 (LOC401510), mRNA | XP_376843.2 | XM_376843.2 | mwghuman3 0K#B:6807 | -1.402922 | 3.03035E-06 | 0.000105506 | -4.471835 | 1504 | 13882.5 | 11233.25 | 0 |
| ensembl genscan prediction | | AC068282.4.1 68870.201224.1 | mwghuman3 0K#C:1421 | -1.273265 | 1.4683E-06 | 4.32856E-06 | -5.673395 | 1505.5 | 4650 | 3232.25 | |
| phospholipase A2, group IVA (cytosolic, calcium-dependent) (PLA2G4A), mRNA | NP_077734.1 | NM_024420.1 | mwghuman3 0K#C:2726 | -1.656839 | 1.32347E-05 | 2.82936E-05 | -4.522341 | 1508.5 | 17687.5 | 14140.5 | 5 |
| plastin 1 (I isoform) (PLS1), mRNA | NP_002661.1 | NM_002670.1 | mwghuman3 0K#A:06551 | -1.626206 | 5.67628E-05 | 2.98753E-05 | -4.952263 | 1509.5 | 20943 | 14040.5 | 1 |
| neurobeachin-like 1 (NBEAL1), mRNA | NP_945183.1 | NM_198945.1 | mwghuman3 0K#C:8646 | -1.528665 | 7.51176E-06 | 2.82936E-05 | -5.005478 | 1511.5 | 23554.5 | 20060 | 3 |
| alcohol dehydrogenase 4 (class II), pi polypeptide (ADH4), mRNA | NP_000661.2 | NM_000670.3 | mwghuman3 0K#A:04002 | -1.485933 | 6.40488E-05 | 7.36585E-05 | -4.608649 | 1520.5 | 22288 | 20240.75 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| clone rp5-947l8 on chromosome 1p34.1-36.11. contains ests gsss and stss. part of novel cub sushi scr repeat domain containing p | | AL355178 | mwghuman3 0K#B:9614 | -1.466888 | 8.43097E-06 | 3.15409E-05 | -4.397922 | 1529 | 4947.5 | 4650.25 | |
| cytochrome b5 reductase 3 (CYB5R3), transcript variant M, mRNA | NP_000389.1 | NM_000398.4 | mwghuman3 0K#A:01423 | -1.497796 | 0.0001216 06 | 9.05266E-05 | -5.28459 | 1531.5 | 9574.5 | 6353.5 | 9 |
| clone flb5634 pro1477 predicted protein of hq1477 | | AF130059 | mwghuman3 0K#B:1074 | -1.699661 | 1.17568E-05 | 3.32944E-05 | -4.802532 | 1535 | 5685 | 3946.75 | 10 |
| zinc finger, DHHC-type containing 2 (ZDHHC2), mRNA | NP_057437.1 | NM_016353.2 | mwghuman3 0K#A:03494 | -1.588633 | 8.03858E-06 | 0.000105 506 | -4.741236 | 1536 | 13684.5 | 10087.5 | 0 |
| cone-rod homeobox (CRX), mRNA | NP_000545.1 | NM_000554.2 | mwghuman3 0K#A:09219 | -3.022299 | 2.51326E-05 | 9.24336E-06 | -5.849282 | 1548 | 16588.5 | 7500.5 | 0 |

Figure 6 (cont)

| Gene name/symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome 14 open reading frame 154 (C14orf154), transcript variant 1, mRNA | NP_115609.2 | NM_032233.2 | mwghuman30K#B:2665 | -1.704609 | 8.00302E-05 | 0.000166293 | -4.427372 | 1561.5 | 16629 | 15080.75 | 5 |
| hypothetical protein xp_098665 loc155085 | | XM_098665 | mwghuman30K#B:6056 | -1.672814 | 4.27782E-05 | 0.000142749 | -4.312941 | 1566.5 | 8795 | 6847.25 | |
| clone hq0117 pro0117 | | AF090895 | mwghuman30K#B:0914 | -1.888405 | 1.18377E-05 | 9.05266E-05 | -4.735768 | 1570.5 | 20158 | 14933.5 | 4 |
| prostate and breast cancer overexpressed 1 (PBOV1), mRNA | NP_067648.1 | NM_021635.1 | mwghuman30K#A:05114 | -1.610345 | 5.40979E-06 | 8.1682E-05 | -4.437567 | 1571.5 | 22494.5 | 19845.75 | 0 |
| esterase D/formylglutathione hydrolase (ESD), mRNA | NP_001975.1 | NM_001984.1 | mwghuman30K#C:2641 | -1.535083 | 6.75303E-06 | 4.84259E-05 | -4.777065 | 1574 | 8049 | 4838.75 | 6 |
| ATG4 autophagy related 4 homolog B (S. cerevisiae) (ATG4B), transcript variant 1, mRNA | NP_037457.3 | NM_013325.4 | mwghuman30K#B:2748 | -1.348856 | 8.59727E-06 | 1.6224E-05 | -4.71932 | 1575 | 15166 | 16712.25 | 13 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| NADPH oxidase 1 (NOX1), transcript variant NOH-1Lv, mRNA | NP_039249.1 | NM_013955.1 | mwghuman3 0K#B:1370 | -1.903809 | 5.04367E-06 | 2.65189E-05 | -3.799677 | 1585.5 | 18807.5 | 17371.5 | 0 |
| ensembl genscan prediction | | AL445675.9.1.171985.3 | mwghuman3 0K#C:8741 | -1.774793 | 2.60881E-05 | 0.000182916 | -4.133137 | 1598 | 22483.5 | 18071.5 | |
| putative nuclear protein ORF1-FL49 (ORF1-FL49), mRNA | NP_115788.1 | NM_032412.2 | mwghuman3 0K#B:7958 | -1.499659 | 6.10749E-05 | 3.32944E-05 | -4.457256 | 1610.5 | 8598 | 4986 | 8 |
| THUMP domain containing 1 (THUMPD1), mRNA | NP_060206.2 | NM_017736.3 | mwghuman3 0K#B:2088 | -1.313257 | 4.11592E-07 | 6.53282E-06 | -5.325518 | 1651.5 | 14877 | 15313.5 | 0 |
| glutaminyl-peptide cyclotransferase (glutaminyl cyclase) (QPCT), mRNA | NP_036545.1 | NM_012413.3 | mwghuman3 0K#A:09422 | -1.769571 | 4.69509E-07 | 0.000122803 | -3.882851 | 1651.5 | 11960 | 8357.75 | 2 |
| PHD finger protein 23 (PHF23), mRNA | NP_077273.1 | NM_024297.1 | mwghuman3 0K#A:02678 | -1.398461 | 1.43961E-05 | 0.000109884 | -4.356774 | 1657.5 | 10656.5 | 9355.75 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| nasopharyngeal carcinoma associated gene protein-8 (NAG8), mRNA | NP_055226.1 | NM_014411.2 | mwghuman3 0K#B:1482 | -1.388055 | 2.38325E-05 | 5.10584E-05 | -4.601658 | 1660 | 15731.5 | 12161 | 0 |
| ensembl genscan prediction | | AC013487.5.1 02379.117540 .1 | mwghuman3 0K#C:3348 | -1.465932 | 0.0001448 57 | 2.37433E-06 | -6.225756 | 1662 | 14711 | 9423 | |
| ensembl genscan prediction | | AC079757.5.5 4037.62672.1 | mwghuman3 0K#C:3844 | -1.486502 | 2.69625E-05 | 4.12788E-05 | -4.765229 | 1684.5 | 25678.5 | 23575.5 | |
| hypothetical protein FLJ22313 (FLJ22313), mRNA | NP_071768.2 | NM_022373.3 | mwghuman3 0K#B:3974 | -1.47429 | 0.0001047 25 | 5.67358E-05 | -4.784258 | 1688.5 | 8360.5 | 9165.25 | 2 |
| holocytochrome c synthase (cytochrome c heme-lyase (HCCS), mRNA | NP_005324.2 | NM_005333.2 | mwghuman3 0K#A:04510 | -2.084412 | 0.0003326 32 | 0.000211 886 | -5.979649 | 1692.5 | 10130.5 | 5488.25 | 4 |
| dual specificity phosphatase 5 (DUSP5), mRNA | NP_004410.3 | NM_004419.3 | mwghuman3 0K#A:04028 | -1.866767 | 5.52516E-05 | 2.27276E-05 | -5.708882 | 1694.5 | 16243.5 | 8885 | 2 |
| hypothetical protein FLJ20245 (FLJ20245), mRNA | NP_060193.1 | NM_017723.1 | mwghuman3 0K#B:2083 | -1.525601 | 6.09068E-05 | 0.000116 76 | -4.325617 | 1697 | 16122 | 13101 | 3 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| protein kinase, AMP-activated, gamma 2 non-catalytic subunit (PRKAG2), mRNA | NP_057287.2 | NM_016203.2 | mwghuman30K#A:00771 | -1.408092 | 1.41299E-05 | 8.59969E-05 | -4.435082 | 1697.5 | 16315.5 | 13437.25 | 5 |
| clone rp11-314a4 on chromosome 20. contains part of the eya2 eyes absent drosophila homolog 2 ests an sts and gsss starts i | | AL359434 | mwghuman30K#B:9638 | -1.591958 | 1.67257E-05 | 6.56055E-05 | -4.203762 | 1702 | 25348.5 | 23840.75 | |
| hypothetical protein pro1598 pro1598 | | NM_018503 | mwghuman30K#B:0983 | -1.446989 | 3.89533E-06 | 1.30096E-05 | -5.339446 | 1716.5 | 24112.5 | 22618.75 | |
| NIMA (never in mitosis gene a)- related kinase 9 (NEK9), mRNA | NP_149107.3 | NM_033116.3 | mwghuman30K#C:0238 | -1.359292 | 3.922E-05 | 4.35419E-05 | -4.78725 | 1722.5 | 10134.5 | 7455.5 | 5 |
| glycine receptor, alpha 3 (GLRA3), mRNA | NP_006520.1 | NM_006529.1 | mwghuman30K#A:03690 | -1.412224 | 0.00010376 3 | 8.1682E-05 | -4.59741 | 1726 | 9472.5 | 8083.25 | 2 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC004408.1.1.113252.2 | mwghuman30K#C:9512 | -1.54073 | 2.55537E-06 | 1.54035E-05 | -3.618774 | 1727 | 2977 | 2622.75 | |
| ensembl genscan prediction | | AP001655.2.148977.153525.1 | mwghuman30K#C:7868 | -1.285997 | 2.64478E-05 | 1.96829E-05 | -4.601991 | 1746 | 28566 | 28245.5 | |
| HERV-H LTR-associating 3 (HHLA3), transcript variant 3, mRNA | NP_001031722.1 | NM_001036645.1 | mwghuman30K#B:1046 | -2.043346 | 8.67677E-05 | 9.52067E-05 | -3.941702 | 1759 | 13925.5 | 11798 | 0 |
| ensembl genscan prediction | | AL355497.14.1.215397.9 | mwghuman30K#C:7911 | -3.056765 | 1.10766E-06 | 3.82785E-07 | -6.916789 | 1760 | 5672.5 | 2481.25 | |
| fibronectin leucine rich transmembrane protein 3 (FLRT3), transcript variant 1, mRNA | NP_037413.1 | NM_013281.2 | mwghuman30K#A:05822 | -4.204569 | 1.4941E-08 | 9.99201E-07 | -6.042443 | 1770 | 18156 | 9231.25 | 0 |
| cyp3a5 allele cyp3a5*3 alternatively spliced | | AF355802 | mwghuman30K#B:1830 | -1.371576 | 7.33293E-06 | 1.91497E-05 | -4.362299 | 1784 | 26198.5 | 24518.25 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| microfibrillar-associated protein 3-like (MFAP3L), transcript variant 1, mRNA | NP_067679.5 | NM_021647.5 | mwghuman3 0K#B:0217 | -1.987417 | 0.0001373 75 | 1.98715E-06 | -4.959479 | 1785 | 22262 | 18475.25 | 3 |
| cell division cycle associated 7 (CDCA7), transcript variant 1, mRNA | NP_114148.2 | NM_031942.3 | mwghuman3 0K#B:4810 | -1.959598 | 9.26637E-05 | 0.000150 506 | -4.246093 | 1788 | 14826 | 12577.25 | 1 |
| WD repeat domain 61 (WDR61), mRNA | NP_079510.1 | NM_025234.1 | mwghuman3 0K#B:1624 | -1.531798 | 0.0001544 91 | 0.000105 506 | -4.38785 | 1801.5 | 9756.5 | 8041.75 | 3 |
| protein kinase, AMP-activated, beta 1 non-catalytic subunit (PRKAB1), mRNA | NP_006244.2 | NM_006253.4 | mwghuman3 0K#A:04996 | -1.514877 | 9.29449E-05 | 0.000105 506 | -4.4366 | 1805.5 | 16011.5 | 13954 | 3 |
| zinc finger, A20 domain containing 2 (ZA20D2), mRNA | NP_005998.1 | NM_006007.1 | mwghuman3 0K#A:10213 | -1.857923 | 2.78106E-06 | 2.67916E-05 | -4.781221 | 1808.5 | 6856.5 | 4563.25 | 13 |
| similar to pro2852 loc93374 | | XM_050978 | mwghuman3 0K#B:7206 | -1.359998 | 8.48914E-05 | 6.30077E-05 | -5.206744 | 1817 | 19166 | 16438 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| catalase (CAT), mRNA | NP_001743.1 | NM_001752.2 | mwghuman30K#C:3530 | -2.225675 | 8.1938E-07 | 6.92439E-06 | -4.777325 | 1820 | 7219.5 | 4208.75 | 31 |
| peptidylprolyl isomerase (cyclophilin)-like 2 (PPIL2), transcript variant 2, mRNA | NP_680480.1 | NM_148175.1 | mwghuman30K#B:6262 | -1.384263 | 4.77437E-07 | 4.59274E-06 | -5.396075 | 1834.5 | 3806 | 3514 | 5 |
| periaxin (PRX), transcript variant 2, mRNA | NP_870998.1 | NM_181882.1 | mwghuman30K#A:01781 | -1.399169 | 1.03356E-05 | 6.63845E-05 | -4.549994 | 1838 | 19643.5 | 17122.5 | 0 |
| breast carcinoma amplified sequence 3 (BCAS3), mRNA | NP_060149.2 | NM_017679.2 | mwghuman30K#A:01576 | -1.41274 | 2.55423E-07 | 3.64015E-06 | -4.03611 | 1839 | 15754.5 | 17960.25 | 2 |
| HtrA serine peptidase 2 HTRA2 | AAF66598.1 | AF141307.1 | mwghuman30K#B:1170 | -1.284282 | 2.27894E-05 | 1.86362E-05 | -4.071282 | 1850 | 22760.5 | 20044.75 | |
| ensembl genscan prediction | | AC012095.13.12848.17419.1 | mwghuman30K#C:7012 | -1.517696 | 0.000134314 | 0.000172435 | -4.407333 | 1854 | 26139.5 | 25010.5 | |
| formin binding protein 4 (FNBP4), mRNA | NP_056123.1 | NM_015308.1 | mwghuman30K#B:8897 | -1.360042 | 0.000119422 | 2.15085E-05 | -5.532889 | 1855 | 17142 | 14814.25 | 11 |

Figure 6 (cont)

| Gene name/symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| aldehyde dehydrogenase 1 family, member L1 (ALDH1L1), mRNA | NP_036322.2 | NM_012190.2 | mwghuman30K#A:07479 | -2.396851 | 2.32809E-05 | 0.000157701 | -3.740555 | 1856.5 | 13469 | 8189.5 | 3 |
| ensembl genscan prediction | | AP001487.3.85282.114407.1 | mwghuman30K#C:8733 | -1.603991 | 4.09016E-06 | 5.97939E-05 | -4.353485 | 1870 | 3882 | 3994.75 | |
| ensembl genscan prediction | | AC015651.18.1.191583.4 | mwghuman30K#C:2191 | -1.392136 | 5.55423E-07 | 1.72268E-05 | -4.562358 | 1873.5 | 2463 | 1928.25 | |
| OTU domain containing 5 (OTUD5), mRNA | NP_060072.1 | NM_017602.2 | mwghuman30K#B:7999 | -1.721318 | 3.42749E-06 | 1.37651E-05 | -5.356883 | 1894.5 | 1453 | 1011 | 14 |
| ensembl genscan prediction | | AC026668.5.84589.93793.1 | mwghuman30K#C:5546 | -1.668723 | 3.74924E-06 | 2.40122E-05 | -5.209366 | 1899 | 3201 | 1676.5 | |
| chromosome 20 open reading frame 121 (C20orf121), mRNA | NP_077307.1 | NM_024331.2 | mwghuman30K#A:03031 | -1.520517 | 5.93503E-08 | 1.82138E-05 | -4.163768 | 1906 | 8788 | 6894 | 2 |
| pyruvate dehydrogenase kinase, isozyme 4 (PDK4), mRNA | NP_002603.1 | NM_002612.2 | mwghuman30K#A:07564 | -1.735687 | 1.72294E-05 | 1.22937E-05 | -5.445156 | 1911.5 | 18067 | 13997.25 | 1 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| KIAA1049 protein (KIAA1049), mRNA | NP_055787.1 | NM_014972.1 | mwghuman30K#B:2555 | -1.400381 | 1.30483E-05 | 7.36585E-05 | -4.350759 | 1913.5 | 10972 | 8868.5 | 12 |
| DnaJ (Hsp40) homolog, subfamily B, member 6 (DNAJB6), transcript variant 1, mRNA | NP_490647.1 | NM_058246.3 | mwghuman30K#A:04664 | -1.455502 | 9.60314E-05 | 0.000150 05 | -4.286094 | 1917 | 3609 | 2895.5 | 14 |
| lectin, galactoside-binding, soluble, 3 (galectin 3) (LGALS3), mRNA | NP_002297.1 | NM_002306.1 | mwghuman30K#A:10306 | -1.93733 | 6.69527E-06 | 2.55121E-05 | -4.690215 | 1923 | 2753 | 1803.5 | 6 |
| PTPRF interacting protein, binding protein 2 (liprin beta 2) (PPFIBP2), mRNA | NP_003612.1 | NM_003621.1 | mwghuman30K#B:0552 | -1.881545 | 1.28489E-06 | 2.98753E-05 | -4.14602 | 1937.5 | 6372.5 | 4594.5 | 2 |
| polymerase (DNA directed), lambda (POLL), mRNA | NP_037406.1 | NM_013274.2 | mwghuman30K#B:1279 | -1.399567 | 3.5582E-05 | 2.98753E-05 | -4.793654 | 1938 | 15108.5 | 11461.25 | 8 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| growth differentiation factor 15 (GDF15), mRNA | NP_004855.1 | NM_004864.1 | mwghuman3 0K#A:07217 | -2.483648 | 0.000224134 | 0.00025725 | -4.296268 | 1944 | 6377 | 3127.5 | 2 |
| hypothetical protein xp_089809 loc159765 | | XM_089809 | mwghuman3 0K#B:6474 | -1.381507 | 9.90157E-07 | 2.40122E-05 | -4.093057 | 1949 | 11626.5 | 11522.5 | |
| leucine rich repeat and sterile alpha motif containing 1 (LRSAM1), transcript variant 1, mRNA | NP_612370.3 | NM_138361.3 | mwghuman3 0K#B:4416 | -2.034574 | 0.000184031 | 0.000233537 | -4.13512 | 1959.5 | 7671.5 | 4421.75 | 1 |
| trafficking protein particle complex 6A (TRAPPC6A), mRNA | NP_077013.1 | NM_024108.1 | mwghuman3 0K#A:02117 | -1.452954 | 2.44741E-06 | 2.53657E-05 | -3.509555 | 1985 | 1279 | 1294 | 8 |
| ensembl genscan prediction | | AL357146.10.1.82494.1 | mwghuman3 0K#C:3608 | -1.287782 | 1.49736E-05 | 6.05474E-05 | -4.826559 | 1989 | 28444.5 | 26083.25 | |
| hypothetical protein MGC14327 (MGC14327), mRNA | NP_444273.1 | NM_053045.1 | mwghuman3 0K#B:4427 | -1.504495 | 0.000150258 | 0.000174117 | -4.521635 | 1992 | 16805 | 15440.5 | 4 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| similar to kinesin family member 5b clone mgc:15265 image:429779 3 | | BC009353 | mwghuman3 0K#B:4438 | -1.51682 | 0.0001882 14 | 0.000192 131 | -4.531075 | 1992 | 23071.5 | 21809.75 | |
| potassium channel tetramerisation domain containing 3 (KCTD3), mRNA | NP_057205.2 | NM_016121.3 | mwghuman3 0K#A:04386 | -1.358006 | 1.34593E-05 | 5.38262E-05 | -4.810824 | 1994.5 | 17479.5 | 13203.75 | 3 |
| ensembl genscan prediction | | AC018425.3.1 53134.186975 .1 | mwghuman3 0K#C:3925 | -1.496534 | 0.0001495 25 | 0.000192 131 | -4.315259 | 1997 | 25336 | 25414.75 | |
| guanine nucleotide binding protein (G protein), alpha inhibiting activity polypeptide 1 (GNAI1), mRNA | NP_002060.4 | NM_002069.4 | mwghuman3 0K#A:10201 | -1.631361 | 5.34686E-06 | 0.000433 377 | -3.885346 | 2003 | 16803.5 | 14082 | 1 |
| microtubule-associated protein 4 (MAP4), transcript variant 1, mRNA | NP_002366.2 | NM_002375.3 | mwghuman3 0K#B:4355 | -1.468752 | 0.0001551 87 | 0.000257 25 | -4.423897 | 2004 | 10052 | 9080 | 11 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| nucleolar protein family 6 (RNA-associated) (NOL6), transcript variant alpha, mRNA | NP_075068.2 | NM_022917.4 | mwghuman30K#A:07182 | -1.30257 | 1.12604E-06 | 3.70831E-05 | -4.767639 | 2009 | 10513 | 8821 | 7 |
| cerebral endothelial cell adhesion molecule 1 (CEECAM1), mRNA | NP_057258.2 | NM_016174.3 | mwghuman30K#A:10231 | -1.516413 | 4.80848E-05 | 0.000109198 | -3.667581 | 2014 | 16662.5 | 13757.75 | 0 |
| ubiquinol-cytochrome c reductase, complex III subunit VII, 9.5kDa (UQCRQ), nuclear gene encoding mitochondrial protein, mRNA | NP_055217.2 | NM_014402.3 | mwghuman30K#B:8060 | -1.71221 | 4.79681E-05 | 4.35419E-05 | -5.049156 | 2014 | 4199.5 | 2985.25 | 14 |
| hypothetical protein xp_092745 loc164337 | | XM_092745 | mwghuman30K#B:3255 | -1.386871 | 3.26973E-05 | 0.000165718 | -4.513374 | 2041 | 19510 | 15741.25 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
| --- | --- | --- | --- | --- | --- | --- | --- | --- | --- | --- | --- |
| hypothetical protein FLJ22965 (FLJ22965), mRNA | NP_071384.1 | NM_022101.2 | mwghuman3 0K#A:09776 | -1.903469 | 7.16955E-05 | 0.000475592 | -4.078844 | 2041.5 | 2596 | 2337 | 0 |
| chromosome 9 open reading frame 102 (C9orf102), transcript variant 1, mRNA | NP_064592.1 | NM_020207.2 | mwghuman3 0K#B:6956 | -1.369819 | 3.05523E-05 | 0.000105506 | -4.676244 | 2049 | 16457.5 | 13970 | 0 |
| sphingosine-1 phosphate phosphatase 1 (SGPP1), mRNA | NP_110418.1 | NM_030791.2 | mwghuman3 0K#B:1809 | -1.477332 | 4.90035E-05 | 0.000142749 | -4.328137 | 2062.5 | 20094 | 17541.5 | 1 |
| pleckstrin and Sec7 domain containing 3 (PSD3), transcript variant 1, mRNA | NP_056125.2 | NM_015310.2 | mwghuman3 0K#B:9515 | -1.395381 | 2.70551E-05 | 0.000142896 | -3.953529 | 2072 | 14023 | 13223.25 | 1 |
| hypothetical protein LOC283874 (LOC283874), mRNA | NP_001012749.1 | NM_001012731.1 | mwghuman3 0K#B:2101 | -1.376341 | 1.45793E-05 | 2.67916E-05 | -5.079903 | 2090.5 | 23511.5 | 23000 | 1 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| zinc finger, FYVE domain containing 21 (ZFYVE21), mRNA | NP_076976.1 | NM_024071.2 | mwghuman3 0K#A:05642 | -1.579562 | 0.0001142 53 | 0.000342 648 | -4.238027 | 2094 | 2994.5 | 2740.25 | 0 |
| forkhead box E1 (thyroid transcription factor 2) (FOXE1), mRNA | NP_004464.2 | NM_004473.3 | mwghuman3 0K#A:07899 | -1.678652 | 1.3104E-05 | 0.000192 131 | -3.837954 | 2107 | 7269 | 5293.75 | 0 |
| ensembl genscan prediction | | AL158168.17. 82811.114103 .1 | mwghuman3 0K#C:5892 | -1.54059 | 5.72345E-05 | 8.88591E-06 | -4.136599 | 2114 | 28578 | 27753.75 | |
| similar to per-hexamer repeat protein 5 loc149135 | | XM_089208 | mwghuman3 0K#B:9694 | -1.363387 | 0.0001055 64 | 3.77672E-05 | -3.9371 | 2131 | 27002.5 | 27249.5 | |
| zinc finger, matrin type 1 (ZMAT1), transcript variant 3, mRNA | NP_115817.1 | NM_032441.1 | mwghuman3 0K#C:0106 | -1.423696 | 0.0001562 67 | 0.000211 886 | -4.538065 | 2134.5 | 20339.5 | 17190.25 | 2 |
| endoplasmic reticulum to nucleus signalling 2 (ERN2), mRNA | NP_150296.2 | NM_033266.2 | mwghuman3 0K#B:9444 | -1.735187 | 1.98165E-05 | 2.70994E-05 | -4.509363 | 2135 | 24789 | 18903 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ring finger protein 38 (RNF38), transcript variant 1, mRNA | NP_073618.3 | NM_022781.3 | mwghuman3 0K#B:5588 | -1.302965 | 2.50283E-06 | 2.15085E-05 | -4.986001 | 2138 | 24546.5 | 22148.75 | 1 |
| Myc-induced mitochondria protein (mimitin), mRNA | NP_777549.1 | NM_174889.2 | mwghuman3 0K#B:3716 | -1.474873 | 8.439E-05 | 0.000359234 | -4.207401 | 2151.5 | 9215 | 7030.25 | 1 |
| TGF beta-inducible nuclear protein 1 (TINP1), mRNA | NP_055701.1 | NM_014886.2 | mwghuman3 0K#A:06520 | -1.655993 | 0.000318759 | 0.000571767 | -4.796546 | 2153 | 7530 | 5545.5 | 6 |
| similar to developmental pluripotency associated 5; embryonal stem cell specific gene 1 (LOC341912), mRNA | XP_292301.3 | XM_292301.3 | mwghuman3 0K#B:8134 | -1.639786 | 7.64251E-07 | 4.32856E-06 | -5.437632 | 2155 | 18581.5 | 12815.25 | 1 |
| dehydrogenase/reductase (SDR family) member 3 (DHRS3), mRNA | NP_004744.2 | NM_004753.4 | mwghuman3 0K#B:0738 | -1.439285 | 4.39582E-05 | 0.000222464 | -3.974197 | 2166.5 | 4626 | 3570 | 3 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| flavin containing monooxygenase 4 (FMO4), mRNA | NP_002013.1 | NM_002022.1 | mwghuman3 0K#B:2927 | -1.804252 | 0.00019596 7 | 0.000222 464 | -4.159771 | 2173.5 | 21428 | 18241 | 1 |
| ensembl genscan prediction | | AC022526.4.9 087.13827.1 | mwghuman3 0K#C:9081 | -1.518222 | 0.00012640 9 | 0.000174 117 | -4.437239 | 2174 | 25713.5 | 23316 | |
| serologically defined colon cancer antigen 8 (SDCCAG8), mRNA | NP_006633.1 | NM_006642.1 | mwghuman3 0K#B:4992 | -1.359218 | 5.81032E-06 | 1.22937E -05 | -4.628131 | 2177.5 | 18648 | 16566 | 4 |
| CDC14 cell division cycle 14 homolog B (S. cerevisiae) (CDC14B), transcript variant 2, mRNA | NP_201588.1 | NM_033331.1 | mwghuman3 0K#B:0753 | -1.438486 | 0.00015007 6 | 0.000245 124 | -4.702655 | 2178.5 | 23322 | 22971 | 2 |
| myeloid/lymph oid or mixed-lineage leukemia (trithorax homolog, Drosophila); translocated to, 3 (MLLT3), mRNA | NP_004520.1 | NM_004529.1 | mwghuman3 0K#A:00725 | -1.503791 | 3.87447E-05 | 0.000311 603 | -4.282874 | 2188 | 20164.5 | 17462 | 4 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| cytochrome P450, family 27, subfamily A, polypeptide 1 (CYP27A1), nuclear gene encoding mitochondrial protein, mRNA | NP_000775.1 | NM_000784.2 | mwghuman3 0K#A:07422 | -1.399906 | 4.05019E-05 | 3.91276E-05 | -4.065883 | 2197 | 20714 | 13781.5 | 10 |
| pre-tnk cell associated protein 1f6 3' end | | L17326 | mwghuman3 0K#B:9025 | -1.643879 | 5.92984E-08 | 3.84322E-06 | -5.055927 | 2201 | 6449.5 | 4787.5 | |
| hepcidin antimicrobial peptide (HAMP), mRNA | NP_066998.1 | NM_021175.2 | mwghuman3 0K#A:06397 | -1.279742 | 2.53831E-05 | 1.72268E-05 | -4.893297 | 2205.5 | 3722.5 | 3385.25 | 0 |
| ensembl genscan prediction | | AC078819.13. 1.41283.1 | mwghuman3 0K#C:7792 | -1.349603 | 2.94705E-06 | 7.88194E-05 | -4.262185 | 2213 | 21381.5 | 17800.75 | |
| hypothetical protein BC009862 (LOC90113), mRNA | XP_291077.3 | XM_291077.3 | mwghuman3 0K#B:3668 | -1.769275 | 0.0003405 69 | 0.000454 027 | -4.413577 | 2221.5 | 6261.5 | 5176 | 0 |
| elongation factor, RNA polymerase II, 2 (ELL2), mRNA | NP_036213.1 | NM_012081.3 | mwghuman3 0K#A:00356 | -1.499648 | 5.40285E-05 | 0.000157 701 | -4.384409 | 2223.5 | 14138 | 11702.5 | 4 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| FGFR1 oncogene partner (FGFR1OP), transcript variant 1, mRNA | NP_008976.1 | NM_007045.2 | mwghuman3 0K#B:4675 | -1.513357 | 9.11409E-05 | 0.000233537 | -4.085108 | 2228.5 | 19894 | 19145.25 | 0 |
| ensembl genscan prediction | | AC025953.2.1 16948.127472.1 | mwghuman3 0K#C:6647 | -2.043219 | 0.0001551 45 | 0.000283 207 | -3.955032 | 2231 | 21041 | 17429.5 | |
| EH domain binding protein 1 (EHBP1), mRNA | NP_056067.1 | NM_015252.2 | mwghuman3 0K#B:0385 | -1.35833 | 2.50342E-06 | 6.99321E-05 | -4.628579 | 2249.5 | 13151.5 | 12131 | 5 |
| propionyl Coenzyme A carboxylase, alpha polypeptide (PCCA), mRNA | NP_000273.2 | NM_000282.2 | mwghuman3 0K#B:3551 | -1.505038 | 6.411E-05 | 0.000110 999 | -4.042034 | 2251 | 16323 | 13459 | 5 |
| ensembl genscan prediction | | AL138499.4.1 .185713.1 | mwghuman3 0K#C:4137 | -1.655664 | 1.65577E-05 | 8.59969E-05 | -3.700791 | 2252.5 | 6728 | 6542.5 | |
| ensembl genscan prediction | | AC025937.3.2 8407.38498.1 | mwghuman3 0K#C:9420 | -5.821331 | 1.29566E-11 | 3.14688E-07 | -6.568115 | 2255.5 | 3524 | 1068.5 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| myocilin, trabecular meshwork inducible glucocorticoid response (MYOC), mRNA | NP_000252.1 | NM_000261.1 | mwghuman30K#A:09642 | -1.364785 | 4.61814E-05 | 2.61402E-05 | -4.638227 | 2263 | 23815.5 | 22357.25 | 0 |
| hspc074 | | AF161337 | mwghuman30K#B:1281 | -1.61806 | 1.54965E-06 | 1.54035E-05 | -4.426706 | 2264.5 | 1792 | 1727 | 3 |
| epoxide hydrolase 2, cytoplasmic (EPHX2), mRNA | NP_001970.2 | NM_001979.4 | mwghuman30K#A:08300 | -1.416398 | 5.8666E-06 | 5.81228E-06 | -4.695716 | 2267.5 | 19752.5 | 16857 | 3 |
| centromere protein C 1 (CENPC1), mRNA | NP_001803.2 | NM_001812.2 | mwghuman30K#A:10535 | -1.578112 | 0.000183356 | 0.000192131 | -4.258306 | 2275 | 19346.5 | 14107.25 | 4 |
| poly(A) polymerase beta (testis specific) (PAPOLB), mRNA | NP_064529.4 | NM_020144.4 | mwghuman30K#A:00034 | -1.533242 | 0.000179394 | 0.000311603 | -4.111646 | 2284 | 24777 | 23772.75 | 1 |
| oligonucleotide /oligosaccharide-binding fold containing 1 (OBFC1), mRNA | NP_079204.1 | NM_024928.3 | mwghuman30K#A:07366 | -1.597262 | 0.000151906 | 0.00015005 | -4.339099 | 2292 | 15940.5 | 11655 | 4 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| tripartite motif-containing 10 (TRIM10), transcript variant 1, mRNA | NP_006769.1 | NM_006778.2 | mwghuman3 0K#A:10515 | -1.750912 | 5.52205E-05 | 0.000135784 | -4.621742 | 2296.5 | 4089.5 | 1565.5 | 0 |
| Rap2-binding protein 9 (RPIB9), mRNA | NP_612147.1 | NM_138290.1 | mwghuman3 0K#B:7696 | -1.451227 | 1.03873E-06 | 1.37651E-05 | -5.068475 | 2297 | 24136.5 | 22036.5 | 1 |
| fksg17 | | NM_032031 | mwghuman3 0K#B:1656 | -1.576144 | 0.000141834 | 0.000233537 | -4.037961 | 2320.5 | 2050 | 1701.75 | 1 |
| G protein-coupled receptor 83 (GPR83), mRNA | NP_057624.2 | NM_016540.2 | mwghuman3 0K#A:05359 | -1.472466 | 6.54909E-05 | 0.000182916 | -3.811779 | 2322.5 | 18971.5 | 15879.25 | 0 |
| ensembl genscan prediction | | AC078987.9.1 35718.144151.1 | mwghuman3 0K#C:4632 | -1.300374 | 2.50018E-05 | 1.72268E-05 | -4.918105 | 2322.5 | 25018.5 | 21332.5 | |
| LIM homeobox 9 (LHX9), transcript variant 1, mRNA | NP_064589.2 | NM_020204.2 | mwghuman3 0K#B:8634 | -1.374971 | 4.6951E-06 | 9.24336E-06 | -5.312469 | 2333.5 | 16158 | 13872.25 | 0 |
| pellino homolog 1 (Drosophila) (PELI1), mRNA | NP_065702.2 | NM_020651.2 | mwghuman3 0K#A:10770 | -1.492094 | 8.8328E-06 | 8.23838E-06 | -5.23835 | 2336 | 22421.5 | 17524.5 | 7 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical LOC401500 (LOC401500), mRNA | XP_379629.1 | XM_379629.1 | mwghuman3 0K#B:6223 | -1.325858 | 2.27785E-05 | 4.12788E-05 | -4.402696 | 2336.5 | 26315 | 25320.25 | 0 |
| TSC22 domain family, member 3 (TSC22D3), transcript variant 2, mRNA | NP_004080.2 | NM_004089.3 | mwghuman3 0K#B:0462 | -1.491298 | 5.41371E-05 | 1.72268E-05 | -5.010311 | 2350.5 | 18693.5 | 13200.5 | 43 |
| G protein-coupled receptor 51 (GPR51), mRNA | NP_005449.5 | NM_005458.5 | mwghuman3 0K#A:04815 | -1.389185 | 0.0001017 06 | 2.98753E-05 | -4.845168 | 2361 | 3420 | 2489.25 | 0 |
| chromosome 10 open reading frame 61 (C10orf61), transcript variant 2, mRNA | NP_056446.1 | NM_015631.2 | mwghuman3 0K#B:3105 | -1.555923 | 0.0001770 95 | 0.000297 088 | -4.510054 | 2366.5 | 10134 | 8091.5 | 3 |
| jumonji domain containing 2C (JMJD2C), mRNA | NP_055876.1 | NM_015061.1 | mwghuman3 0K#B:8433 | -1.317474 | 6.41124E-05 | 0.000142 749 | -4.870495 | 2366.5 | 24516.5 | 22272.75 | 11 |
| zinc finger protein 547 (ZNF547), mRNA | NP_775902.2 | NM_173631.2 | mwghuman3 0K#B:6716 | -1.63256 | 0.0002511 74 | 0.000257 25 | -3.984452 | 2370 | 19484 | 19537 | 2 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein FLJ20032 (FLJ20032), mRNA | NP_060098.2 | NM_017628.2 | mwghuman3 0k#B:2068 | -1.74414 | 6.61052E-05 | 0.000105 506 | -4.166213 | 2374 | 15233.5 | 9767.75 | 16 |
| ensembl genscan prediction | | AC064877.3.1 21131.166993 .1 | mwghuman3 0k#C:7466 | -1.319284 | 4.28953E-05 | 2.03519E-05 | -4.802131 | 2374 | 27348 | 26740.25 | |
| ensembl genscan prediction | | AC027755.2.8 1287.97090.1 | mwghuman3 0k#C:3411 | -1.439071 | 0.0001259 01 | 0.000331 474 | -4.145868 | 2378.5 | 14385.5 | 10781.5 | |
| KIAA0690 (KIAA0690), mRNA | NP_055994.1 | NM_015179.2 | mwghuman3 0k#B:7202 | -1.642414 | 0.0001739 36 | 0.000433 377 | -4.08872 | 2380 | 14459 | 11844.25 | 10 |
| SH3 domain binding glutamic acid-rich protein like 2 (SH3BGRL2), mRNA | NP_113657.1 | NM_031469.1 | mwghuman3 0k#B:1794 | -1.995457 | 0.0002796 76 | 0.000376 568 | -4.033794 | 2381 | 9893.5 | 6985.75 | 3 |
| cdna: flj21394 fis clone col03536 unnamed protein product | | AK025047 | mwghuman3 0k#B:2580 | -2.258109 | 0.0004473 76 | 0.000359 234 | -4.071961 | 2387.5 | 17288 | 11926.75 | 0 |
| hypothetical protein xp_039231 loc91565 | | XM_039231 | mwghuman3 0k#B:6431 | -1.337232 | 2.70835E-05 | 0.000174 117 | -4.141157 | 2398 | 24099.5 | 20885 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| GPI anchored molecule like protein (GML), mRNA | NP_002057.1 | NM_002066.1 | mwghuman3 0K#A:02108 | -1.438045 | 0.0000724 93 | 0.000129 14 | -4.162956 | 2405 | 16818 | 14265.75 | 0 |
| small nuclear RNA activating complex, polypeptide 5, 19kDa (SNAPC5), mRNA | NP_006040.1 | NM_006049.1 | mwghuman3 0K#B:0945 | -1.323754 | 1.74702E-05 | 0.000184 787 | -4.006319 | 2444 | 17556.5 | 17969.25 | 6 |
| ensembl genscan prediction | | AC027689.10.1.180573.5 | mwghuman3 0K#C:9758 | -1.644263 | 0.0002550 65 | 2.98753E-05 | -3.674603 | 2451 | 16829.5 | 10684.25 | |
| mitochondrial tumor suppressor 1 (MTUS1), nuclear gene encoding mitochondrial protein, transcript variant 1, mRNA | NP_0010019 24.1 | NM_0010019 24.1 | mwghuman3 0K#B:7775 | -1.715161 | 0.0003036 63 | 0.000269 936 | -4.435392 | 2461.5 | 17489 | 15873 | 0 |
| ensembl genscan prediction | | AL049829.4.1.196292.3 | mwghuman3 0K#C:4548 | -1.402914 | 1.70061E-06 | 2.49927E-06 | -5.01844 | 2471 | 28131 | 26784 | |
| ensembl genscan prediction | | AC084842.1.7903.10639.1 | mwghuman3 0K#C:7638 | -1.400793 | 0.0008120 94 | 7.36585E-05 | -5.107784 | 2475.5 | 14235.5 | 11061.25 | |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| SAFB-like, transcription modulator (SLTM), transcript variant 1, mRNA | NP_079031.2 | NM_024755.2 | mwghuman30K#B:2154 | -1.309539 | 2.00445E-05 | 0.000122803 | -4.680439 | 2477.5 | 12490 | 12280 | 12 |
| guanine nucleotide binding protein (G protein), alpha activating activity polypeptide, olfactory type (GNAL), transcript variant 2, mRNA | NP_002062.1 | NM_002071.1 | mwghuman30K#A:06286 | -1.836112 | 0.00030026 | 0.000498109 | -4.10637 | 2478 | 19959 | 16690.75 | 0 |
| similar to cg14182 product loc146175 | | XM_085352 | mwghuman30K#B:7365 | -1.746066 | 0.000194923 | 0.000433377 | -3.812815 | 2487 | 14791.5 | 9814.5 | |
| PH domain and leucine rich repeat protein phosphatase (PHLPP), mRNA | NP_919431.1 | NM_194449.1 | mwghuman30K#B:2242 | -2.043619 | 0.000307945 | 0.000498109 | -4.006924 | 2500 | 15125 | 10009.75 | 7 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| autism susceptibility candidate 2 (AUTS2), mRNA | NP_056385.1 | NM_015570.1 | mwghuman3 0K#B:0110 | -1.807633 | 0.0003692 99 | 0.000382 814 | -4.213775 | 2503 | 18404 | 14412.75 | 8 |
| hypothetical protein xp_097338 loc147909 | | XM_097338 | mwghuman3 0K#B:5652 | -1.428873 | 1.32234E-06 | 2.67916E-05 | -4.387947 | 2513 | 4388 | 2991.75 | |
| leucine-rich repeat-containing G protein-coupled receptor 4 (LGR4), mRNA | NP_060960.1 | NM_018490.1 | mwghuman3 0K#A:06106 | -1.519205 | 7.81416E-05 | 0.000122 803 | -3.810559 | 2514.5 | 21417.5 | 19684 | 2 |
| ensembl prediction | | ENSG000001 13407 | mwghuman3 0K#C:2560 | -1.740805 | 1.93346E-05 | 9.52811E-05 | -4.388894 | 2525 | 8797.5 | 6359.5 | |
| programmed cell death 1 (PDCD1), mRNA | NP_005009.1 | NM_005018.1 | mwghuman3 0K#B:9147 | -1.519488 | 1.50412E-06 | 3.41028E-06 | -5.713059 | 2537 | 8575 | 7118.5 | 0 |
| cadherin 20, type 2 (CDH20), mRNA | NP_114097.2 | NM_031891.2 | mwghuman3 0K#B:7584 | -1.393019 | 1.91884E-05 | 2.73302E-05 | -4.362445 | 2538 | 15588 | 12275.75 | 0 |

Figure 6 (cont)

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| glycine dehydrogenase (decarboxylating; glycine decarboxylase, glycine cleavage system protein P) (GLDC), mRNA | NP_000161.1 | NM_000170.1 | mwghuman3 0K#B:8959 | -1.405054 | 9.33312E-05 | 0.00011676 | -4.398207 | 2542.5 | 6039 | 4550.5 | 1 |
| protease, serine, 35 (PRSS35), mRNA | NP_699193.1 | NM_153362.1 | mwghuman3 0K#B:3364 | -1.451818 | 0.000237039 | 0.00025725 | -4.319803 | 2545 | 16909 | 14109 | 0 |
| ensembl genscan prediction | | AC008134.3.1.175132.1 | mwghuman3 0K#C:3643 | -1.601839 | 0.00037884 | 0.000286633 | -4.042534 | 2545 | 27071.5 | 25825 | 0 |
| ATP-binding cassette, sub-family A (ABC1), member 12 (ABCA12), transcript variant 1, mRNA | NP_775099.2 | NM_173076.2 | mwghuman3 0K#B:3505 | -1.653773 | 0.000237178 | 0.000475592 | -3.927921 | 2561.5 | 19931 | 18593.5 | 0 |
| suppressor of hairy wing homolog 3 (Drosophila) (SUHW3), mRNA | NP_060136.1 | NM_017666.2 | mwghuman3 0K#B:2904 | -1.678106 | 0.000186359 | 0.000546156 | -3.864729 | 2568 | 17527 | 15364.5 | 1 |

Figure 6 (cont)

| Gene name/symbol | protein accession | mRNA ref seq accession | median fold change | rank score | tumour issue median intensity rank | non-malignant tissue median intensity rank | blood EST number |
|---|---|---|---|---|---|---|---|
| hypothetical protein FLJ21511 (FLJ21511), mRNA | NP_079363.1 | NM_025087.1 | -2.080908 | 68 | 14455 | 9272.5 | 0 |
| paired box gene 8 (PAX8), transcript variant PAX8A, mRNA | NP_003457.1 | NM_003466.3 | -1.961896 | 82 | 19419 | 12999.5 | 0 |
| UPF3 regulator of nonsense transcripts homolog A (yeast) (UPF3A), transcript variant 1, mRNA | NP_075387.1 | NM_023011.2 | -3.84007 | 96.5 | 5663.5 | 1825 | 0 |
| leukotriene B4 12-hydroxydehydrogenase (LTB4DH), mRNA | NP_036344.1 | NM_012212.2 | -5.034613 | 122.5 | 11340.5 | 3138 | 0 |
| RAB11 family interacting protein 2 (class I) (RAB11FIP2), mRNA | NP_055719.1 | NM_014904.1 | -1.993629 | 156 | 19636.5 | 12951 | 0 |
| TSC22 domain family, member 1 (TSC22D1), transcript variant 2, mRNA | NP_006013.1 | NM_006022.2 | -2.133065 | 156.5 | 8415 | 6130 | 1 |
| sulfite oxidase (SUOX), nuclear gene encoding mitochondrial protein, transcript variant 1, mRNA | NP_000447.2 | NM_000456.2 | -1.622803 | 223 | 11312.5 | 8789.5 | 0 |
| tetratricopeptide repeat domain 21A (TTC21A), mRNA | NP_665698.1 | NM_145755.1 | -2.976809 | 225 | 8375.5 | 3870.5 | 1 |
| synaptotagmin-like 2 (SYTL2), transcript variant b, mRNA | NP_115755.2 | NM_032379.3 | -2.343357 | 342 | 19920 | 12053.5 | 0 |
| wingless-type MMTV integration site family, member 2B (WNT2B), transcript variant WNT-2B1, mRNA | NP_004176.2 | NM_004185.2 | -10.745275 | 501 | 10716 | 2016.25 | 0 |
| protocadherin gamma subfamily A, 12 (PCDHGA12), transcript variant 1, mRNA | NP_003726.1 | NM_003735.2 | -2.070447 | 511 | 2537 | 1931.5 | 0 |
| olfactory receptor, family 1, subfamily D, member 5 (OR1D5), mRNA | NP_055381.1 | NM_014566.1 | -1.640751 | 539.5 | 1644 | 1134 | 0 |
| G protein-coupled receptor 126 (GPR126), transcript variant b1, mRNA | NP_940971.1 | NM_198569.1 | -2.181735 | 549 | 15965.5 | 8040.75 | 0 |
| ubiquitin specific peptidase 9, Y-linked (fat facets-like, Drosophila) (USP9Y), mRNA | NP_004645.2 | NM_004654.3 | -1.584065 | 587 | 10035.5 | 7858.25 | 1 |

Figure 7

| Gene name/symbol | protein accession | mRNA ref seq accession | median fold change | rank score | tumour issue median intensity rank | non-malignant tissue median intensity rank | blood EST number |
|---|---|---|---|---|---|---|---|
| chromosome 11 open reading frame 1 (C11orf1), mRNA | NP_073598.1 | NM_022761.1 | -1.81726 | 673.5 | 12025.5 | 9585.25 | 0 |
| BCL2-associated athanogene (BAG1), mRNA | NP_004314.3 | NM_004323.3 | -2.525417 | 776 | 9031 | 4503.5 | 1 |
| family with sequence similarity 44, member B (FAM44B), mRNA | NP_612378.1 | NM_138369.1 | -1.357114 | 942.5 | 15308.5 | 13004.75 | 1 |
| fibroblast growth factor receptor 4 (FGFR4), transcript variant 2, mRNA | NP_075252.2 | NM_022963.2 | -2.638426 | 1087.5 | 17096 | 9762.5 | 0 |
| thyroid transcription factor 1 (TITF1), mRNA | NP_003308.1 | NM_003317.3 | -1.466987 | 1124.5 | 2139 | 1026.25 | 0 |
| VprBP protein (VprBP), mRNA | NP_055518.1 | NM_014703.1 | -1.720326 | 1178 | 17312.5 | 14031 | 0 |
| empty spiracles homolog 2 (Drosophila) (EMX2), mRNA | NP_004089.1 | NM_004098.2 | -1.745086 | 1199.5 | 19380 | 10749.25 | 0 |
| homeo box D8 (HOXD8), mRNA | NP_062458.1 | NM_019558.2 | -1.41555 | 1206 | 9672.5 | 7512.25 | 0 |
| zinc finger protein 626 (ZNF626), mRNA | NP_660340.1 | NM_145297.2 | -1.773183 | 1266 | 14806.5 | 10341 | 1 |
| ring finger protein 44 (RNF44), mRNA | NP_055716.1 | NM_014901.4 | -1.353366 | 1292 | 6288.5 | 4664.5 | 1 |
| pyrimidinergic receptor P2Y, G-protein coupled, 4 (P2RY4), mRNA | NP_002556.1 | NM_002565.3 | -1.732075 | 1309 | 18307 | 12139.5 | 0 |
| similar to hypothetical protein (LOC440804), mRNA | XP_036936.3 | XM_036936.3 | -4.049648 | 1332 | 3647 | 996.5 | 0 |
| chromosome 20 open reading frame 152 (C20orf152), mRNA | NP_543024.1 | NM_080834.1 | -1.948612 | 1349 | 10775 | 8652.5 | 0 |
| follistatin-like 4 (FSTL4), mRNA | NP_055897.1 | NM_015082.1 | -1.544042 | 1405.5 | 17051 | 12319 | 0 |
| chromosome 14 open reading frame 168 (C14orf168), mRNA | NP_113615.1 | NM_031427.1 | -1.512002 | 1414 | 15738 | 14705.75 | 1 |
| kallikrein 8 (neuropsin/ovasin) (KLK8), transcript variant 2, mRNA | NP_653088.1 | NM_144505.1 | -2.091505 | 1449.5 | 8391 | 6488 | 0 |
| leucine zipper, down-regulated in cancer 1-like (LDOC1L), mRNA | NP_115663.2 | NM_032287.2 | -1.501021 | 1454.5 | 16509.5 | 14157 | 0 |
| hypothetical protein MGC11242 (MGC11242), mRNA | NP_077296.1 | NM_024320.2 | -1.527839 | 1463.5 | 17565 | 13134.5 | 0 |
| KIAA1274 (KIAA1274), mRNA | NP_055246.1 | NM_014431.1 | -1.41942 | 1488.5 | 8059 | 5065 | 0 |
| hypothetical LOC401510 (LOC401510), mRNA | XP_376843.2 | XM_376843.2 | -1.402922 | 1504 | 13882.5 | 11233.25 | 0 |

Figure 7 (cont)

| Gene name/symbol | protein accession | mRNA ref seq accession | median fold change | rank score | tumour issue median intensity rank | non-malignant tissue median intensity rank | blood EST number |
|---|---|---|---|---|---|---|---|
| plastin 1 (I isoform) (PLS1), mRNA | NP_002661.1 | NM_002670.1 | -1.626206 | 1509.5 | 20943 | 14040.5 | 1 |
| zinc finger, DHHC-type containing 2 (ZDHHC2), mRNA | NP_057437.1 | NM_016353.2 | -1.588633 | 1536 | 13684.5 | 10087.5 | 0 |
| cone-rod homeobox (CRX), mRNA | NP_000545.1 | NM_000554.2 | -3.022299 | 1548 | 16588.5 | 7500.5 | 0 |
| PHD finger protein 23 (PHF23), mRNA | NP_077273.1 | NM_024297.1 | -1.398461 | 1657.5 | 10656.5 | 9355.75 | 0 |
| nasopharyngeal carcinoma associated gene protein-8 (NAG8), mRNA | NP_055226.1 | NM_014411.2 | -1.388055 | 1660 | 15731.5 | 12161 | 0 |
| HERV-H LTR-associating 3 (HHLA3), transcript variant 3, mRNA | NP_001031722.1 | NM_001036645.1 | -2.043346 | 1759 | 13925.5 | 11798 | 0 |
| fibronectin leucine rich transmembrane protein 3 (FLRT3), transcript variant 1, mRNA | NP_037413.1 | NM_013281.2 | -4.204569 | 1770 | 18156 | 9231.25 | 0 |
| cell division cycle associated 7 (CDCA7), transcript variant 1, mRNA | NP_114148.2 | NM_031942.3 | -1.959598 | 1788 | 14826 | 12577.25 | 1 |
| pyruvate dehydrogenase kinase, isozyme 4 (PDK4), mRNA | NP_002603.1 | NM_002612.2 | -1.735687 | 1911.5 | 18067 | 13997.25 | 1 |
| leucine rich repeat and sterile alpha motif containing 1 (LRSAM1), transcript variant 1, mRNA | NP_612370.3 | NM_138361.3 | -2.034574 | 1959.5 | 7671.5 | 4421.75 | 1 |
| guanine nucleotide binding protein (G protein), alpha inhibiting activity polypeptide 1 (GNAI1), mRNA | NP_002060.4 | NM_002069.4 | -1.631361 | 2003 | 16803.5 | 14082 | 1 |
| cerebral endothelial cell adhesion molecule 1 (CEECAM1), mRNA | NP_057258.2 | NM_016174.3 | -1.516413 | 2014 | 16662.5 | 13757.75 | 0 |
| hypothetical protein FLJ22965 (FLJ22965), mRNA | NP_071384.1 | NM_022101.2 | -1.903469 | 2041.5 | 2596 | 2337 | 0 |
| chromosome 9 open reading frame 102 (C9orf102), transcript variant 1, mRNA | NP_064592.1 | NM_020207.2 | -1.369819 | 2049 | 16457.5 | 13970 | 0 |
| pleckstrin and Sec7 domain containing 3 (PSD3), transcript variant 1, mRNA | NP_056125.2 | NM_015310.2 | -1.395381 | 2072 | 14023 | 13223.25 | 1 |
| zinc finger, FYVE domain containing 21 (ZFYVE21), mRNA | NP_076976.1 | NM_024071.2 | -1.579562 | 2094 | 2994.5 | 2740.25 | 0 |
| forkhead box E1 (thyroid transcription factor 2) (FOXE1), mRNA | NP_004464.2 | NM_004473.3 | -1.678652 | 2107 | 7269 | 5293.75 | 0 |

Figure 7 (cont)

| Gene name/symbol | protein accession | mRNA ref seq accession | median fold change | rank score | tumour tissue median intensity rank | non-malignant tissue median intensity rank | blood EST number |
|---|---|---|---|---|---|---|---|
| Myc-induced mitochondria protein (mimitin), mRNA | NP_777549.1 | NM_174889.2 | -1.474873 | 2151.5 | 9215 | 7030.25 | 1 |
| similar to developmental pluripotency associated 5; embryonal stem cell specific gene 1 (LOC341912), mRNA | XP_292301.3 | XM_292301.3 | -1.639786 | 2155 | 18581.5 | 12815.25 | 1 |
| hepcidin antimicrobial peptide (HAMP), mRNA | NP_066998.1 | NM_021175.2 | -1.279742 | 2205.5 | 3722.5 | 3385.25 | 0 |
| hypothetical protein BC009862 (LOC90113), mRNA | XP_291077.3 | XM_291077.3 | -1.769275 | 2221.5 | 6261.5 | 5176 | 0 |
| tripartite motif-containing 10 (TRIM10), transcript variant 1, mRNA | NP_006769.1 | NM_006778.2 | -1.750912 | 2296.5 | 4089.5 | 1565.5 | 0 |
| fksg17 fksg17 | | NM_032031 | -1.576144 | 2320.5 | 2050 | 1701.75 | 1 |
| LIM homeobox 9 (LHX9), transcript variant 1, mRNA | NP_064589.2 | NM_020204.2 | -1.374971 | 2333.5 | 16158 | 13872.25 | 0 |
| G protein-coupled receptor 51 (GPR51), mRNA | NP_005449.5 | NM_005458.5 | -1.389185 | 2361 | 3420 | 2489.25 | 0 |
| cdna: flj21394 fis clone col03536 unnamed protein product | | AK025047 | -2.258109 | 2387.5 | 17288 | 11926.75 | 0 |
| GPI anchored molecule like protein (GML), mRNA | NP_002057.1 | NM_002066.1 | -1.438045 | 2405 | 16818 | 14265.75 | 0 |
| programmed cell death 1 (PDCD1), mRNA | NP_005009.1 | NM_005018.1 | -1.519488 | 2537 | 8575 | 7118.5 | 0 |
| cadherin 20, type 2 (CDH20), mRNA | NP_114097.2 | NM_031891.2 | -1.393019 | 2538 | 15588 | 12275.75 | 0 |
| glycine dehydrogenase (decarboxylating; glycine decarboxylase, glycine cleavage system protein P) (GLDC), mRNA | NP_000161.1 | NM_000170.1 | -1.405054 | 2542.5 | 6039 | 4550.5 | 1 |
| protease, serine, 35 (PRSS35), mRNA | NP_699193.1 | NM_153362.1 | -1.451818 | 2545 | 16909 | 14109 | 0 |

Figure 7 (cont)

|  | No specific diagnosis (N=164) | Non-malignant disease (N=255) | TCC (N=66) | Overall (N=485) |
| --- | --- | --- | --- | --- |
| Country, n (%) | | | | |
| New Zealand | 147 (89.6) | 239 (93.7) | 64 (97.0) | 450 (92.8) |
| Australia | 17 (10.4) | 16 (6.27) | 2 (3.0) | 35 (7.2) |
| Age, median (IQ range) | 64 (55, 75) | 71 (62, 78) | 71 (63, 80) | 69 (59, 77) |
| Sex, n (%) | | | | |
| Male | 112 (68.3) | 216 (84.7) | 61 (92.4) | 389 (80.2) |
| Female | 52 (31.7) | 39 (15.3) | 5 (7.5) | 96 (19.8) |
| Ethnicity, n (%) | | | | |
| European | 133 (81.1) | 228 (89.4) | 62 (93.9) | 423 (87.2) |
| Maori | 15 (9.1) | 17 (6.7) | 1 (1.5) | 33 (6.8) |
| Other | 16 (9.8) | 10 (3.9) | 3 (4.5) | 29 (6.0) |
| Haematuria, n (%) | | | | |
| Years since onset | | | | |
| <6 mths | 131 (79.9) | 198 (77.6) | 57 (86.4) | 386 (79.6) |
| 6 mths-1 yr | 11 (6.7) | 25 (9.8) | 6 (9.1) | 42 (8.7) |
| 1-2 yrs | 11 (6.7) | 18 (7.1) | 3 (4.5) | 32 (6.6) |
| 3-5 yrs | 5 (3.0) | 5 (2.0) | 0 (0.0) | 10 (2.1) |
| > 5 yrs | 6 (3.7) | 9 (3.5) | 0 (0.0) | 15 (3.1) |
| End of last episode | | | | |
| 1-7 days | 9 (5.5) | 26 (10.2) | 20 (30.3) | 55 (11.3) |
| 8-28 days | 14 (8.5) | 27 (10.6) | 13 (19.7) | 54 (11.1) |
| 1-2 Months | 60 (36.6) | 86 (33.7) | 14 (21.2) | 160 (33.0) |
| 3-6 Months | 70 (42.7) | 100 (39.2) | 19 (28.8) | 189 (39.0) |
| > 6 months | 11 (6.7) | 15 (5.9) | 0 (0.0) | 26 (5.4) |
| Unknown | 0 (0.0) | 1 (0.4) | 0 (0.0) | 1 (0.2) |
| Frequency | | | | |
| <=1 per day | 104 (63.4) | 160 (62.7) | 30 (45.5) | 294 (60.6) |
| >1 per day | 59 (36.0) | 95 (37.3) | 36 (54.5) | 190 (39.2) |
| Unknown | 1 (0.6) | 0 (0.0) | 0 (0.0) | 1 (0.2) |
| Smoking status, n (%) | | | | |
| Current smoker | 34 (20.7) | 28 (11.0) | 14 (21.2) | 76 (15.7) |
| Ex-smoker | 66 (40.2) | 114 (44.7) | 35 (53.0) | 215 (44.3) |
| Never smoker | 64 (39.0) | 113 (44.3) | 17 (25.8) | 194 (40.0) |

Figure 9

| Test | Overall Sensitivity | Overall Specificity |
|---|---|---|
| uRNA-D | 62.1% (49.3 73.8) | 85.2% (fixed) |
| NMP22 Elisa | 50.0% (37.4, 62.6) | 88.0% (84.6, 91.0) |
| NMP22 BladderChek | 37.9% (26.2, 50.7) | 96.4% (94.2, 98.0) |
| Cytology* | 56.1% (43.3, 68,3) | 94.5 (91.9, 96.5) |
| Five Genes (including IL8BRb)† | 81.8% | 85.1% (fixed) |
| Five Genes (including IL8BRb)† (90% specificity) | 72.7% | 89.9% (fixed) |

* Included in determination of TCC for some patients
† Determined on study data so confidence intervals are not presented

Figure 10

Fig 11a.
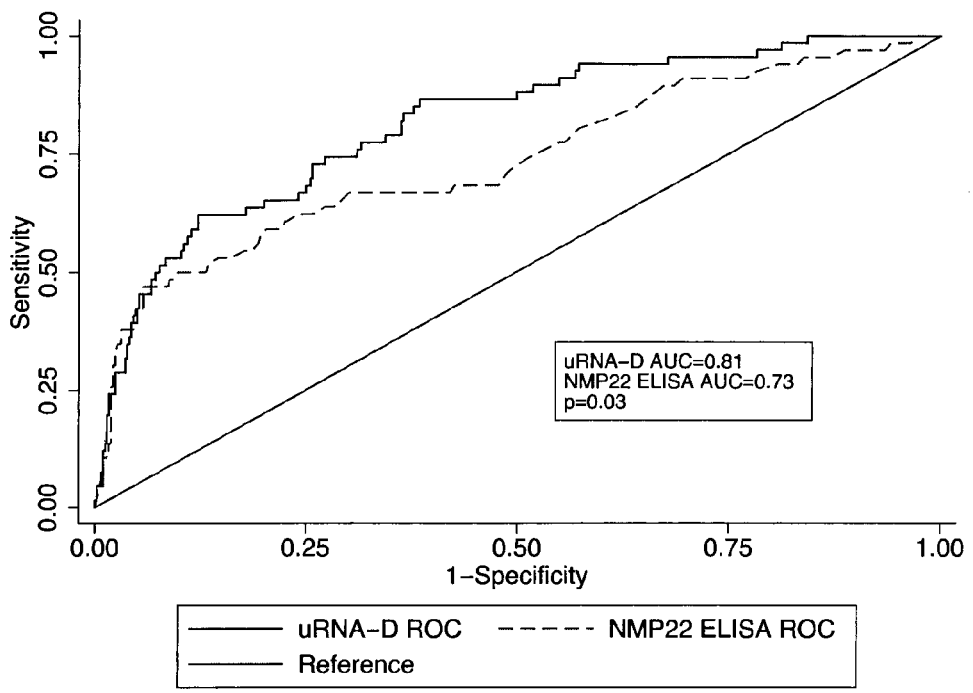
Fig 11b.
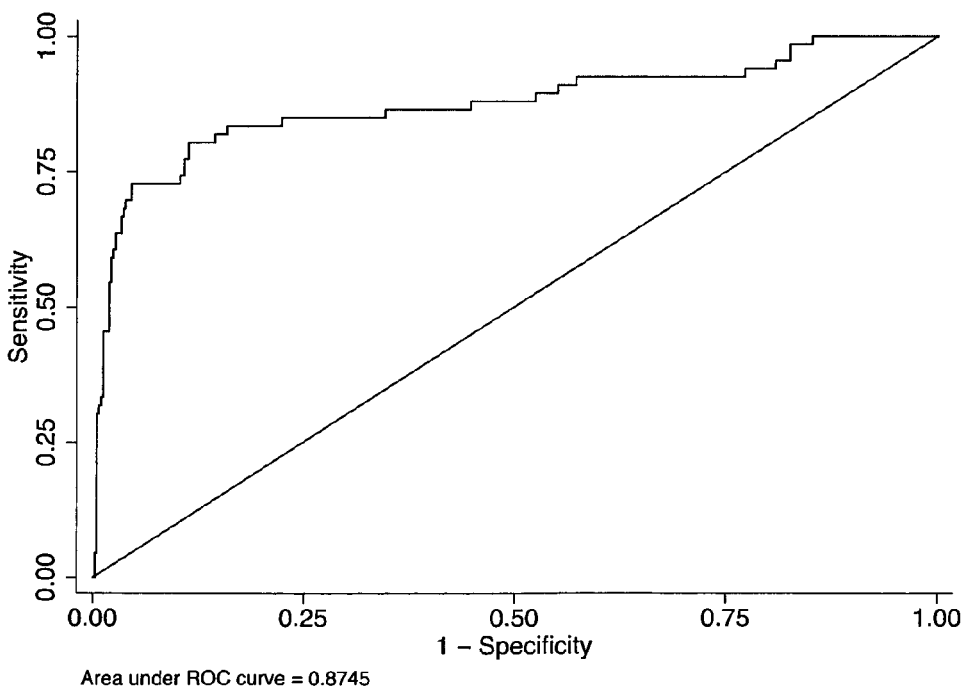
Area under ROC curve = 0.8745
Figure 11

| | Cytology | NMP22 Elisa | BladderChek | uRNA-D | Five Markers |
|---|---|---|---|---|---|
| Stage (n=66) | n, % (95% CI) | n, % (95% CI) | n, % (95% CI) | n, % (95% CI) | n, % |
| Tis (n=2) | 2, 100% (16, 100) | 0, 0% (0, 84) | 0, 0% (0, 84) | 1, 50% (1, 99) | 2, 100% |
| Ta (n=37) | 13, 35% (20, 53) | 13, 35% (20, 53) | 14, 38% (22, 55) | 15, 41% (25, 58) | 25, 68% |
| T1 (n=16) | 11, 69% (41, 89) | 12, 75% (48, 93) | 8, 50% (25, 75) | 15, 94 (70, 100) | 16, 100% |
| T2 (n=9) | 9, 100% (66, 100) | 6, 67% (30, 93) | 2, 22% (3, 60) | 9, 100 (66, 100) | 9, 100% |
| ≥T3 (n=2) | 2, 100% (16, 100) | 2, 100% (16, 100) | 1, 50% (11, 99) | 1, 50% (1.3, 99) | 2, 100% |
| Grade WHO 73 (n=65) | | | | | $p^*=0.019$ |
| 1 (n=3) | 1, 33% (1, 91) | 1, 33% (1, 91) | 1, 33% (1, 91)) | 1, 33% (1, 91)) | 1, 33% |
| 2 (n=38) | 17, 44% (29, 62) | 15, 39% (24, 57) | 13, 34% (20, 51) | 21, 55% (38, 71) | 29, 76% |
| 3 (n=24) | 19, 79% (58, 93) | 17, 71% (49, 87) | 11, 46% (26, 67) | 19, 79% (58, 93) | 23, 96% |
| Grade WHO ISUP 1998 (n=65) | | | | | $p^*=0.016$ |
| Low (n=32) | 9, 28% (14, 47) | 10, 31% (16, 50) | 13, 41% (24, 59) | 13, 41% (24, 59) | 22, 69% |
| Mixed (n=4) | 4, 100% (40, 100) | 3, 75% (19, 99) | 1, 25% (1, 81) | 4, 100 (40,100) | 4, 100% |
| High (n=29) | 24, 83% (64, 94) | 20, 69% (49, 85) | 11, 38% (21, 58) | 24, 83% (64, 94) | 28, 97% |
| Tumour location (n=66) | | | | | $p^*=0.012$ |
| Bladder (n=62) | 35, 56% (43, 69) | 30, 48% (35, 61) | 25, 40% (28. 54) | 39, 63% (50, 75) | 50, 81% |
| Up. tract (n=4) | 2, 50% (7, 93) | 3, 75% (19, 99) | 0, 0% (0, 60) | 2, 50% (7, 93) | 4, 100% |
| Multiplicity (n=66) | | | | | $p^*=0.33$ |
| Single (n=52) | 27, 52% (38. 66) | 23, 44% (30. 59) | 17, 33% (20, 47) | 30, 58% (43, 71) | 41, 79% |
| Multifocal (n=13) | 10, 77% (46, 95) | 10, 77% (46, 95) | 8, 62% (32, 86) | 11, 85% (55, 98) | 12, 92% |
| Microhaematuria (n=65) | | | | | $p^*=0.43$ |
| Yes (n=43) | 27, 63% (47, 77) | 27, 63% (47, 77) | 20, 47% (31, 62) | 31, 72% (56, 85) | 41, 95% |
| No (n=22) | 9, 41% (21, 64)) | 5, 23% (8, 45) | 4, 18% (5, 40) | 9, 41% (21, 64) | 12, 55% |
| Creatinine (n=55) | | | | | $p^*<0.0005$ |
| 0-4.3 (n=11) | 5, 45 (17, 77) | 3, 27% (6,61) | 4, 36% (11, 69) | 4, 36% (11, 69) | 7, 64% |
| 4.3-7.1 (n=14) | 9, 64% (35, 87) | 6, 43% (18,71) | 4, 29% (8, 58) | 8, 57% (29, 82) | 12, 86% |
| 7.1-11.2 (n=22) | 11, 50% (28. 72) | 14, 64% (41, 83) | 11, 50% (28. 72) | 16, 73% (50, 89) | 18, 82% |
| ≥11.2 (n=8) | 6, 75% (35, 97) | 3, 38% (9, 76) | 2, 25% (3, 65) | 6, 75% (35, 97) | 8, 100% |
| Sex (n=66) | | | | | $p^*=0.29$ |
| Male (n=61) | 35, 57% (44, 70) | 29, 48% (35, 61) | 23, 38% (26, 51) | 37, 61% (47, 73) | 49, 80% |
| Female (n=5) | 2, 40% (5, 85) | 4, 80% (28, 99) | 2, 40% (5, 85) | 4, 80% (28, 99) | 5, 100% |
| | | | | | $p^*=0.58$ |

*p-values from Fisher's exact test of association between each TCC characteristic and Cxbladder test result

Figure 12

| | Cytology | NMP22 Elisa | NMP22 BladderChek | uRNA-D* | Five Markers* |
|---|---|---|---|---|---|
| | n, % 95% CI | n, % 95% CI | n, % 95% CI | n, % | n,% |
| Diagnosis | | | | | |
| No diagnosis (n=164) | | | | | |
| | 154, 94% (89, 97) | 144, 88% (82, 92) | 160, 98% (94, 99) | 144, 88% | 144, 88% |
| Non-malignant diagnosis | | | | | |
| Benign prostatic hypertrophy/prostatitis (n=130) | | | | | |
| | 123, 95% (89, 98) | 117, 90.% (84, 95) | 127, 98% (93, 100) | 113, 87% | 109/128=85% |
| Cystitis/infection or inflammation of the urinary tract (n=39) | | | | | |
| | 36, 92% (79, 98) | 34, 87% (73, 96) | 34, 87% (73, 96) | 28, 72% | 32,.82% |
| Calculi (n=28) | | | | | |
| | 25, 89% (72, 98) | 23, 82% (63, 94) | 27, 96% (82, 100) | 20, 71% | 19, 68% |
| Haematuria secondary to warfarin (n=10) | | | | | |
| | 10, 100% (69, 100) | 9, 90% (55, 100) | 10, 100% (69, 100) | 8, 80% | 8, 80% |
| Other urological cancer (n=5) | | | | | |
| | 5, 100% (48, 100) | 4, 80% (28, 99) | 5, 100% (48, 100) | 5, 100% | 4, 80% |
| Microhaematuria (n=417) | | | | | $p^†=0.12$ |
| Yes n=99 | 87, 88% (80, 94) | 81, 82% (73, 89) | 91, 92% (85, 96) | 74, 75% | 73/97=75% |
| No n=318 | 307, 97% (94, 98) | 287, 90% (86, 93) | 311, 98% (96, 99) | 281, 88% | 279/317=88% |
| Creatinine (n=386) | | | | | $p^†=0.002$ |
| 0 – 4.3, n=97 | 95, 98% (93, 100) | 90, 93% (86, 97) | 95, 98% (93, 100) | 87, 90% | 83/96=86% |
| 4.3 – 7.1, n=94 | 92, 98% (93, 100) | 81, 86% (78, 92) | 90, 96% (89, 99) | 81, 86% | 84/93=90% |
| 7.1 – 11.2, n=92 | 79, 86% (77, 92) | 83, 90% (82, 95) | 90, 98% (92, 100) | 76, 83% | 76/92=83% |
| ≥11.2, n=103 | 101 98% (93, 100) | 91, 88% (81, 94) | 101, 98% (93, 100) | 88, 85% | 82/102=80% |
| Sex (n=419) | | | | | $p^†=0.32$ |
| Male n=328 | 311, 95% (92, 97) | 290, 88% (84, 92) | 316, 96% (94, 98) | 291, 89% | 280/325=86% |
| Female, n=91 | 85, 93% (86, 98) | 79, 87% (78, 93) | 88 97% (91, 99) | 65, 71% | 74/91=81% |
| | | | | | $p^†=0.25$ |

*overall specificity fixed at 85%

†p-value from Chi square test of association between each characteristic (diagnosis, microhaematuria, creatinine sex) and Cxbladder test result

Figure 13

| Model | LDA | | LogReg | | SVM | | KN5N | | TREE | |
|---|---|---|---|---|---|---|---|---|---|---|
| | -IL8Rb | +IL8Rb | -IL8Rb | +IL8Rb | -IL8Rb | +IL8Rb | -IL8Rb | +IL8Rb | -IL8Rb | +IL8Rb |
| MDK | 0.087 | 0.127 | 0.119 | 0.127 | 0.107 | 0.121 | 0.100 | 0.120 | 0.107 | 0.117 |
| CDC2 | 0.062 | 0.129 | 0.124 | 0.129 | 0.102 | 0.127 | 0.102 | 0.121 | 0.114 | 0.124 |
| IGFBP5 | 0.060 | 0.108 | 0.109 | 0.108 | 0.094 | 0.107 | 0.093 | 0.090 | 0.093 | 0.096 |
| HOXA13 | 0.058 | 0.094 | 0.094 | 0.094 | 0.082 | 0.084 | 0.075 | 0.071 | 0.078 | 0.075 |
| MDK + CDC2 | 0.124 | 0.134 | 0.124 | 0.133 | 0.115 | 0.131 | 0.109 | 0.128 | 0.107 | 0.111 |
| MDK + IGFBP5 | 0.122 | 0.129 | 0.121 | 0.129 | 0.125 | 0.133 | 0.111 | 0.122 | 0.107 | 0.107 |
| MDK + HOXA13 | 0.119 | 0.126 | 0.118 | 0.125 | 0.108 | 0.118 | 0.107 | 0.107 | 0.107 | 0.114 |
| CDC2 + IGFBP5 | 0.128 | 0.134 | 0.127 | 0.133 | 0.114 | 0.125 | 0.109 | 0.125 | 0.109 | 0.115 |
| CDC + HOXA13 | 0.122 | 0.128 | 0.123 | 0.129 | 0.103 | 0.125 | 0.116 | 0.108 | 0.113 | 0.123 |
| IGF + HOXA13 | 0.109 | 0.109 | 0.108 | 0.107 | 0.119 | 0.121 | 0.096 | 0.098 | 0.102 | 0.101 |
| MDK + CDC2 + IGFBP5 | 0.127 | 0.135 | 0.127 | 0.135 | 0.123 | 0.134 | 0.119 | 0.132 | 0.103 | 0.108 |
| MDK + CDC2 + HOXA13 | 0.125 | 0.133 | 0.125 | 0.134 | 0.109 | 0.127 | 0.113 | 0.122 | 0.104 | 0.111 |
| MDK + IGFBP5 + HOXA13 | 0.122 | 0.128 | 0.121 | 0.127 | 0.126 | 0.132 | 0.111 | 0.115 | 0.110 | 0.109 |
| CDC2 + IGFBP5 + HOXA13 | 0.129 | 0.136 | 0.131 | 0.136 | 0.126 | 0.131 | 0.117 | 0.114 | 0.108 | 0.111 |
| MDK+CDC2+IGFBP5+HOXA13 | 0.130 | 0.137 | 0.130 | 0.138 | 0.124 | 0.137 | 0.122 | 0.129 | 0.103 | 0.106 |

Area Under the ROC Curve (AUC) for False Positive Rate from 0.00 to 0.20

Figure 15a

| Model | LDA | LogReg | SVM | KN5N | TREE |
|---|---|---|---|---|---|
| MDK | 0.040 | 0.008 | 0.014 | 0.019 | 0.010 |
| CDC2 | 0.067 | 0.005 | 0.025 | 0.018 | 0.009 |
| IGFBP5 | 0.048 | -0.001 | 0.013 | -0.003 | 0.002 |
| HOXA13 | 0.036 | 0.000 | 0.001 | -0.004 | -0.003 |
| MDK + CDC2 | 0.009 | 0.009 | 0.015 | 0.019 | 0.005 |
| MDK + IGFBP5 | 0.007 | 0.007 | 0.008 | 0.011 | -0.000 |
| MDK + HOXA13 | 0.007 | 0.007 | 0.010 | 0.000 | 0.007 |
| CDC2 + IGFBP5 | 0.007 | 0.006 | 0.012 | 0.016 | 0.006 |
| CDC + HOXA13 | 0.006 | 0.006 | 0.022 | -0.007 | 0.010 |
| IGF + HOXA13 | 0.000 | -0.001 | 0.002 | 0.002 | -0.000 |
| MDK + CDC2 + IGFBP5 | 0.009 | 0.008 | 0.012 | 0.013 | 0.004 |
| MDK + CDC2 + HOXA13 | 0.008 | 0.008 | 0.018 | 0.009 | 0.006 |
| MDK + IGFBP5 + HOXA13 | 0.006 | 0.006 | 0.006 | 0.004 | -0.001 |
| CDC2 + IGFBP5 + HOXA13 | 0.006 | 0.006 | 0.005 | -0.003 | 0.004 |
| MDK+CDC2+IGFBP5+HOXA13 | 0.007 | 0.007 | 0.013 | 0.007 | 0.002 |

Gain in AUC (over FPR from 0.0 to 0.2)

Figure 15b

| a | Model | LDA | | LogReg | | SVM | | KN5N | | TREE | |
|---|---|---|---|---|---|---|---|---|---|---|---|
| | | -IL8Rb | +IL8Rb | -IL8Rb | +IL8Rb | -IL8Rb | +IL8Rb | -IL8Rb | +IL8Rb | -IL8Rb | +IL8Rb |
| | MDK | 0.721 | 0.734 | 0.734 | 0.734 | 0.594 | 0.672 | 0.531 | 0.781 | 0.625 | 0.688 |
| | CDC2 | 0.753 | 0.734 | 0.750 | 0.734 | 0.562 | 0.703 | 0.750 | 0.734 | 0.672 | 0.703 |
| | IGFBP5 | 0.657 | 0.703 | 0.688 | 0.703 | 0.516 | 0.625 | 0.516 | 0.656 | 0.656 | 0.609 |
| | HOXA13 | 0.486 | 0.609 | 0.625 | 0.609 | 0.484 | 0.469 | 0.406 | 0.375 | 0.547 | 0.578 |
| | MDK + CDC2 | 0.734 | 0.750 | 0.734 | 0.750 | 0.641 | 0.719 | 0.734 | 0.750 | 0.672 | 0.641 |
| | MDK + IGFBP5 | 0.734 | 0.734 | 0.734 | 0.734 | 0.703 | 0.781 | 0.688 | 0.766 | 0.625 | 0.625 |
| | MDK + HOXA13 | 0.719 | 0.719 | 0.734 | 0.719 | 0.609 | 0.641 | 0.703 | 0.719 | 0.609 | 0.672 |
| | CDC2 + IGFBP5 | 0.766 | 0.781 | 0.766 | 0.781 | 0.609 | 0.719 | 0.688 | 0.781 | 0.672 | 0.688 |
| | CDC + HOXA13 | 0.750 | 0.734 | 0.750 | 0.734 | 0.562 | 0.703 | 0.703 | 0.688 | 0.656 | 0.703 |
| | IGF + HOXA13 | 0.703 | 0.703 | 0.672 | 0.672 | 0.719 | 0.750 | 0.500 | 0.641 | 0.688 | 0.672 |
| | MDK + CDC2 + IGFBP5 | 0.766 | 0.766 | 0.766 | 0.766 | 0.688 | 0.766 | 0.734 | 0.797 | 0.656 | 0.625 |
| | MDK + CDC2 + HOXA13 | 0.734 | 0.734 | 0.734 | 0.734 | 0.609 | 0.688 | 0.766 | 0.703 | 0.656 | 0.656 |
| | MDK + IGFBP5 + HOXA13 | 0.734 | 0.719 | 0.734 | 0.719 | 0.719 | 0.766 | 0.750 | 0.703 | 0.656 | 0.656 |
| | CDC2 + IGFBP5 + HOXA13 | 0.797 | 0.797 | 0.812 | 0.781 | 0.719 | 0.750 | 0.734 | 0.688 | 0.672 | 0.672 |
| | MDK+CDC2+IGFBP5+HOXA13 | 0.766 | 0.781 | 0.781 | 0.797 | 0.703 | 0.766 | 0.766 | 0.719 | 0.656 | 0.641 |

Sensitivity at Specificity: Sp.80

Figure 16a b

| Model | LDA | | LogReg | | SVM | | KN5N | | TREE | |
|---|---|---|---|---|---|---|---|---|---|---|
| | -IL8Rb | +IL8Rb | -IL8Rb | +IL8Rb | -IL8Rb | +IL8Rb | -IL8Rb | +IL8Rb | -IL8Rb | +IL8Rb |
| MDK | 0.657 | 0.719 | 0.672 | 0.719 | 0.578 | 0.641 | 0.531 | 0.609 | 0.609 | 0.672 |
| CDC2 | 0.481 | 0.703 | 0.719 | 0.703 | 0.531 | 0.688 | 0.500 | 0.625 | 0.672 | 0.703 |
| IGFBP5 | 0.595 | 0.641 | 0.625 | 0.656 | 0.516 | 0.625 | 0.516 | 0.484 | 0.562 | 0.578 |
| HOXA13 | 0.462 | 0.594 | 0.562 | 0.562 | 0.469 | 0.469 | 0.406 | 0.375 | 0.500 | 0.406 |
| MDK + CDC2 | 0.688 | 0.734 | 0.688 | 0.734 | 0.641 | 0.688 | 0.562 | 0.672 | 0.641 | 0.641 |
| MDK + IGFBP5 | 0.703 | 0.719 | 0.703 | 0.719 | 0.703 | 0.781 | 0.562 | 0.766 | 0.609 | 0.609 |
| MDK + HOXA13 | 0.656 | 0.688 | 0.656 | 0.688 | 0.594 | 0.641 | 0.562 | 0.516 | 0.594 | 0.625 |
| CDC2 + IGFBP5 | 0.750 | 0.766 | 0.750 | 0.766 | 0.609 | 0.688 | 0.578 | 0.641 | 0.625 | 0.641 |
| CDC + HOXA13 | 0.719 | 0.703 | 0.719 | 0.703 | 0.547 | 0.688 | 0.594 | 0.547 | 0.656 | 0.703 |
| IGF + HOXA13 | 0.641 | 0.641 | 0.641 | 0.641 | 0.688 | 0.719 | 0.500 | 0.484 | 0.609 | 0.609 |
| MDK + CDC2 + IGFBP5 | 0.734 | 0.734 | 0.734 | 0.734 | 0.688 | 0.734 | 0.609 | 0.797 | 0.609 | 0.625 |
| MDK + CDC2 + HOXA13 | 0.688 | 0.719 | 0.688 | 0.719 | 0.594 | 0.672 | 0.609 | 0.641 | 0.641 | 0.641 |
| MDK + IGFBP5 + HOXA13 | 0.703 | 0.719 | 0.703 | 0.719 | 0.719 | 0.750 | 0.562 | 0.703 | 0.641 | 0.641 |
| CDC2 + IGFBP5 + HOXA13 | 0.750 | 0.766 | 0.750 | 0.766 | 0.719 | 0.734 | 0.594 | 0.688 | 0.625 | 0.625 |
| MDK+CDC2+IGFBP5+HOXA13 | 0.766 | 0.750 | 0.750 | 0.750 | 0.688 | 0.750 | 0.625 | 0.719 | 0.609 | 0.594 |

Sensitivity at Specificity: Sp.85

Figure 16b

| c | Model | LDA | | LogReg | | SVM | | KN5N | | TREE | |
|---|---|---|---|---|---|---|---|---|---|---|---|
| | | -IL8Rb | +IL8Rb | -IL8Rb | +IL8Rb | -IL8Rb | +IL8Rb | -IL8Rb | +IL8Rb | -IL8Rb | +IL8Rb |
| | MDK | 0.511 | 0.672 | 0.625 | 0.672 | 0.562 | 0.641 | 0.531 | 0.609 | 0.609 | 0.594 |
| | CDC2 | 0.338 | 0.703 | 0.656 | 0.703 | 0.531 | 0.688 | 0.500 | 0.625 | 0.625 | 0.672 |
| | IGFBP5 | 0.212 | 0.562 | 0.562 | 0.562 | 0.500 | 0.594 | 0.516 | 0.484 | 0.500 | 0.562 |
| | HOXA13 | 0.257 | 0.516 | 0.500 | 0.531 | 0.438 | 0.469 | 0.406 | 0.375 | 0.391 | 0.359 |
| | MDK + CDC2 | 0.688 | 0.703 | 0.688 | 0.688 | 0.625 | 0.688 | 0.562 | 0.672 | 0.562 | 0.578 |
| | MDK + IGFBP5 | 0.641 | 0.719 | 0.641 | 0.688 | 0.703 | 0.719 | 0.562 | 0.625 | 0.578 | 0.594 |
| | MDK + HOXA13 | 0.641 | 0.672 | 0.625 | 0.656 | 0.562 | 0.641 | 0.562 | 0.516 | 0.594 | 0.578 |
| | CDC2 + IGFBP5 | 0.656 | 0.750 | 0.672 | 0.734 | 0.609 | 0.688 | 0.578 | 0.641 | 0.547 | 0.594 |
| | CDC + HOXA13 | 0.641 | 0.703 | 0.656 | 0.688 | 0.547 | 0.688 | 0.594 | 0.547 | 0.594 | 0.672 |
| | IGF + HOXA13 | 0.594 | 0.594 | 0.578 | 0.578 | 0.672 | 0.688 | 0.500 | 0.484 | 0.594 | 0.578 |
| | MDK + CDC2 + IGFBP5 | 0.672 | 0.734 | 0.672 | 0.719 | 0.656 | 0.734 | 0.609 | 0.672 | 0.531 | 0.578 |
| | MDK + CDC2 + HOXA13 | 0.688 | 0.688 | 0.688 | 0.703 | 0.578 | 0.672 | 0.609 | 0.641 | 0.531 | 0.562 |
| | MDK + IGFBP5 + HOXA13 | 0.641 | 0.672 | 0.625 | 0.656 | 0.688 | 0.688 | 0.562 | 0.562 | 0.609 | 0.594 |
| | CDC2 + IGFBP5 + HOXA13 | 0.672 | 0.766 | 0.703 | 0.734 | 0.672 | 0.688 | 0.594 | 0.547 | 0.578 | 0.594 |
| | MDK+CDC2+IGFBP5+HOXA13 | 0.688 | 0.719 | 0.703 | 0.719 | 0.672 | 0.734 | 0.625 | 0.672 | 0.500 | 0.562 |

Sensitivity at Specificity: Sp.90

Figure 16c

| Model | LDA -IL8Rb | LDA +IL8Rb | LogReg -IL8Rb | LogReg +IL8Rb | SVM -IL8Rb | SVM +IL8Rb | KN5N -IL8Rb | KN5N +IL8Rb | TREE -IL8Rb | TREE +IL8Rb |
|---|---|---|---|---|---|---|---|---|---|---|
| MDK | 0.304 | 0.609 | 0.547 | 0.609 | 0.531 | 0.609 | 0.500 | 0.609 | 0.500 | 0.562 |
| CDC2 | 0.180 | 0.625 | 0.516 | 0.625 | 0.500 | 0.609 | 0.438 | 0.625 | 0.500 | 0.609 |
| IGFBP5 | 0.148 | 0.484 | 0.484 | 0.484 | 0.500 | 0.500 | 0.359 | 0.391 | 0.469 | 0.438 |
| HOXA13 | 0.173 | 0.422 | 0.438 | 0.422 | 0.422 | 0.406 | 0.297 | 0.297 | 0.344 | 0.297 |
| MDK + CDC2 | 0.562 | 0.672 | 0.562 | 0.672 | 0.547 | 0.672 | 0.453 | 0.672 | 0.453 | 0.562 |
| MDK + IGFBP5 | 0.562 | 0.609 | 0.578 | 0.609 | 0.609 | 0.656 | 0.562 | 0.625 | 0.531 | 0.547 |
| MDK + HOXA13 | 0.531 | 0.609 | 0.531 | 0.609 | 0.531 | 0.609 | 0.562 | 0.516 | 0.500 | 0.562 |
| CDC2 + IGFBP5 | 0.562 | 0.609 | 0.562 | 0.625 | 0.562 | 0.594 | 0.453 | 0.641 | 0.500 | 0.547 |
| CDC + HOXA13 | 0.516 | 0.625 | 0.500 | 0.625 | 0.516 | 0.609 | 0.594 | 0.547 | 0.516 | 0.609 |
| IGF + HOXA13 | 0.484 | 0.484 | 0.531 | 0.531 | 0.547 | 0.531 | 0.500 | 0.484 | 0.406 | 0.406 |
| MDK + CDC2 + IGFBP5 | 0.594 | 0.656 | 0.609 | 0.672 | 0.578 | 0.641 | 0.609 | 0.672 | 0.469 | 0.500 |
| MDK + CDC2 + HOXA13 | 0.562 | 0.672 | 0.562 | 0.672 | 0.547 | 0.672 | 0.516 | 0.641 | 0.484 | 0.562 |
| MDK + IGFBP5 + HOXA13 | 0.609 | 0.625 | 0.609 | 0.609 | 0.609 | 0.656 | 0.562 | 0.562 | 0.531 | 0.547 |
| CDC2 + IGFBP5 + HOXA13 | 0.609 | 0.641 | 0.578 | 0.656 | 0.594 | 0.641 | 0.594 | 0.547 | 0.484 | 0.516 |
| MDK+CDC2+IGFBP5+HOXA13 | 0.609 | 0.688 | 0.594 | 0.672 | 0.625 | 0.672 | 0.625 | 0.672 | 0.469 | 0.484 |

Sensitivity at Specificity: Sp.95

Figure 16d

| Model | LDA | | LogReg | | SVM | | KN5N | | TREE | |
|---|---|---|---|---|---|---|---|---|---|---|
| | -IL8Rb | +IL8Rb | -IL8Rb | +IL8Rb | -IL8Rb | +IL8Rb | -IL8Rb | +IL8Rb | -IL8Rb | +IL8Rb |
| MDK | 0.163 | 0.516 | 0.484 | 0.516 | 0.469 | 0.547 | 0.312 | 0.516 | 0.359 | 0.562 |
| CDC2 | 0.047 | 0.453 | 0.469 | 0.469 | 0.453 | 0.562 | 0.438 | 0.500 | 0.469 | 0.422 |
| IGFBP5 | 0.054 | 0.391 | 0.391 | 0.391 | 0.359 | 0.375 | 0.234 | 0.266 | 0.219 | 0.266 |
| HOXA13 | 0.089 | 0.281 | 0.312 | 0.281 | 0.297 | 0.281 | 0.203 | 0.297 | 0.234 | 0.234 |
| MDK + CDC2 | 0.484 | 0.578 | 0.500 | 0.578 | 0.469 | 0.578 | 0.375 | 0.422 | 0.359 | 0.391 |
| MDK + IGFBP5 | 0.484 | 0.547 | 0.484 | 0.547 | 0.469 | 0.500 | 0.531 | 0.344 | 0.359 | 0.359 |
| MDK + HOXA13 | 0.484 | 0.547 | 0.469 | 0.547 | 0.469 | 0.484 | 0.422 | 0.500 | 0.359 | 0.562 |
| CDC2 + IGFBP5 | 0.484 | 0.500 | 0.484 | 0.500 | 0.469 | 0.484 | 0.453 | 0.484 | 0.438 | 0.422 |
| CDC + HOXA13 | 0.469 | 0.422 | 0.453 | 0.469 | 0.422 | 0.484 | 0.484 | 0.406 | 0.453 | 0.453 |
| IGF + HOXA13 | 0.391 | 0.391 | 0.375 | 0.375 | 0.375 | 0.422 | 0.234 | 0.406 | 0.219 | 0.250 |
| MDK + CDC2 + IGFBP5 | 0.484 | 0.578 | 0.484 | 0.562 | 0.500 | 0.562 | 0.500 | 0.484 | 0.312 | 0.391 |
| MDK + CDC2 + HOXA13 | 0.484 | 0.609 | 0.484 | 0.609 | 0.484 | 0.578 | 0.344 | 0.578 | 0.359 | 0.391 |
| MDK + IGFBP5 + HOXA13 | 0.469 | 0.531 | 0.500 | 0.547 | 0.469 | 0.516 | 0.469 | 0.406 | 0.359 | 0.359 |
| CDC2 + IGFBP5 + HOXA13 | 0.469 | 0.484 | 0.469 | 0.484 | 0.469 | 0.500 | 0.469 | 0.469 | 0.453 | 0.422 |
| MDK+CDC2+IGFBP5+HOXA13 | 0.484 | 0.609 | 0.484 | 0.609 | 0.469 | 0.531 | 0.516 | 0.484 | 0.344 | 0.391 |

Sensitivity at Specificity: Sp.98

Figure 16e

| Model | LDA | LogReg | SVM | KN5N | TREE |
|---|---|---|---|---|---|
| MDK | 0.013 | 0.000 | 0.078 | 0.250 | 0.062 |
| CDC2 | -0.019 | -0.016 | 0.141 | -0.016 | 0.031 |
| IGFBP5 | 0.046 | 0.016 | 0.109 | 0.141 | -0.047 |
| HOXA13 | 0.123 | -0.016 | -0.016 | -0.031 | 0.031 |
| MDK + CDC2 | 0.016 | 0.016 | 0.078 | 0.016 | -0.031 |
| MDK + IGFBP5 | 0.000 | 0.000 | 0.078 | 0.078 | 0.000 |
| MDK + HOXA13 | 0.000 | -0.016 | 0.031 | 0.016 | 0.062 |
| CDC2 + IGFBP5 | 0.016 | 0.016 | 0.109 | 0.094 | 0.016 |
| CDC + HOXA13 | -0.016 | -0.016 | 0.141 | -0.016 | 0.047 |
| IGF + HOXA13 | 0.000 | 0.000 | 0.031 | 0.141 | -0.016 |
| MDK + CDC2 + IGFBP5 | 0.000 | 0.000 | 0.078 | 0.062 | -0.031 |
| MDK + CDC2 + HOXA13 | 0.000 | 0.000 | 0.078 | -0.062 | 0.000 |
| MDK + IGFBP5 + HOXA13 | -0.016 | -0.016 | 0.047 | -0.047 | 0.000 |
| CDC2 + IGFBP5 + HOXA13 | 0.000 | -0.031 | 0.031 | -0.047 | 0.000 |
| MDK+CDC2+IGFBP5+HOXA13 | 0.016 | 0.016 | 0.062 | -0.047 | -0.016 |

Gain in sensitivity, starting at specificity=0.80

Figure 17a

| Model | LDA | LogReg | SVM | KN5N | TREE |
|---|---|---|---|---|---|
| MDK | 0.062 | 0.047 | 0.047 | 0.078 | 0.062 |
| CDC2 | 0.222 | -0.016 | -0.016 | 0.125 | 0.031 |
| IGFBP5 | 0.046 | 0.031 | 0.031 | -0.031 | 0.016 |
| HOXA13 | 0.132 | 0.000 | 0.031 | -0.031 | -0.094 |
| MDK + CDC2 | 0.047 | 0.047 | 0.016 | 0.109 | 0.000 |
| MDK + IGFBP5 | 0.016 | 0.016 | 0.016 | 0.203 | 0.000 |
| MDK + HOXA13 | 0.031 | 0.031 | 0.016 | -0.047 | 0.031 |
| CDC2 + IGFBP5 | 0.016 | 0.016 | 0.016 | 0.062 | 0.016 |
| CDC + HOXA13 | -0.016 | -0.016 | -0.016 | -0.047 | 0.047 |
| IGF + HOXA13 | 0.000 | 0.000 | 0.062 | -0.016 | 0.000 |
| MDK + CDC2 + IGFBP5 | 0.000 | 0.000 | 0.016 | 0.188 | 0.016 |
| MDK + CDC2 + HOXA13 | 0.031 | 0.031 | 0.000 | 0.031 | 0.000 |
| MDK + IGFBP5 + HOXA13 | 0.016 | 0.016 | 0.047 | 0.141 | 0.000 |
| CDC2 + IGFBP5 + HOXA13 | 0.016 | 0.016 | 0.031 | 0.094 | 0.000 |
| MDK+CDC2+IGFBP5+HOXA13 | -0.016 | 0.000 | -0.016 | 0.094 | -0.016 |

Gain in sensitivity, starting at specificity=0.85

Figure 17b

| Model | LDA | LogReg | SVM | KN5N | TREE |
|---|---|---|---|---|---|
| MDK | 0.161 | 0.047 | 0.078 | 0.078 | -0.016 |
| CDC2 | 0.365 | 0.047 | 0.156 | 0.125 | 0.047 |
| IGFBP5 | 0.350 | 0.000 | 0.094 | -0.031 | 0.062 |
| HOXA13 | 0.259 | 0.031 | 0.031 | -0.031 | -0.031 |
| MDK + CDC2 | 0.016 | 0.000 | 0.062 | 0.109 | 0.016 |
| MDK + IGFBP5 | 0.078 | 0.047 | 0.016 | 0.062 | 0.016 |
| MDK + HOXA13 | 0.031 | 0.031 | 0.078 | -0.047 | -0.016 |
| CDC2 + IGFBP5 | 0.094 | 0.062 | 0.078 | 0.062 | 0.047 |
| CDC + HOXA13 | 0.062 | 0.031 | 0.141 | -0.047 | 0.078 |
| IGF + HOXA13 | 0.000 | 0.000 | 0.016 | -0.016 | -0.016 |
| MDK + CDC2 + IGFBP5 | 0.062 | 0.047 | 0.078 | 0.062 | 0.047 |
| MDK + CDC2 + HOXA13 | 0.000 | 0.016 | 0.094 | 0.031 | 0.031 |
| MDK + IGFBP5 + HOXA13 | 0.031 | 0.031 | 0.000 | 0.000 | -0.016 |
| CDC2 + IGFBP5 + HOXA13 | 0.094 | 0.031 | 0.016 | -0.047 | 0.016 |
| MDK+CDC2+IGFBP5+HOXA13 | 0.031 | 0.016 | 0.062 | 0.047 | 0.062 |

Gain in sensitivity, starting at specificity=0.90

Figure 17c

| Model | LDA | LogReg | SVM | KN5N | TREE |
|---|---|---|---|---|---|
| MDK | 0.306 | 0.062 | 0.078 | 0.109 | 0.062 |
| CDC2 | 0.445 | 0.109 | 0.109 | 0.188 | 0.109 |
| IGFBP5 | 0.336 | 0.000 | 0.000 | 0.031 | -0.031 |
| HOXA13 | 0.249 | -0.016 | -0.016 | 0.000 | -0.047 |
| MDK + CDC2 | 0.109 | 0.109 | 0.125 | 0.219 | 0.109 |
| MDK + IGFBP5 | 0.047 | 0.031 | 0.047 | 0.062 | 0.016 |
| MDK + HOXA13 | 0.078 | 0.078 | 0.078 | -0.047 | 0.062 |
| CDC2 + IGFBP5 | 0.047 | 0.062 | 0.031 | 0.188 | 0.047 |
| CDC + HOXA13 | 0.109 | 0.125 | 0.094 | -0.047 | 0.094 |
| IGF + HOXA13 | 0.000 | 0.000 | -0.016 | -0.016 | 0.000 |
| MDK + CDC2 + IGFBP5 | 0.062 | 0.062 | 0.062 | 0.062 | 0.031 |
| MDK + CDC2 + HOXA13 | 0.109 | 0.109 | 0.125 | 0.125 | 0.078 |
| MDK + IGFBP5 + HOXA13 | 0.016 | 0.000 | 0.047 | 0.000 | 0.016 |
| CDC2 + IGFBP5 + HOXA13 | 0.031 | 0.078 | 0.047 | -0.047 | 0.031 |
| MDK+CDC2+IGFBP5+HOXA13 | 0.078 | 0.078 | 0.047 | 0.047 | 0.016 |

Gain in sensitivity, starting at specificity=0.95

Figure 17d

| Model | LDA | LogReg | SVM | KN5N | TREE |
|---|---|---|---|---|---|
| MDK | 0.353 | 0.031 | 0.078 | 0.203 | 0.203 |
| CDC2 | 0.406 | 0.000 | 0.109 | 0.062 | -0.047 |
| IGFBP5 | 0.336 | 0.000 | 0.016 | 0.031 | 0.047 |
| HOXA13 | 0.192 | -0.031 | -0.016 | 0.094 | 0.000 |
| MDK + CDC2 | 0.094 | 0.078 | 0.109 | 0.047 | 0.031 |
| MDK + IGFBP5 | 0.062 | 0.062 | 0.031 | -0.188 | 0.000 |
| MDK + HOXA13 | 0.062 | 0.078 | 0.016 | 0.078 | 0.203 |
| CDC2 + IGFBP5 | 0.016 | 0.016 | 0.016 | 0.031 | -0.016 |
| CDC + HOXA13 | -0.047 | 0.016 | 0.062 | -0.078 | 0.000 |
| IGF + HOXA13 | 0.000 | 0.000 | 0.047 | 0.172 | 0.031 |
| MDK + CDC2 + IGFBP5 | 0.094 | 0.078 | 0.062 | -0.016 | 0.078 |
| MDK + CDC2 + HOXA13 | 0.125 | 0.125 | 0.094 | 0.234 | 0.031 |
| MDK + IGFBP5 + HOXA13 | 0.062 | 0.047 | 0.047 | -0.062 | 0.000 |
| CDC2 + IGFBP5 + HOXA13 | 0.016 | 0.016 | 0.031 | 0.000 | -0.031 |
| MDK+CDC2+IGFBP5+HOXA13 | 0.125 | 0.125 | 0.062 | -0.031 | 0.047 |

Gain in sensitivity, starting at specificity=0.98

Figure 17e

| Model | LDA | LogReg | SVM | KN5N | TREE |
|---|---|---|---|---|---|
| MDK | 0.030 | 0.000 | 0.168 | 0.180 | 0.069 |
| CDC2 | -0.025 | -0.040 | 0.178 | -0.104 | 0.094 |
| IGFBP5 | 0.037 | 0.022 | 0.131 | 0.119 | -0.025 |
| HOXA13 | 0.114 | -0.007 | -0.002 | 0.116 | 0.027 |
| MDK + CDC2 | 0.012 | 0.030 | 0.158 | -0.101 | -0.049 |
| MDK + IGFBP5 | 0.000 | 0.000 | 0.101 | 0.146 | -0.022 |
| MDK + HOXA13 | 0.000 | -0.054 | 0.126 | -0.089 | 0.072 |
| CDC2 + IGFBP5 | 0.022 | 0.012 | 0.143 | 0.146 | 0.035 |
| CDC + HOXA13 | -0.025 | -0.040 | 0.158 | -0.109 | 0.106 |
| IGF + HOXA13 | 0.000 | 0.000 | 0.042 | 0.158 | 0.005 |
| MDK + CDC2 + IGFBP5 | 0.000 | 0.000 | 0.133 | 0.151 | -0.012 |
| MDK + CDC2 + HOXA13 | 0.000 | 0.000 | 0.165 | -0.091 | -0.035 |
| MDK + IGFBP5 + HOXA13 | -0.022 | -0.022 | 0.081 | -0.042 | -0.032 |
| CDC2 + IGFBP5 + HOXA13 | 0.000 | -0.094 | 0.064 | -0.032 | 0.015 |
| MDK+CDC2+IGFBP5+HOXA13 | 0.027 | 0.000 | 0.138 | -0.057 | -0.010 |

Gain in specificity, starting at specificity=0.80

Figure 17f

| Model | LDA | LogReg | SVM | KN5N | TREE |
|---|---|---|---|---|---|
| MDK | 0.059 | 0.041 | 0.123 | 0.130 | 0.039 |
| CDC2 | 0.125 | -0.023 | 0.130 | 0.130 | 0.044 |
| IGFBP5 | 0.041 | 0.009 | 0.081 | 0.069 | 0.036 |
| HOXA13 | 0.064 | -0.001 | -0.001 | 0.066 | -0.015 |
| MDK + CDC2 | 0.054 | 0.046 | 0.108 | 0.118 | -0.001 |
| MDK + IGFBP5 | 0.051 | 0.041 | 0.051 | 0.096 | 0.019 |
| MDK + HOXA13 | 0.051 | 0.044 | 0.103 | 0.086 | 0.041 |
| CDC2 + IGFBP5 | 0.017 | 0.002 | 0.093 | 0.096 | 0.031 |
| CDC + HOXA13 | -0.018 | -0.028 | 0.113 | 0.086 | 0.056 |
| IGF + HOXA13 | -0.001 | -0.001 | 0.002 | 0.108 | -0.008 |
| MDK + CDC2 + IGFBP5 | -0.001 | -0.001 | 0.083 | 0.101 | 0.014 |
| MDK + CDC2 + HOXA13 | 0.049 | 0.054 | 0.118 | 0.130 | -0.001 |
| MDK + IGFBP5 + HOXA13 | 0.007 | 0.014 | 0.031 | 0.113 | 0.009 |
| CDC2 + IGFBP5 + HOXA13 | 0.051 | 0.007 | 0.014 | 0.101 | -0.003 |
| MDK+CDC2+IGFBP5+HOXA13 | -0.015 | -0.001 | 0.088 | 0.110 | 0.004 |

Gain in specificity, starting at specificity=0.85

Figure 17g

| Model | LDA | LogReg | SVM | KN5N | TREE |
|---|---|---|---|---|---|
| MDK | 0.078 | 0.021 | 0.075 | 0.080 | -0.011 |
| CDC2 | 0.098 | 0.038 | 0.080 | 0.080 | 0.028 |
| IGFBP5 | 0.090 | 0.001 | 0.043 | 0.019 | 0.011 |
| HOXA13 | 0.088 | 0.004 | 0.028 | 0.016 | -0.026 |
| MDK + CDC2 | 0.004 | 0.001 | 0.058 | 0.068 | 0.043 |
| MDK + IGFBP5 | 0.028 | 0.026 | 0.001 | 0.046 | 0.009 |
| MDK + HOXA13 | 0.011 | 0.016 | 0.063 | 0.036 | -0.009 |
| CDC2 + IGFBP5 | 0.021 | 0.028 | 0.043 | 0.046 | 0.058 |
| CDC + HOXA13 | 0.019 | 0.033 | 0.063 | 0.036 | 0.053 |
| IGF + HOXA13 | 0.001 | 0.001 | 0.004 | 0.058 | -0.031 |
| MDK + CDC2 + IGFBP5 | 0.048 | 0.043 | 0.036 | 0.051 | 0.048 |
| MDK + CDC2 + HOXA13 | 0.001 | 0.004 | 0.075 | 0.080 | 0.053 |
| MDK + IGFBP5 + HOXA13 | 0.041 | 0.046 | 0.001 | 0.063 | 0.004 |
| CDC2 + IGFBP5 + HOXA13 | 0.021 | 0.033 | 0.021 | 0.051 | -0.001 |
| MDK+CDC2+IGFBP5+HOXA13 | 0.031 | 0.021 | 0.048 | 0.060 | 0.046 |

Gain in specificity, starting at specificity=0.90

Figure 17h

| Model | LDA | LogReg | SVM | KN5N | TREE |
|---|---|---|---|---|---|
| MDK | 0.043 | 0.025 | 0.030 | 0.030 | 0.028 |
| CDC2 | 0.050 | 0.025 | 0.030 | 0.030 | 0.023 |
| IGFBP5 | 0.043 | 0.001 | 0.001 | 0.015 | -0.007 |
| HOXA13 | 0.045 | -0.002 | -0.004 | 0.020 | -0.012 |
| MDK + CDC2 | 0.030 | 0.030 | 0.033 | 0.038 | 0.013 |
| MDK + IGFBP5 | 0.023 | 0.025 | 0.010 | -0.004 | 0.006 |
| MDK + HOXA13 | 0.030 | 0.030 | 0.013 | -0.014 | 0.028 |
| CDC2 + IGFBP5 | 0.020 | 0.018 | 0.015 | 0.025 | 0.015 |
| CDC + HOXA13 | 0.023 | 0.025 | 0.025 | -0.014 | 0.015 |
| IGF + HOXA13 | 0.001 | 0.001 | -0.007 | 0.008 | 0.003 |
| MDK + CDC2 + IGFBP5 | 0.025 | 0.023 | 0.023 | 0.001 | 0.010 |
| MDK + CDC2 + HOXA13 | 0.035 | 0.033 | 0.033 | 0.030 | 0.013 |
| MDK + IGFBP5 + HOXA13 | 0.006 | 0.001 | 0.003 | 0.013 | 0.006 |
| CDC2 + IGFBP5 + HOXA13 | 0.003 | 0.015 | 0.008 | 0.001 | 0.008 |
| MDK+CDC2+IGFBP5+HOXA13 | 0.028 | 0.030 | 0.015 | 0.010 | 0.010 |

Gain in specificity, starting at specificity=0.95

Figure 17i

| Model | LDA | LogReg | SVM | KN5N | TREE |
|---|---|---|---|---|---|
| MDK | 0.015 | 0.005 | 0.008 | 0.005 | 0.008 |
| CDC2 | 0.020 | 0.000 | 0.000 | 0.000 | -0.007 |
| IGFBP5 | 0.018 | 0.000 | 0.000 | 0.000 | 0.003 |
| HOXA13 | 0.015 | -0.007 | -0.007 | 0.010 | 0.000 |
| MDK + CDC2 | 0.003 | 0.003 | 0.005 | 0.008 | 0.003 |
| MDK + IGFBP5 | 0.000 | 0.000 | 0.000 | -0.010 | 0.000 |
| MDK + HOXA13 | 0.008 | 0.008 | 0.008 | 0.010 | 0.008 |
| CDC2 + IGFBP5 | 0.005 | 0.000 | 0.003 | -0.005 | 0.000 |
| CDC + HOXA13 | -0.002 | 0.000 | 0.000 | -0.010 | -0.002 |
| IGF + HOXA13 | 0.000 | 0.000 | 0.003 | 0.008 | 0.003 |
| MDK + CDC2 + IGFBP5 | 0.003 | 0.003 | 0.005 | 0.005 | 0.010 |
| MDK + CDC2 + HOXA13 | 0.008 | 0.008 | 0.003 | 0.005 | 0.003 |
| MDK + IGFBP5 + HOXA13 | 0.008 | 0.005 | 0.000 | 0.005 | 0.000 |
| CDC2 + IGFBP5 + HOXA13 | 0.000 | 0.000 | 0.008 | 0.013 | -0.007 |
| MDK+CDC2+IGFBP5+HOXA13 | 0.005 | 0.005 | 0.005 | 0.005 | 0.010 |
| Gain in specificity, starting at specificity=0.98 | | | | | |

Figure 17j

METHODS FOR DETECTION OF MARKERS BLADDER CANCER AND INFLAMMATORY CONDITIONS OF THE BLADDER AND TREATMENT THEREOF

CLAIM OF PRIORITY

This application is filed under 35 U.S.C. 111(a) and 37 C.F.R. 1.53(b) and is a Division of U.S. patent application Ser. No. 13/884,681 filed 10 May 2013 (now U.S. Pat. No. 9,982,305, issued 29 May 2018), which is a National Phase application under 35 U.S.C. 371 claiming priority to International Patent Application No. PCT/NZ2011/000238 filed 11 Nov. 2011, which claims priority to New Zealand Provisional Patent Application No. NZ 589,251, filed 12 Nov. 2010. The patent and each of these applications are incorporated fully by reference as if separately so incorporated.

FIELD OF THE INVENTION

This invention relates to the detection of disease. Specifically, this invention relates to the use of genetic and/or protein markers for detection of bladder disease, and more particularly to the use of genetic and/or protein markers for detection of transitional cell carcinoma of the bladder (TCC) or for the detection of inflammatory conditions of the bladder.

BACKGROUND

Introduction

Survival of cancer patients is greatly enhanced when the cancer is treated early. In the case of bladder cancer, patients diagnosed with disease that is confined to the primary site have a 5 year survival rate of 73%, compared to 6% for patients with metastatic disease (Altekruse et al). Therefore, developments that lead to early and accurate diagnosis of bladder cancer can lead to an improved prognosis for the patients. To aid in early detection of cancer a number of cancer specific markers have been identified. However the use of these markers can result in false positive results in patients having inflammatory bladder diseases, and not bladder cancer.

Several tests have received FDA approval for bladder cancer diagnosis or monitoring including NMP22® ELISA (a registered trademark of Matritech, Inc., of Massachusetts, United States) and point-of-care BladderChek® assays (a registered trademark of Matritech, Inc. of Massachusetts, United States), UroVysion® (a registered trademark of Abbott Laboratories, Inc., of Illinois, United States), ImmunoCyt® (a registered trademark of Sanofi Pasteur Limited/Sanofi Pasteur Limitee, Ontario, Canada and Aventis Pasteur Limited/Adventis Pasteur Limitee, Ontario, Canada) and BTA (bladder tumour antigen), although none have demonstrated sufficient performance to routinely displace cytology.

SUMMARY OF THE INVENTION

There is a need for further markers that are specific for inflammatory disease in bladder, both for the diagnosis of inflammatory disease in the bladder and also to improve the diagnosis of transitional cell carcinoma of the bladder (TCC). Specifically, there is a need for markers to allow the differentiation of TCC from other inflammatory conditions.

Aspects of this invention provide methods, compositions and devices that can provide for detection of inflammatory disease in the bladder and also to decrease the frequency of false positive results in the diagnosis of transitional cell carcinoma of the bladder (TCC).

Proteins or nucleic acids that are secreted by or cleaved from the cell, or lost by apoptotic mechanisms, either alone or in combination with each other, have utility as serum or body fluid markers for the diagnosis of disease, including inflammatory disease in bladder and/or bladder cancer or as markers for monitoring the progression of established disease. Detection of protein and cell markers can be carried out using methods known in the art, and include the use of RT-PCT, qRT-PCR, monoclonal antibodies, polyclonal antisera and the like.

Specifically the present invention provides for a method for detecting or diagnosing bladder cancer, comprising: (i) providing a biological sample; and (ii) detecting the levels of human neutrophil marker interleukin 8 receptor B (IL8Rb) in association with one or more bladder tumour markers (BTM) in said sample. The presence of cancer can be established by comparing the levels of IL8Rb and the one or BTM with the levels in normal patients, patients having bladder cancer, and/or patients having an inflammatory disease. For example, the presence of cancer can be established by comparing the expression of the marker, including IL8Rb, against a threshold. The threshold may be in the order of expression that is at least 1.1, 1.2, 1.3, 1.4, 1.5, 1.6, 1.7, 1.8, 1.9, 2, 3, 4, 5, 6, 7, 8, 9, or 10 times normal expression or higher. A high expression of IL8Rb can be indicative of an inflammatory disease rather than cancer.

The method of the present invention can be used in conjunction with any suitable marker for detecting bladder cancer. Examples of suitable markers for use in the invention are outlined in FIG. 6 or FIG. 7. The present invention includes the use of any one or more of the markers outlined in FIG. 6 or FIG. 7 in conjunction with IL8Rb to detect bladder cancer in a patient.

In particular, the present invention involves the use of IL8Rb in conjunction with any one or more of the markers MDK, CDC2, HOXA13, and IGFBP5 to diagnosis bladder cancer. That is, the present invention also includes any combination of IL8Rb with one or more of the markers MDK, CDC2, HOXA13, and IGFBP5, which can also be in combination with one or more other marker suitable for detecting bladder cancer, for example, any one of more of the markers outlined in FIG. 6 or FIG. 7. Specifically, the present invention includes any one of the combination of markers: IL8Rb/MDK, IL8Rb/CDC2, IL8Rb/HOXA13, IL8Rb/IGFBP5, IL8Rb/MDK/CDC2, IL8Rb/MDK/HOXA13, IL8Rb/MDK/IGFBP5, IL8Rb/CDC2/HOXA13, IL8Rb/CDC2/IGFBP5, IL8Rb/HOXA13/IGFBP5, IL8Rb/MDK/CDC2/HOXA13, IL8Rb/MDK/CDC2/IGFBP5, IL8Rb/CDC2/HOXA13/IGFBP5, and IL8Rb/MDK/CDC2/HOXA13/IGFBP5. These combinations can optionally include one or more further markers suitable for detecting bladder cancer, for example any one of more of the markers outlined in FIG. 6 or FIG. 7.

The present invention also provides for a method for detecting inflammatory conditions of the bladder, comprising: (i) providing a biological sample from a patient; and (ii) detecting the levels of human neutrophil marker interleukin 8 receptor B (IL8Rb) in said sample. The presence of inflammatory conditions of the bladder is established by comparing the levels of IL8Rb with the levels in normal patients, and patients having an inflammatory condition of the bladder. For example, the presence of an inflammatory condition of the bladder can be established by comparing the expression of the marker, including IL8Rb, against a threshold, The threshold may be in the order of expression that is at least 1.1, 1.2, 1.3, 1.4, 1.5, 1.6, 1.7, 1.8, 1.9, 2, 3, 4, 5, 6, 7, 8, 9, or 10 times normal expression or higher.

The methods of the present invention can be carried out by detecting any suitable marker of gene expression, for example determining the levels of mRNA, cDNA, a protein or peptide utilizing, any suitable method.

The establishment of a diagnosis can be established through the use classifier system, for example Linear Discriminant Analysis (LDA), Logistic Regression (Log Reg), Support Vector Machine (SVM), K-nearest 5 neighbors (KN5N), and Partition Tree Classifier (TREE).

In another embodiment the invention provides for a device for detecting a bladder cancer, and or an inflammatory condition of the bladder, comprising: a substrate having a IL8Rb capture reagent and capture reagent for one or more bladder tumour marker (BTM) thereon; and a detector associated with said substrate, said detector capable of detecting a the expression associated with said capture reagent.

The invention also provides for a kit for detecting bladder cancer, comprising: a substrate having a IL8Rb capture reagent and a capture reagent for one or more bladder tumour markers (BTM) thereon; a means for visualizing a complex of said capture agent and a marker; reagents; and instructions for use.

In a further embodiment, the invention provides for a method for detecting bladder cancer, comprising the steps of: providing a test sample from a patient at risk of having bladder cancer; measuring the expression of IL8Rb protein and one or more bladder tumour marker (BTM) in said test sample; and comparing the amount of IL8Rb expression and one or more BTMs present in said test sample with a value obtained from one or more control samples from a subjects not having bladder cancer, and/or with one ore more control samples with subjects having an inflammatory condition of the bladder.

The present invention also provides for a method for screening for bladder cancer, comprising the steps of: providing a test sample from a test subject; measuring the presence of IL8Rb and at one or more bladder tumour markers (BTM) in said test sample; and comparing the amount of markers present in said test sample with a value obtained from one or more control samples from subjects not having bladder cancer, and/or with control samples with one or more subjects having an inflammatory condition of the bladder.

It has surprisingly been found that IL8Rb can detect the presence of an inflammatory bladder disease, and that this can be used to increase the ability of a marker for bladder cancer to accurately detect bladder cancer in a patient by reducing the potential of false positive results caused by an inflammatory bladder condition.

BRIEF DESCRIPTION OF THE FIGURES

This invention is described with reference to specific embodiments thereof and with reference to the figures, in which:

FIG. 1 shows the protein (SEQ ID NO.1) and mRNA (SEQ ID NO.2) sequences of IL8Rb (also known as CXCR2).

FIG. 2 includes FIGS. 2a-2c, which show scatter plots showing the effect of IL8Rb on the separation of TCC from non-malignant disease (cystitis, urinary tract infection and urolithiasis). IL8Rb has been substituted for different bladder cancer RNA markers in FIG. 2c. FIG. 2(c) MDK/IL8Rb.

FIG. 3(a). LD1 (solid) and LD2 (dashed). FIG. 3(b) LR1 (solid) and LR2 (dashed). IL8Rb is included in LD2 and LR2.

FIG. 4(a). LD1 (solid) and LD2 (dashed). FIG. 4(b) LR1 (dashed) and LR2 (solid). IL8Rb is included in LD2 and LR2.

FIG. 6 shows markers known to be over expressed in bladder cancer, and are suitable for use in the present invention.

FIG. 7 shows markers known to be under expressed in bladder cancer, and are suitable for use in the present invention.

FIG. 9 Baseline clinical and demographic characteristics of the patients by disease status at 3 months.

FIG. 10 shows overall sensitivity and specificity of the urine tests.

FIG. 11 includes FIGS. 11a-11b, which show various ROC curves; FIG. 11a. ROC curves for NMP22 ELISA and uRNA-D (test comprising the four markers MDK+CDC2+IGFBP5+HOXA13); and FIG. 11b. ROC curve for the five markers MDK, CDC2, HOXA13, IGFBP5 and IL8Rb.

FIG. 12 shows the sensitivity of urine tests by stage, grade, location of tumour, multiplicity of tumour, haematuria status, creatinine of urine sample and sex. Tables show numbers and percent with a positive urine test among those with TCC.

FIG. 13 shows the specificity of urine tests by diagnosis, microhaematuria, creatinine and sex. Tables show number and % with a negative urine test result among those without TCC.

FIG. 14(a) MDK, FIG. 14(b) CDC, FIG. 14(c) IGFBP5, FIG. 14(d) HOXA13, FIG. 14(e) MDK+CDC2, FIG. 14(f) MDK+IGFBP5, FIG. 14(g) MDK+HOXA13, FIG. 14(h) CDC2+IGFBP5, FIG. 14(i) CDC+HOXA13, FIG. 14(j) IGF+HOXA13, FIG. 14(k) MDK+CDC2+IGFBP5, FIG. 14(l) MDK+CDC2+HOXA13, FIG. 14(m) MDK+IGFBP5+HOXA13, FIG. 14(n) CDC2+IGFBP5+HOXA13, FIG. 14(o) MDK+CDC2+IGFBP5+HOXA13, plus or minus IL8Rb, using five different classifier models (i) Linear Discriminant Analysis (LDA), (ii) Logistic Regression (Log Reg), (iii) Support Vector Machine (SVM), (iv) K-nearest 5 neighbors (KN5N), and (v) Partition Tree Classifier (TREE).

FIGS. 15a-15b show FIG. 15(a) the "Area Under the Curve" (AUC) for up to 20% false positive rate (80% specificity) of the ROC curves from FIG. 14 and FIG. 15(b) shows the difference the AUC resulting from the inclusion of IL8Rb.

FIGS. 16a-16e show the sensitivity of the combinations of the four markers MDK, CDC2, IGFBP5, and HOXA13, plus or minus IL8Rb, using five different classifier models (i) Linear Discriminant Analysis (LDA), (ii) Logistic Regression (Log Reg), (iii) Support Vector Machine (SVM), (iv) K-nearest 5 neighbors (KN5N), and (v) Partition Tree Classifier (TREE), at different set specificities; FIG. 16(a) 80%, FIG. 16(b) 85%, FIG. 16(c) 90%, FIG. 16(d) 95%, FIG. 16(e) 98%.

FIGS. 17a-17j show the resulting gains in sensitivity from adding IL8Rb at different set specificities FIG. 17(a) 80%, FIG. 17(b) 85%, FIG. 17(c) 90%, FIG. 17(d) 95%, FIG. 17(e) 98%, and the resulting gains in specificity from adding IL8Rb at different set specificities FIG. 17(f) 80%, FIG. 17(g) 85%, FIG. 17(h) 90%, FIG. 17(i) 95%, FIG. 17(j) 98%

DETAILED DESCRIPTION

Sequence Listing

Figure 2A:
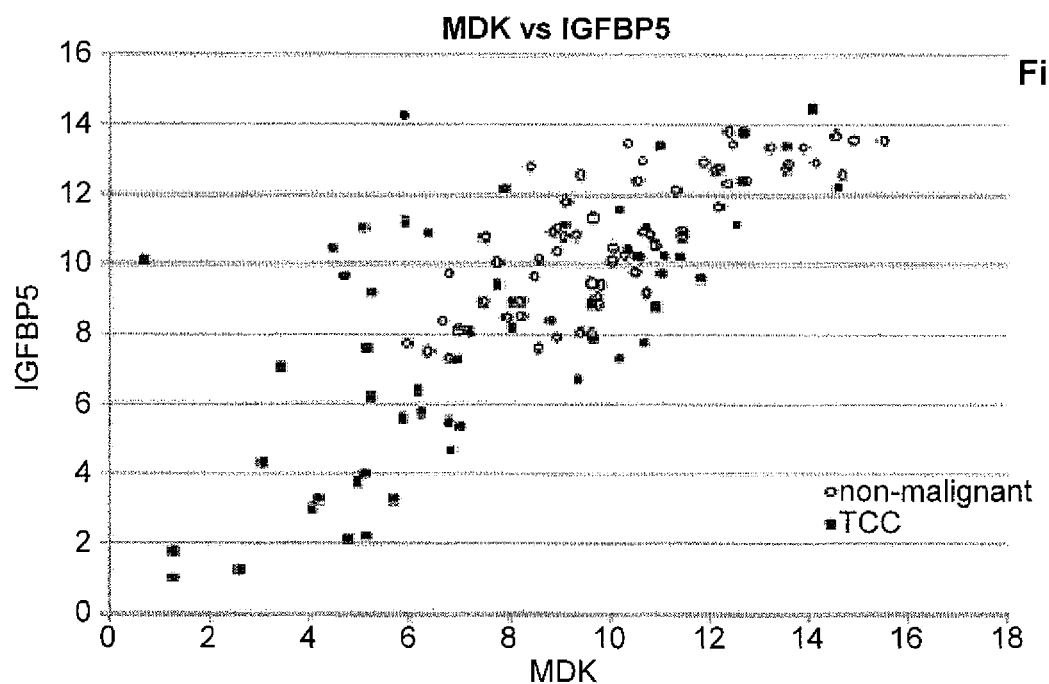
FIG. 2(a). MDK/IGFBP5.
Figure 2B:
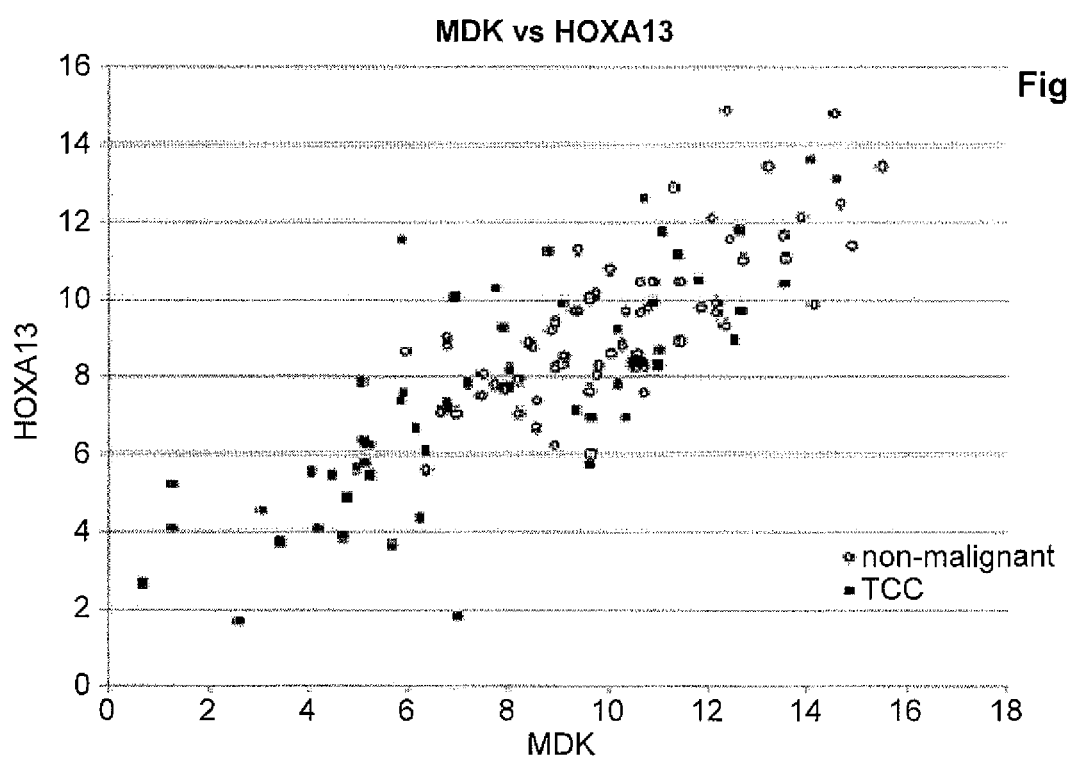
FIG. 2(b). MDK/HOXA13.

This application includes a sequence listing that is incorporated fully by reference.

Definitions

Before describing the embodiments of the invention in detail, it will be useful to provide some definitions of terms as used herein.

The term "marker" refers to a molecule that is associated quantitatively or qualitatively with the presence of a biological phenomenon. Examples of "markers" include a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments, whether related directly or indirectly to a mechanism underlying the phenomenon. The markers of the invention include the nucleotide sequences (e.g., GenBank sequences) as disclosed herein, in particular, the full-length sequences, any coding sequences, any fragments, or any complements thereof, and any measurable marker thereof as defined above.

As used herein "antibodies" and like terms refer to immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and Fab$_2$ fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., a mouse or human sequence. Further included are camelid antibodies, shark antibodies or nanobodies.

The terms "cancer" and "cancerous" refer to or describe the physiological condition in mammals that is typically characterized by abnormal or unregulated cell growth. Cancer and cancer pathology can be associated, for example, with metastasis, interference with the normal functioning of neighbouring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "tumour" refers to all neoplastic cell growth and proliferation, whether malignant or benign, and all precancerous and cancerous cells and tissues.

The term "bladder cancer" refers to a tumour originating in the bladder. These tumours are able to metastasize to any organ.

The term "BTM" or "bladder tumour marker" or "BTM family member" means a tumour marker (TM) that is associated with bladder cancer and transitional cell carcinoma of the bladder (TCC). The term BTM also includes combinations of individual markers, whose combination improves the sensitivity and specificity of detecting bladder cancer. It is to be understood that the term BTM does not require that the marker be specific only for bladder tumours. Rather, expression of BTM can be altered in other types of cells, diseased cells, tumours, including malignant tumours.

The term "under expressing BTM" means a marker that shows lower expression in bladder tumours than in non-malignant bladder tissue.

The term "over expressing BTM" means a marker that shows higher expression in bladder tumours than in non-malignant tissue.

The terms "differentially expressed," "differential expression," and like phrases, refer to a gene marker whose expression is activated to a higher or lower level in a subject (e.g., test sample) having a condition, specifically cancer, such as melanoma, relative to its expression in a control subject (e.g., reference sample). The terms also include markers whose expression is activated to a higher or lower level at different stages of the same condition; in diseases with a good or poor prognosis; or in cells with higher or lower levels of proliferation. A differentially expressed marker may be either activated or inhibited at the polynucleotide level or polypeptide level, or may be subject to alternative splicing to result in a different polypeptide product. Such differences may be evidenced by a change in mRNA levels, surface expression, secretion or other partitioning of a polypeptide, for example.

Differential expression may include a comparison of expression between two or more markers (e.g., genes or their gene products); or a comparison of the ratios of the expression between two or more markers (e.g., genes or their gene products); or a comparison of two differently processed products (e.g., transcripts or polypeptides) of the same marker, which differ between normal subjects and diseased subjects; or between various stages of the same disease; or between diseases having a good or poor prognosis; or between cells with higher and lower levels of proliferation; or between normal tissue and diseased tissue, specifically cancer, or melanoma. Differential expression includes both quantitative, as well as qualitative, differences in the temporal or cellular expression pattern in a gene or its expression products among, for example, normal and diseased cells, or among cells which have undergone different disease events or disease stages, or cells with different levels of proliferation.

The term "expression" includes production of polynucleotides and polypeptides, in particular, the production of RNA (e.g., mRNA) from a gene or portion of a gene, and includes the production of a polypeptide encoded by an RNA or gene or portion of a gene, and the appearance of a detectable material associated with expression. For example, the formation of a complex, for example, from a polypeptide-polypeptide interaction, polypeptide-nucleotide interaction, or the like, is included within the scope of the term "expression". Another example is the binding of a binding ligand, such as a hybridization probe or antibody, to a gene or other polynucleotide or oligonucleotide, a polypeptide or a protein fragment, and the visualization of the binding ligand. Thus, the intensity of a spot on a microarray, on a hybridization blot such as a Northern blot, or on an immunoblot such as a Western blot, or on a bead array, or by PCR analysis, is included within the term "expression" of the underlying biological molecule.

The terms "gene expression threshold," and "defined expression threshold" are used interchangeably and refer to the level of a marker in question, outside which the expression level of the polynucleotide or polypeptide serves as a predictive marker for a condition in the patient. For example, the expression of IL8Rb above a certain threshold is diagnostic that the patient has an inflammatory condition. A threshold can also be used when testing a patient for suspected bladder cancer, using bladder cancer makers. Expression levels above a threshold indicates that the patient has an inflammatory bladder condition, likely to cause a false positive test for cancer, whereas an expression level of IL8Rb below a threshold is predictive that the patient does not have an inflammatory bladder condition. By including the measurement of IL8Rb any result from the expression of the bladder tumour markers can be relied upon if the levels of IL8Rb is below the threshold (i.e. a positive result is likely to be positive for the patient having cancer rather than increased levels of the bladder tumour markers actually resulting from exfoliation of non-malignant cells from the mucosa from inflammation).

The term "diagnostic threshold" refers to a threshold in which a patient can be said to have been diagnosed either with or without a given condition, for example bladder cancer. A diagnostic threshold is generally set to achieve a desired sensitivity and specificity, depending on factors such as population, prevalence, and likely clinical outcome. In general the diagnostic threshold can be calculated and/or established using algorithms, and/or computerized data analysis.

The exact threshold will be dependent on the population and also any model being used to predict disease (predictive model). A threshold is established experimentally from clinical studies such as those described in the Examples below. Depending on the prediction model used, the expression threshold may be set to achieve maximum sensitivity, or for maximum specificity, or for minimum error (maximum classification rate). For example a higher threshold may be set to achieve minimum errors, but this may result in a lower sensitivity. Therefore, for any given predictive model, clinical studies will be used to set an expression threshold that generally achieves the highest sensitivity while having a minimal error rate. In general the threshold is likely to be in the order of expression that is at least 1.1, 1.2, 1.3, 1.4, 1.5, 1.6, 1.7, 1.8, 1.9, 2, 3, 4, 5, 6, 7, 8, 9, or 10 times normal expression or higher.

The term "sensitivity" means the proportion of individuals with the disease who test (by the model) positive. Thus, increased sensitivity means fewer false negative test results.

The term "specificity" means the proportion of individuals without the disease who test (by the model) negative. Thus, increased specificity means fewer false positive test results.

The term "ROC curve", or Receiver Operating Characteristic curve means a plot of the true positive rate (sensitivity) against the false positive rate (specificity) for different cut off points for a particular marker or test. Each point on the ROC curve represents a specific sensitivity/specificity point that will correspond to a given threshold. The ROC curve can be important to establish a threshold to give a desired outcome. The area under a ROC curve represents (expressed as an AUC analysis), can be a measure of how well a given marker or test can distinguish between to diagnostic outcomes. The ROC curve can also be used to compare the accuracy of two different tests.

The term "oligonucleotide" refers to a polynucleotide, typically a probe or primer, including, without limitation, single-stranded deoxyribonucleotides, single- or double-stranded ribonucleotides, RNA: DNA hybrids, and double-stranded DNAs. Oligonucleotides, such as single-stranded DNA probe oligonucleotides, are often synthesized by chemical methods, for example using automated oligonucleotide synthesizers that are commercially available, or by a variety of other methods, including in vitro expression systems, recombinant techniques, and expression in cells and organisms.

The term "overexpression" or "overexpressed" refers to an expression level of a gene or marker in a patient that is above that seen in normal tissue. Expression may be considered to be overexpressed if it is 1.1, 1.2, 1.3, 1.4, 1.5, 1.6, 1.7, 1.8, 1.9, 2, or greater then 2 times the expression in normal tissue.

The term "polynucleotide," when used in the singular or plural, generally refers to any polyribonucleotide or polydeoxribonucleotide, which may be unmodified RNA or DNA or modified RNA or DNA. This includes, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences. It will be understood that each reference to a "polynucleotide" or like term, herein, will include the full-length sequences as well as any fragments, derivatives, or variants thereof.

"Polypeptide," as used herein, refers to an oligopeptide, peptide, or protein sequence, or fragment thereof, and to naturally occurring, recombinant, synthetic, or semi-synthetic molecules. Where "polypeptide" is recited herein to refer to an amino acid sequence of a naturally occurring protein molecule, "polypeptide" and like terms, are not meant to limit the amino acid sequence to the complete, native amino acid sequence for the full-length molecule. It will be understood that each reference to a "polypeptide" or like term, herein, will include the full-length sequence, as well as any fragments, derivatives, or variants thereof.

The term "qPCR" or "QPCR" refers to quantative polymerase chain reaction as described, for example, in PCR Technique: Quantitative PCR, J. W. Larrick, ed., Eaton Publishing, 1997, and A-Z of Quantitative PCR, S. Bustin, ed., IUL Press, 2004.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. Additional details and explanation of stringency of hybridization reactions, are found e.g., in Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate, buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×, Denhardt's solution, sonicated salmon sperm DNA (50 ug/ml), 0.1% SDS, and 10% dextran sulfate at 42° C., with washes at 42° C. in 0.2×SSC (sodium chloride/sodium citrate) and 50% formamide at 55° C., followed by a high-stringency wash comprising 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e. g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "IL8Rb" means neutrophil marker interleukin 8 receptor B (also known as chemokine (C-X-C motif) receptor 2 [CXCR2]) (FIG. 1; Seq ID Nos 1 and 2), and includes the marker IL8Rb. The term includes a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments.

The term "reliability" includes the low incidence of false positives and/or false negatives. Thus, with higher reliability of a marker, fewer false positives and/or false negatives are associated with diagnoses made using that marker. Therefore, in certain embodiments, markers are provided that permit detection of bladder inflammatory disease or cancer with reliability greater than the reliability of prior art markers greater than 50%. In other embodiments, markers are provided that have reliability greater than about 70%; in other embodiments, greater than about 73%, in still other embodiments, greater than about 80%, in yet further embodiments, greater than about 90%, in still others, greater than about 95%, in yet further embodiments greater than about 98%, and in certain embodiments, about 100% reliability.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, Molecular Cloning: A Laboratory Manual, 2nd edition, Sambrook et al., 1989; Oligonucleotide Synthesis, M J Gait, ed., 1984; Animal Cell Culture, R. I. Freshney, ed., 1987; Methods in Enzymology, Academic Press, Inc.; Handbook of Experimental Immunology, 4th edition, D. M. Weir & CC. Blackwell, eds., Blackwell Science Inc., 1987; Gene Transfer Vectors for Mammalian Cells, J. M. Miller & M. P. Calos, eds., 1987; Current Protocols in Molecular Biology, F. M. Ausubel et al., eds., 1987; and PCR: The Polymerase Chain Reaction, Mullis et al., eds., 1994.

It is to be understood that the above terms may refer to protein, DNA sequence and/or RNA sequence. It is also to be understood that the above terms also refer to non-human proteins, DNA and/or RNA having homologous sequences as depicted herein.

DESCRIPTION OF EMBODIMENTS OF THE INVENTION

Gene markers can be used as diagnostic tools to detect disease in a patient. The markers can, for example, be differentially expressed between disease tissue and corresponding non-disease tissue. In this situation, the detection of differential expression is associated with the presence of the disease. Alternatively, the marker can be associated directly with changes occurring in the disease tissues, or changes resulting from the disease. Inflammatory diseases are associated with an increase in neutrophils. It has been found that the neutrophil marker interleukin 8 receptor B (IL8Rb), (also known as chemokine (C-X-C motif) receptor 2 [CXCR2]) (FIG. 1; Seq ID Nos 1 and 2), provides a good marker for the presence of neutrophils in a sample, and therefore can be used as a diagnostic marker for the detection of inflammatory disease in a sample, and in particular, in the detection of inflammatory disease of the bladder.

Figure 5:
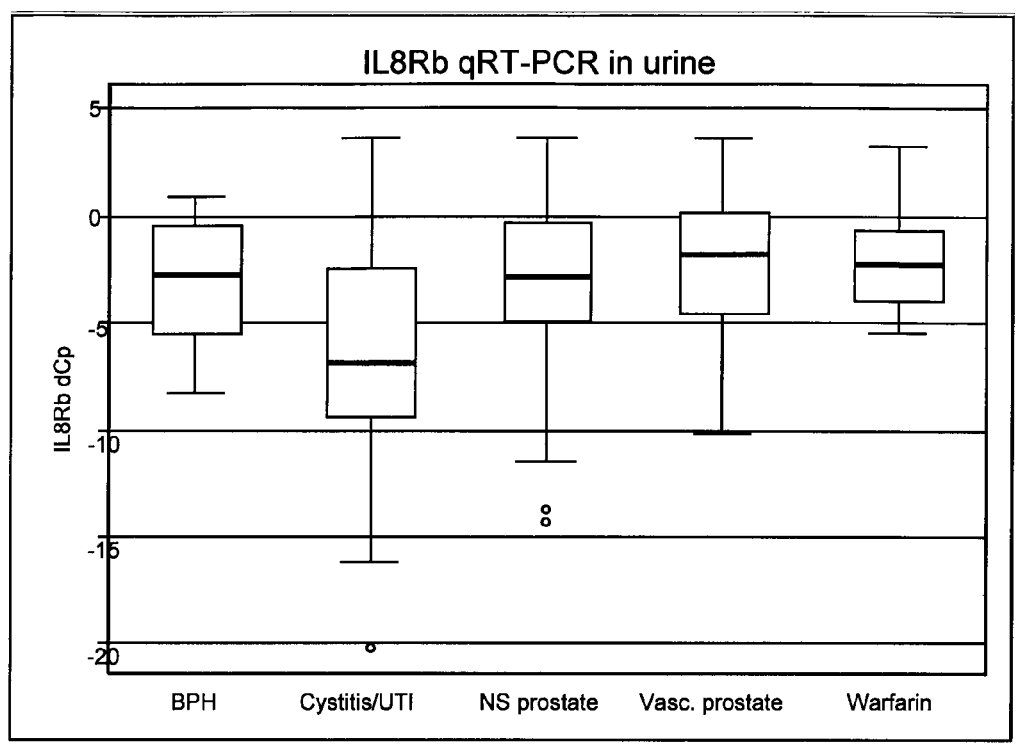
FIG. 5 shows box plots showing the accumulation of IL8Rb mRNA in the urine of patients with non-malignant urological disease. The RNA has been quantified by qRT-PCR using the delta-Ct method (Holyoake et al, 2008). With this method a lower Ct reflects higher RNA levels. BPH: benign prostatic hyperplasia; UTI: urinary tract infection; NS prostate: non-specific prostate diseases; Vasc. Prostate: vascular prostate; warfarin: hematuria secondary to warfarin use. The observations in patients with cystitis/UTI are significantly different (p=0.001) to the other non-malignant presentations shown.

As shown in FIG. 5, accumulation of IL8Rb in urine is indicative of the presence of inflammatory disease of the bladder. Specifically, FIG. 5 shows the accumulation of IL8Rb in the urine of patients having the conditions; benign prostatic hyperplasia, urinary tract infection, non-specific prostate diseases, vascular prostate and secondary warfarin use. It will be appreciated however, that the use of IL8Rb is not be limited to the detection of these diseases only, but that these examples show that IL8Rb does increase in samples from patients having an inflammatory disease of the bladder. That is, IL8Rb can be used as a marker of inflammation associated with bladder disease and therefore is suitable for use in detecting any condition associated with inflammation. Therefore, the detection of the amount of IL8Rb can be used as a marker for inflammatory disease of the bladder. More particularly, IL8Rb can be used to detect inflammatory disease of the bladder associated with the accumulation of neutrophils.

Urine tests for transitional cell carcinoma of the bladder (TCC) rely largely on the presence of markers in exfoliated tumour cells in the urine. The ability to detect these cells can be masked by the presence of large numbers of contaminating cells, such as, blood and inflammatory cells. Moreover, inflammation of the bladder lining can result in the increased exfoliation of non-malignant cells from the mucosa. As a result, urine tests that use markers derived from bladder transitional cells have a higher likelihood of giving a false positive result from urine samples taken from patients with cystitis, urinary tract infection or other conditions resulting in urinary tract inflammation or transitional cell exfoliation, such as, urolithiasis (Sanchez-Carbayo et al).

One way to try and avoid such false positive results has been to select markers with low relative expression in blood or inflammatory cells. The use of such markers results in fewer false positives in TCC patients presenting with non-malignant, inflammatory conditions. However, low expression of the markers in haematologically-derived cells fails to compensate for the enhanced rate of exfoliation of non-malignant transitional cells.

It has been discovered that the negative impact of exfoliated transitional cells from inflamed tissue has on the accuracy of bladder cancer urine tests can be minimised by improving the identification of patients with inflammatory conditions of the urinary tract. Here it has been surprisingly found that using the marker IL8Rb in combination with one or more bladder tumour markers (BTM's) provides for a more accurate detection of bladder cancer. In particular, a marker based test for bladder cancer that includes the marker IL8Rb is less susceptible to false positive results, which can result in patients suffering from an inflammatory non-cancer condition.

In general the presence or absence of an inflammatory condition is established by having a threshold of gene expression, above which expression of IL8Rb is indicative of a inflammatory condition. For example, the expression of IL8Rb above a certain threshold is diagnostic that the patient has an inflammatory condition. When IL8Rb is used in conjunction with one or more markers predictive for the presence of bladder cancer, the presence of elevated expression of the bladder tumour marker(s), and expression of IL8Rb, above a certain threshold, is predictive of the patient having an inflammatory condition and not cancer. Furthermore, if the test is preformed on urine from the patient, then this result is predictive of the patient having an inflammatory bladder condition. The high levels of the bladder tumour markers are most likely the result of non-malignant cells coming from the mucosa as a result of the inflammation. That is, the patient, although having high levels of the bladder tumour marker(s) does not actually have bladder cancer—a false positive.

Alternatively, if the patient has high levels or diagnostic levels of one or more bladder tumour markers, but the level of IL8Rb is below a threshold, then this is diagnostic that the patient is likely to have cancer, and in particular bladder cancer. This is especially so, if the test is preformed on urine from the patient. This result is of significant benefit to the health provider because they can be sure that the patient does have cancer, and can start treatment immediately, and not be concerned that the result is actually caused an inflammatory condition giving a false positive result.

It has been surprisingly shown that the quantification of RNA from the gene encoding the neutrophil marker interleukin 8 receptor B (IL8Rb) improves the overall performance of detecting patients with TCC, using known TCC or BTM markers. The reference sequences for IL8Rb (also known as chemokine (C-X-C motif) receptor 2 [CXCR2]) are shown in FIG. 1 and Seq ID Nos 1 and 2). In addition to its role in TCC detection, it has been explored whether IL8Rb could be used as a urine marker to aid in the diagnosis of inflammatory disease (FIG. 5).

The novel use of IL8Rb marker can be used in isolation for the detection of inflammatory conditions of the bladder utilizing known methods for detecting gene expression levels. Examples of methods for detecting gene expression are outlined below.

Alternatively, IL8Rb can be combined with one of more BTMs to detect bladder cancer. It has been shown that by utilizing the novel inflammatory disease marker IL8Rb as part of the test for bladder cancer, the influence of inflamed tissue on creating a false positive result is minimized. The marker IL8Rb can be used in association with any bladder cancer markers, or alternatively can be used with two or more markers, as part of a signature, for detecting bladder cancer.

The action of IL8Rb to improve the detection of bladder cancer results from the ability to separate non-malignant conditions from patients having bladder cancer. This is achieved because an increase of IL8Rb is indicative of an increase in the presence of neutrophils in a sample. Therefore, the ability of IL8Rb is not dependant on the bladder tumour marker used. As shown in FIGS. 2, and 12 to 15, when combined with a variety of bladder tumour markers and combinations of bladder tumour markers, IL8Rb had the general effect of increasing the specificity of the ability of the marker(s) to detect cancer in the subjects.

It will be appreciated that any marker that is cable of detecting bladder cancer is suitable for use in combination with IL8Rb. Examples of known BTMs suitable for use in combination with IL8Rb in the detection of TCC are outlined FIGS. 6 and 7. Specifically, FIG. 6 outlines markers known to be over expressed in bladder cancer, and FIG. 7 outlines a number of markers known to be under expressed in bladder cancer. The novel use of the marker, IL8Rb of the present invention can be used in combination with any one or more of the markers of FIG. 6 or FIG. 7, or alternatively in combination with a signature comprising two or more markers selected from FIG. 6 or FIG. 7.

One example of a signature according to the present invention is the use of IL8Rb in combination with MDK, CDC2, IGFBP5 and HOXA13, which may also be in combination with one or more other marker suitable for detecting bladder cancer, for example any one of more of the markers outlined in FIG. 6 or FIG. 7. As shown in FIGS. 14 and 15 IL8Rb can be used in any combination of the markers, specifically the combinations IL8Rb/MDK, IL8Rb/CDC2, IL8Rb/HOXA13, IL8Rb/IGFBP5, IL8Rb/MDK/CDC2, IL8Rb/MDK/HOXA13, IL8Rb/MDK/IGFBP5, IL8Rb/CDC2/HOXA13, IL8Rb/CDC2/IGFBP5, IL8Rb/HOXA13/IGFBP5, IL8Rb/MDK/CDC2/HOXA13, IL8Rb/MDK/CDC2/IGFBP5, IL8Rb/CDC2/HOXA13/IGFBP5, and IL8Rb/MDK/CDC2/HOXA13/IGFBP5. As shown in FIGS. 14 and 15, the inclusion of IL8Rb increased the ability of the marker, or the combination of markers to accurately diagnose bladder cancer in a subject. The present invention is not to be limited to these specific combinations but can optionally include one or more further markers suitable for detecting bladder cancer, for example any one of more of the markers outlined in FIG. 6 or FIG. 7.

| PE Gene Name | HGNC Gene Name (Official) | NCBI RefSeq | NCBI Entrez Gene ID | HGNC URL |
|---|---|---|---|---|
| MDK | MDK | NM_002391 | 4192 | www.genenames.org/data/hgnc_data.php?hgnc_id=6972 |
| CDC | CDK1 | NM_001170406 | 983 | www.genenames.org/data/hgnc_data.php?hgnc_id=1722 |
| IGF | IGFBP5 | NM_000599 | 3488 | www.genenames.org/data/hgnc_data.php?hgnc_id=5474 |
| HOXA | HOXA13 | NM_000522 | 3209 | www.genenames.org/data/hgnc_data.php?hgnc_id=5102 |
| IL8Rb | CXCR2 | NM_001168298 | 3579 | www.genenames.org/data/hgnc_data.php?hgnc_id=6027 |

Table 1, shows the identifiers for the specific markers MDK, CDC2, IGFBP5 and HOXA13 and IL8Rb.

FIGS. 2 to 4, and 12 to 17 show the effect of using IL8Rb in combination with four known, representative, markers of bladder cancer; MDK, CDC2, IGFBP5 and HOXA13. The results show that by incorporating the use if IL8Rb individually with each marker (FIGS. 2, 14 and 15 to 17), but also when used with all possible combinations of the four BTM markers as a signature, there is an improvement in the ability to separate the samples of patients with TCC and those with non malignant conditions.

More specifically, as shown in FIGS. 10 to 13, the inclusion of IL8Rb with the four markers MDK, CDC2, IGFBP5 and HOXA13 (uRNA-D not only increased the overall performance of the test compared to the four markers alone, the test also compared extremely favorably with other known tests, NMP22® "a registered trademark of Matritech, Inc., of Massachusetts, United States" Elisa, NMP22 BladderChek® "a registered trademark of Matritech, Inc., of Massachusetts, United States", and cytology. FIGS. 14 through 17 also show the effect of IL8Rb in the various combinations of the four markers MDK, CDC2, IGFBP5 and HOXA13.

Specifically, FIG. 14 shows the ROC curves for all the combinations of the four markers MDK, CDC2, IGFBP5 and HOXA13, with and without IL8Rb, calculated using five different classifier models (i) Linear Discriminant Analysis (LDA), (ii) Logistic Regression (Log Reg), (iii) Support Vector Machines (SVM), (iv) K-nearest 5 neighbors (KN5N), and (v) Partition Tree Classifier (TREE). FIG. 15 tabulates the Area Under the Curve (AUC) for all 5 classifiers and all 15 combinations of the 4 biomarkers, with and without IL8Rb. This AUC calculation is restricted to the area from a false positive rate of 0 to a false positive rate of 20%, covering the useful ranges of specificity (80-100%). The AUC quantifies the visible differences on the ROC curves of FIG. 14. FIG. 16 shows the sensitivity of all combinations of the four markers measured with and without IL8Rb at specificities of (a) 80%, (b) 85%, (c) 90%, (d) 95%, and (e) 98%. FIG. 17 tabulates the changes in either sensitivity (vertical direction on the ROC curves; better is "up") or specificity (horizontal direction on the ROC curve; better is to the left) at the fixed specificities of (a, 80%, (b, g) 85%, (c, h) 90%, (d, I) 95%, and (e, j) 98%.

These tables show that IL8Rb, in general, improves the ability of the biomarkers (MDK, CDC, IGFBP5, and HOXA13), singly or in combination, to classify tumour from normal samples.

These results generally show that the IL8Rb was able to increase the accuracy at which the test could detect bladder cancer. The biggest gains where seen with either markers that did not perform as well with out the inclusion of IL8Rb or with classifiers that did not perform as well. Smaller gains where seen for markers and/or classifiers that preformed well prior to adding IL8Rb and therefore there was less room for improvement. It is important to note that the results show a population based analysis and the benefit of incorporating IL8Rb could be greater when diagnosis individual patients, especially those whose diagnosis on the expression of the BTM markers maybe unclear.

These results show that not only can IL8Rb be used to detect inflammatory disease of the bladder, but also when used in combination with markers for bladder cancer, results in an improved detection of bladder cancer, arising from a reduction in "false positive" results.

These results also show the utility of IL8Rb in that it affects the overall performance of the various markers combinations, and confirms the ability of IL8Rb to improve the performance of one or more bladder cancer markers to accurately detect cancer in a patient. Further, FIGS. 14 and 15 shows that the same results can be achieved using a range of classifier models, and shows that the result is not dependent on a classifier model or algorithm, but rather the combination of markers used. These results confirm that any suitable classifier model or algorithm could be used in the present invention. In particular, FIGS. 14 and 15 show that IL:8Rb has a greater effect at the higher specificities, and in particular in the most clinically applicable ranges.

The present invention is based on the finding that detection of elevated levels of IL8Rb at either the polynucleotide or protein level in the urine is indicative of an inflammatory bladder disease. This can be used as a diagnosis tool alone for establishing an inflammatory bladder disease in a subject, but can also be used in conjunction with a test for bladder cancer in order to increase the specificity of the test by allowing the differentiation of the true positive result (ie the subject testing positive having bladder) from the false positive result (ie the subject testing positive for bladder cancer but in fact having an inflammatory bladder disease).

The method can be conducted on any suitable sample from the body that would be indicative of the urine, but ideally the level of IL8Rb, and any further cancer marker is established directly from a urine sample.

Detection of Markers in Body Samples

In several embodiments, assays for cancer can be desirably carried out on samples obtained from blood, plasma, serum, peritoneal fluid obtained for example using peritoneal washes, or other body fluids, such as urine, lymph, cerebrospinal fluid, gastric fluid or stool samples. For the detection of inflammatory conditions of the bladder or bladder cancer the test is ideally preformed on a urine sample.

Specifically the present method for detecting inflammatory bladder disease or bladder cancer can be conducted on any suitable sample from the body that would be indicative of the urine, but ideally the level of IL8Rb, and any further cancer marker is established directly from a urine sample.

A test can either be preformed directly on a urine sample, or the sample may be stabilised by the addition of any suitable compounds or buffers known in the art to stabilise and prevent the breakdown of RNA and/or protein in the sample so that it can be analysed at a later date, or even to ensure that the RNA and/or protein is stabilized during the analysis.

The determination of either the protein and/or RNA level in the subject's urine can be preformed directly on the urine, or the urine can be treated to further purify and/or concentrate the RNA and/or protein. Many methods for extracting and/or concentrating proteins and/or RNA are well known in the art and could be used in the present invention.

In order to establish whether a particular subject has differential expression of IL8Rb and if necessary any further cancer marker, the level of either the RNA and/or protein of IL8Rb and optionally one or more cancer markers can be measured in the sample. It will be appreciated that many methods are well known in the art for establishing the level of a particular gene, either at the RNA and/or protein level, and any suitable method can be used in the present invention. Some common methods are outlined below, however, the invention is not restricted to these methods and any method for quantifying protein and/or RNA levels is suitable for use in the present invention.

General Approaches to Disease and Cancer Detection Using Gene Markers

General methodologies for determining expression levels are outlined below, although it will be appreciated that any method for determining expression levels would be suitable.

Quantitative PCR (qPCR)

Quantitative PCR (qPCR) can be carried out on tumour samples, on serum and plasma using specific primers and probes. In controlled reactions, the amount of product formed in a PCR reaction (Sambrook, J., E Fritsch, E. and T Maniatis, Molecular Cloning: A Laboratory Manual $3^{rd}$. Cold Spring Harbor Laboratory Press: Cold Spring Harbor (2001)) correlates with the amount of starting template. Quantification of the PCR product can be carried out by stopping the PCR reaction when it is in log phase, before reagents become limiting. The PCR products are then electrophoresed in agarose or polyacrylamide gels, stained with ethidium bromide or a comparable DNA stain, and the intensity of staining measured by densitometry. Alternatively, the progression of a PCR reaction can be measured using PCR machines such as the Applied Biosystems' Prism 7000™ "a trademark of Applera Corporation, Connecticut, United States" or the Roche LightCycler™ (a trademark of Roche Molecular Systems, Inc., California, United States) which measure product accumulation in real-time. Real-time PCR measures either the fluorescence of DNA intercalating dyes such as Sybr Green into the synthesized PCR product, or the fluorescence released by a reporter molecule when cleaved from a quencher molecule; the reporter and quencher molecules are incorporated into an oligonucleotide probe which hybridizes to the target DNA molecule following DNA strand extension from the primer oligonucleotides. The oligonucleotide probe is displaced and degraded by the enzymatic action of the Taq polymerase in the next PCR cycle, releasing the reporter from the quencher molecule. In one variation, known as Scorpion, the probe is covalently linked to the primer.

Reverse Transcription PCR (RT-PCR)

RT-PCR can be used to compare RNA levels in different sample populations, in normal and tumour tissues, with or without drug treatment, to characterize patterns of expression, to discriminate between closely related RNAs, and to analyze RNA structure.

For RT-PCR, the first step is the isolation of RNA from a target sample. The starting material is typically total RNA isolated from human tumours or tumour cell lines, and corresponding normal tissues or cell lines, respectively. RNA can be isolated from a variety of samples, such as tumour samples from breast, lung, colon (e.g., large bowel or small bowel), colorectal, gastric, esophageal, anal, rectal, prostate, brain, liver, kidney, pancreas, spleen, thymus, testis, ovary, uterus, bladder etc., tissues, from primary tumours, or tumour cell lines, and from pooled samples from healthy donors. If the source of RNA is a tumour, RNA can be extracted, for example, from frozen or archived paraffin-embedded and fixed (e.g., formalin-fixed) tissue samples.

The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukaemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp® RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® qPCR (a registered trademark of Roche Molecular Systems, Inc., California, United States) typically utilizes the 5' nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR (a registered trademark of Roche Molecular Systems, Inc., California, United States) can be performed using commercially available equipment, such as, for example, ABI PRISM 7700™ Sequence Detection System (a trademark of Applera Corporation, Connecticut, United States) (Perkin-Elmer-Applied Biosystems, Foster City, Calif., USA), or Lightcycler™ (a registered trademark of Roche Molecular Systems, Inc., California, United States ((Roche Molecular Biochemicals, Mannheim, Germany). In a preferred embodiment, the 5' nuclease procedure is run on a real-time quantitative PCR device such as the ABI PRISM 7700™ "a trademark of Applera Corporation, Connecticut, United States" Sequence Detection System. The system consists of a thermocycler, laser, charge-coupled device (CCD), camera, and computer. The system amplifies samples in a 96-well format on a thermocycler. During amplification, laser-induced fluorescent signal is collected in real-time through fibre optics cables for all 96 wells, and detected at the CCD. The system includes software for running the instrument and for analyzing the data.

5' nuclease assay data are initially expressed as Cp, or the threshold cycle. As discussed above, fluorescence values are recorded during every cycle and represent the amount of product amplified to that point in the amplification reaction. The point when the fluorescent signal is first recorded as statistically significant is the threshold cycle.

Real-Time Quantitative PCR (qRT-PCR)

A more recent variation of the RT-PCR technique is the real time quantitative PCR, which measures PCR product accumulation through a dual-labeled fluorigenic probe (i.e., TaqMan® probe (a registered trademark of Roche Molecular Systems, Inc., California, United States)). Real time PCR is compatible both with quantitative competitive PCR and with quantitative comparative PCR. The former uses an internal competitor for each target sequence for normalization, while the latter uses a normalization gene contained within the sample, or a housekeeping gene for RT-PCR. Further details are provided, e.g., by Held et al., Genome Research 6: 986-994 (1996).

Expression levels can be determined using fixed, paraffin-embedded tissues as the RNA source. According to one aspect of the present invention, PCR primers are designed to flank intron sequences present in the gene to be amplified. In this embodiment, the first step in the primer/probe design is the delineation of intron sequences within the genes. This can be done by publicly available software, such as the DNA BLAT software developed by Kent, W. J., Genome Res. 12 (4): 656-64 (2002), or by the BLAST software including its variations. Subsequent steps follow well established methods of PCR primer and probe design.

In order to avoid non-specific signals, it is useful to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the VIMNV for general users and for biologist programmers in: Krawetz S, Misener S (eds) Bioinformatics Methods and Protocols: Methods in Molecular Biology. Humana Press, Totowa, N.J., pp 365-386).

The most important factors considered in PCR primer design include primer length, melting temperature (Tm), and G/C content, specificity, complementary primer sequences, and 3' end sequence. In general, optimal PCR primers are generally 1730 bases in length, and contain about 20-80%, such as, for example, about 50-60% G+C bases. Melting temperatures between 50 and 80° C., e.g., about 50 to 70° C., are typically preferred. For further guidelines for PCR primer and probe design see, e.g., Dieffenbach, C. W. et al., General Concepts for PCR Primer Design in: PCR Primer, A Laboratory Manual, Cold Spring Harbor Laboratory Press, New York, 1995, pp. 133-155; Innis and Gelfand, Optimization of PCRs in: PCR Protocols, A Guide to Methods and Applications, CRC Press, London, 1994, pp. 5-11; and Plasterer, T. N. Primerselect: Primer and probe design. Methods Mol. Biol. 70: 520-527 (1997), the entire disclosures of which are hereby expressly incorporated by reference.

Microarray Analysis

Differential expression can also be identified, or confirmed using the microarray technique. Thus, the expression profile of disease specific markers can be measured in either fresh or paraffin-embedded tumour tissue, using microarray technology. In this method, polynucleotide sequences of interest (including cDNAs and oligonucleotides) are plated, or arrayed, on a microchip substrate. The arrayed sequences (i.e., capture probes) are then hybridized with specific polynucleotides from cells or tissues of interest (i.e., targets). Just as in the RT-PCR method, the source of RNA typically is total RNA isolated from human tumours or tumour cell lines, and corresponding normal tissues or cell lines. Thus RNA can be isolated from a variety of primary tumours or tumour cell lines. If the source of RNA is a primary tumour, RNA can be extracted, for example, from frozen or archived formalin fixed paraffin-embedded (FFPE) tissue samples and fixed (e.g., formalin-fixed) tissue samples, which are routinely prepared and preserved in everyday clinical practice.

In a specific embodiment of the microarray technique, PCR amplified inserts of cDNA clones are applied to a substrate. The substrate can include up to 1, 2, 5, 10, 15, 20, 25, 30, 35, 40, 45, 50, or 75 nucleotide sequences. In other aspects, the substrate can include at least 10,000 nucleotide sequences. The microarrayed sequences, immobilized on the microchip, are suitable for hybridization under stringent conditions. As other embodiments, the targets for the microarrays can be at least 50, 100, 200, 400, 500, 1000, or 2000 bases in length; or 50-100, 100-200, 100-500, 100-1000, 100-2000, or 500-5000 bases in length. As further embodiments, the capture probes for the microarrays can be at least 10, 15, 20, 25, 50, 75, 80, or 100 bases in length; or 10-15, 10-20, 10-25, 10-50, 10-75, 10-80, or 20-80 bases in length.

Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual colour fluorescence, separately labeled cDNA probes generated from two sources of RNA are hybridized pairwise to the array. The relative abundance of the transcripts from the two sources corresponding to each specified gene is thus determined simultaneously.

The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93 (2): 106-149 (1996)). Microarray analysis can be performed by commercially available equipment, following manufacturer's protocols, such as by using the Affymetrix GenChip technology, Illumina microarray technology or Incyte's microarray technology. The development of microarray methods for large-scale analysis of gene expression makes it possible to search systematically for molecular markers of cancer classification and outcome prediction in a variety of tumour types.

RNA Isolation, Purification, and Amplification

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56: A67 (1987), and De Sandres et al., BioTechniques 18: 42044 (1995). In particular, RNA isolation can be performed using purification kit, buffer set, and protease from commercial manufacturers, such as Qiagen, according to the manufacturer's instructions. For example, total RNA from cells in culture can be isolated using Qiagen RNeasy® "a registered trademark of Qiagen GmbH, Hilden, Germany" mini-columns Other commercially available RNA isolation kits include MasterPure Complete DNA and RNA Purification Kit (EPICENTRE (D, Madison, Wis.), and Paraffin Block RNA Isolation Kit (Ambion, Inc.). Total RNA from tissue samples can be isolated using RNA Stat-60 (Tel-Test). RNA prepared from tumour can be isolated, for example, by cesium chloride density gradient centrifugation.

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 micron thick sections of paraffin-embedded tumour tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumour sample examined Immunohistochemistry and Proteomics Immunohistochemistry methods are also suitable for detecting the expression levels of the proliferation markers of the present invention. Thus, antibodies or antisera, preferably polyclonal antisera, and most preferably monoclonal antibodies specific for each marker, are used to detect expression. The antibodies can be detected by direct labeling of the antibodies themselves, for example, with radioactive labels, fluorescent labels, hapten labels such as, biotin, or an enzyme such as horseradish peroxidase or alkaline phosphatase. Alternatively, unlabeled primary antibody is used in conjunction with a labeled secondary antibody, comprising antisera, polyclonal antisera or a monoclonal antibody specific for the primary antibody Immunohistochemistry protocols and kits are well known in the art and are commercially available.

Proteomics can be used to analyze the polypeptides present in a sample (e.g., tissue, organism, or cell culture) at a certain point of time. In particular, proteomic techniques can be used to assess the global changes of polypeptide expression in a sample (also referred to as expression proteomics). Proteomic analysis typically includes: (1) separation of individual polypeptides in a sample by 2-D gel electrophoresis (2-D PAGE); (2) identification of the individual polypeptides recovered from the gel, e.g., by mass spectrometry or N-terminal sequencing, and (3) analysis of the data using bioinformatics. Proteomics methods are valuable supplements to other methods of gene expression profiling, and can be used, alone or in combination with other methods, to detect the products of the proliferation markers of the present invention.

Hybridization Methods Using Nucleic Acid Probes Selective for a Marker

These methods involve binding the nucleic acid probe to a support, and hybridizing under appropriate conditions with RNA or cDNA derived from the test sample (Sambrook, J., E Fritsch, E. and T Maniatis, Molecular Cloning: A Laboratory Manual $3^{rd}$. Cold Spring Harbor Laboratory Press: Cold Spring Harbor (2001)). These methods can be applied to markers derived from a tumour tissue or fluid sample. The RNA or cDNA preparations are typically labeled with a fluorescent or radioactive molecule to enable detection and quantification. In some applications, the hybridizing DNA can be tagged with a branched, fluorescently labeled structure to enhance signal intensity (Nolte, F. S., Branched DNA signal amplification for direct quantitation of nucleic acid sequences in clinical specimens. Adv. Clin. Chem. 33, 201-35 (1998)). Unhybridized label is removed by extensive washing in low salt solutions such as 0.1×SSC, 0.5% SDS before quantifying the amount of hybridization by fluorescence detection or densitometry of gel images. The supports can be solid, such as nylon or nitrocellulose membranes, or consist of microspheres or beads that are hybridized when in liquid suspension. To allow washing and purification, the beads may be magnetic (Haukanes, B-1 and Kvam, C., Application of magnetic beads in bioassays. Bio/Technology 11, 60-63 (1993)) or fluorescently-labeled to enable flow cytometry (see for example: Spiro, A., Lowe, M. and Brown, D., A Bead-Based Method for Multiplexed Identification and Quantitation of DNA Sequences Using Flow Cytometry. Appl. Env. Micro. 66, 4258-4265 (2000)).

A variation of hybridization technology is the QuantiGene Plex® assay (a registered trademark of Panomics, of California, United States) (Genospectra, Fremont) which combines a fluorescent bead support with branched DNA signal amplification. Still another variation on hybridization technology is the Quantikine® mRNA assay (R&D Systems, Minneapolis). Methodology is as described in the manufacturer's instructions. Briefly the assay uses oligonucleotide hybridization probes conjugated to Digoxigenin. Hybridization is detected using anti-Digoxigenin antibodies coupled to alkaline phosphatase in colorometric assays.

Additional methods are well known in the art and need not be described further herein.

Enzyme-Linked Immunological Assays (ELISA)

Briefly, in sandwich ELISA assays, a polyclonal or monoclonal antibody against the marker is bound to a solid support (Crowther, J. R. The ELISA guidebook. Humana Press: New Jersey (2000); Harlow, E. and Lane, D., Using antibodies: a laboratory manual. Cold Spring Harbor Laboratory Press: Cold Spring Harbor (1999)) or suspension beads. Other methods are known in the art and need not be described herein further. Monoclonal antibodies can be hybridoma-derived or selected from phage antibody libraries (Hust M. and Dubel S., Phage display vectors for the in vitro generation of human antibody fragments. Methods Mol Biol. 295:71-96 (2005)). Nonspecific binding sites are blocked with non-target protein preparations and detergents. The capture antibody is then incubated with a preparation of sample or tissue from the patient containing the antigen. The mixture is washed before the antibody/antigen complex is incubated with a second antibody that detects the target marker. The second antibody is typically conjugated to a fluorescent molecule or other reporter molecule that can either be detected in an enzymatic reaction or with a third antibody conjugated to a reporter (Crowther, Id.). Alternatively, in direct ELISAs, the preparation containing the marker can be bound to the support or bead and the target antigen detected directly with an antibody-reporter conjugate (Crowther, Id.).

Methods for producing monoclonal antibodies and polyclonal antisera are well known in the art and need not be described herein further.

Immunodetection

The methods can also be used for immunodetection of marker family members in sera or plasma from bladder cancer patients taken before and after surgery to remove the tumour, immunodetection of marker family members in patients with other cancers, including but not limited to, colorectal, pancreatic, ovarian, melanoma, liver, oesophageal, stomach, endometrial, and brain and immunodetection of marker family members in urine and stool from bladder cancer patients.

Disease markers can also be detected in tissues or samples using other standard immunodetection techniques such as immunoblotting or immunoprecipitation (Harlow, E. and Lane, D., Using antibodies: a laboratory manual. Cold Spring Harbor Laboratory Press: Cold Spring Harbor (1999)). In immunoblotting, protein preparations from tissue or fluid containing the marker are electrophoresed through polyacrylamide gels under denaturing or non-denaturing conditions. The proteins are then transferred to a membrane support such as nylon. The marker is then reacted directly or indirectly with monoclonal or polyclonal antibodies as described for immunohistochemistry. Alternatively, in some preparations, the proteins can be spotted directly onto membranes without prior electrophoretic separation. Signal can be quantified by densitometry.

In immunoprecipitation, a soluble preparation containing the marker is incubated with a monoclonal or polyclonal antibody against the marker. The reaction is then incubated with inert beads made of agarose or polyacrylamide with covalently attached protein A or protein G. The protein A or G beads specifically interact with the antibodies forming an immobilized complex of antibody-marker-antigen bound to the bead. Following washing the bound marker can be detected and quantified by immunoblotting or ELISA.

Establishing a Diagnosis

Once the level of expression of IL8Rb, and optionally one or more further cancer markers, has been obtained then a diagnosis for that subject can be established. If the expression of IL8Rb is above the expression seen in subjects that do not have an inflammatory bladder disease, and/or is consistent with the level of expression in subjects known to have an inflammatory bladder disease, then the subject will be diagnosed as having an inflammatory bladder disease. Alternatively, if the expression is not above the expression seen in subjects that do not have an inflammatory bladder disease, and/or is below the levels of expression in subjects known to have an inflammatory bladder disease, then the subject will be diagnosed as not an inflammatory bladder disease.

In the situation where IL8Rb is used in conjunction with one or more markers for Bladder cancer, then the expression level of IL8Rb will be compared with the level of expression of subjects without an inflammatory bladder disease, and/or subjects known to have an inflammatory bladder disease. The one or more cancer markers are compared to the expression level in subjects without bladder cancer and/or subjects known to have bladder cancer. If the expression level of the IL8Rb is consistent with a subject that does not have an inflammatory bladder disease (less than a subject having an inflammatory bladder disease) and the expression level of the one or more bladder cancer markers are consistent with a subject having bladder cancer (differential to a subject that does not have bladder cancer), then the subject is diagnosed as having bladder cancer. If the expression level of the IL8Rb is greater than a subject that does not have an inflammatory bladder disease (consistent with a subject having an inflammatory bladder disease) and the expression level of the one or more bladder cancer markers are consistent with a subject having bladder cancer (differential to a subject that does not have bladder cancer), then the subject is diagnosed as having an inflammatory bladder disease. If the expression level of the IL8Rb is consistent with a subject that does not have an inflammatory bladder disease (less than a subject having an inflammatory bladder disease) and the expression level of the one or more bladder cancer markers are consistent with a subject that does not have bladder cancer (differential to a subject that does have bladder cancer), then the subject is diagnosed as having neither bladder cancer or an inflammatory bladder disease.

Because there is often an overlap in expression levels between the normal and disease expression of a diagnostic marker, in order to establish a diagnosis for a subject it is typical to establish a classifying threshold. A classifying threshold is a value or threshold which distinguishes subjects into disease or non disease categories. A threshold is commonly evaluated with the use of a Receiver Operating Characteristic (ROC) curve, which plots the sensitivity against specificity for all possible thresholds.

Diagnostic Threshold Determination

For tests using disease markers, diagnostic thresholds are derived that enable a sample to be called either positive or negative for the disease, e.g., bladder cancer. These diagnostic thresholds are determined by the analysis of cohorts of patients that are investigated for the presence of bladder cancer or inflammatory bladder disease. Diagnostic thresholds may vary for different test applications; for example, diagnostic thresholds for use of the test in population screening are determined using cohorts of patients who are largely free of urological symptoms, and these diagnostic thresholds may be different to those used in tests for patients who are under surveillance for bladder cancer recurrence. A diagnostic threshold is selected to provide a practical level of test specificity in the required clinical setting; that is, a specificity that allows reasonable sensitivity without excessive numbers of patients receiving false positive results. This specificity may be within the range of 80-100%.

A diagnostic threshold is determined by applying the algorithms that combine the gene expression levels of each marker to each sample from a prospective clinical trial. Samples used are from patients with bladder cancer and a range of non-malignant urological disorders. A diagnostic threshold is selected by determining the score of the algorithm that resulted in the desired specificity. For example, in some applications a specificity of 85% is desired. A diagnostic threshold is then set by selecting an algorithm score that results in 85% of patients without bladder cancer being correctly classed as negative for cancer. In other applications (such as population screening), higher specificity, such as 90%, is favoured. To set a threshold for this application, an algorithm score that results in 90% of patients without bladder cancer being correctly classed as negative for cancer is selected. Examples of the use of an algorithm is outlined in the Examples.

As an alternative to single thresholds, the test may use test intervals which provide different degrees of likelihood of presence of disease and which have different clinical consequences associated with them. For example, a test may have three intervals; one associated with a high (e.g. 90%) risk of the presence of bladder cancer, a second associated with a low risk of bladder cancer and a third regarded as being suspicious of disease. The "suspicious" interval could be associated with a recommendation for a repeat test in a defined period of time.

Data Analysis

Once the method to test for the amount of RNA and/or protein has been completed, the data then has to be analysed in order to determine the distribution of biomarker values associated with tumour and normal samples. This typically involves normalizing the raw data, ie removing background "noise" etc and averaging any duplicates (or more), comparison with standards and establishing cut-offs or thresholds to optimally separate the two classes of samples. Many methods are known to do this, and the exact method will depend on specific method for determining the amount of RNA and/or protein used.

Below is an example of how the data analysis could be preformed when using qRT-PCR. However, it will be appreciated the general process could be adapted to be used for other methods of establishing the RNA and/or protein content, or other methods could be established by someone skilled in the art to achieve the same result.

Data

Measurements of fluorescence are taken at wavelengths $\omega_i$ i=1,2 at each cycle of the PCR. Thus for each well we observe a pair of fluorescence curves, denoted by $f_t(\omega_i)$, where t=1, . . . , k denotes cycle number and i=1,2 indexes the wavelengths.

Fluorescence curves have a sigmoidal shape beginning with a near horizontal baseline and increasing smoothly to an upper asymptote. The location of a point $C_p$ where the fluorescence curve departs from the linear baseline will be used to characterize the concentration of the target gene. A precise definition of $C_p$ follows later.

The following is an example of a scheme to process these data.

Compensate for fluorescence overlap between frequency bands,
Estimate a smooth model for each fluorescence curve in order to estimate $C_p$
Combine data from replicated wells.
Estimate standard curves
Compute a concentration relative to the standard.

Each biological sample yields relative concentrations of 5 genes, which are the inputs to the discriminant function.

Colour Compensation

Denote the level of fluorescence of dye $j$ at cycle t and frequency $\omega$ by $W_{tj}(\omega)$. In a multiplexed assay the measured response at any frequency $\omega$ is the sum of contributions from all dyes at that frequency, so for each cycle $$f_t(\omega) = W_{t1}(\omega) + W_{t2}(\omega) + \ldots$$

The purpose of colour compensation is to extract the individual contributions $W_{tj}(\omega)$, from the observed mixtures $f_t(\omega)$.

In the ideal situation, fluorescence $W_{tj}(\omega_o)$, due to dye j at a frequency $\omega$ is proportional to its fluorescence $W_{tj}(\omega_o)$ at reference frequency $\omega_o$, regardless of the level of $W_{tj}(\omega_o)$. This suggests the linear relationship $$\begin{bmatrix} f_t(\omega_1) \\ f_t(\omega_2) \end{bmatrix} = \begin{bmatrix} W_{t1}(\omega_1) + W_{t2}(\omega_1) \\ W_{t1}(\omega_2) + W_{t2}(\omega_2) \end{bmatrix} = \begin{bmatrix} 1 & A_{12} \\ A_{21} & 1 \end{bmatrix} \begin{bmatrix} W_{t1}(\omega_1) \\ W_{t2}(\omega_2) \end{bmatrix}$$

for some proportionality constants $A_{12}$ and $A_{21}$ that are to be determined. In reality, there are additional effects, which are effectively modelled by introducing linear terms in this system, so $$\begin{bmatrix} f_t(\omega_1) \\ f_t(\omega_2) \end{bmatrix} = \begin{bmatrix} 1 & A_{12} \\ A_{21} & 1 \end{bmatrix} \begin{bmatrix} W_{t1}(\omega_1) \\ W_{t2}(\omega_2) \end{bmatrix} \begin{bmatrix} a_1 + b_1 t \\ a_2 + b_2 t \end{bmatrix}$$

After estimating the "colour compensation" parameters $A_{12}$ and $A_{21}$ we can recover $W_{t1}(\omega_1)$ and $W_{t2}(\omega_2)$, albeit distorted by a linear baseline, by matrix multiplication:

$$\begin{bmatrix} W_{t1}(\omega_1) \\ W_{t2}(\omega_2) \end{bmatrix} \begin{bmatrix} 1 & A_{12} \\ A_{21} & 1 \end{bmatrix}^{-1} \begin{bmatrix} f_t(\omega_1) \\ f_t(\omega_2) \end{bmatrix} + \begin{bmatrix} a_1^* + b_1^* t \\ a_2^* + b_2^* t \end{bmatrix}$$

The $W_{t1}(\omega_1)$ and $W_{t2}(\omega_2)$ will be called "colour compensated" data. The linear distortions $a_i^* + b_i^* t$ in the last term of this expression will be accommodated in the baseline estimate when estimating a model for the colour compensated data below 2. It has no influence on the estimate of $C_p$.

Estimation of the colour compensation coefficients requires a separate assay using single (as opposed to duplex) probes. Then $W_{t2}(\omega_2)=0$ giving $$\begin{bmatrix} f_t(\omega_1) \\ f_t(\omega_2) \end{bmatrix} = \begin{bmatrix} 1 & A_{12} \\ A_{21} & 1 \end{bmatrix} \begin{bmatrix} W_{t1}(\omega_1) \\ 0 \end{bmatrix} + \begin{bmatrix} a_1 + b_1 t \\ a_2 + b_2 t \end{bmatrix}$$

Thus $$f_t(\omega_2) = A_{21} f_t(\omega_1) + a^* + b^* t$$

Now the coefficient $A_{21}$ can be estimated by ordinary linear regression of $f_t(\omega_2)$ on $f_t(\omega_1)$ and PCR cycle t for t=1, . . . , k.

Model Estimation

In this section, let $y_t$ t=1, . . . , k denote a colour compensated fluorescence curve.

Amplification

Models are only estimated for fluorescence curves that show non-trivial amplification. We define the term "amplification" as a non-trivial departure from the linear baseline of the colour compensated fluorescence curve. Use signal to noise ratio (SNR) to quantify amplification. Here SNR is defined as the ratio of signal variance to noise variance. Noise variance is set as part of calibration of the assay procedure and remains unchanged: for this purpose, use the residual variance from a linear model for the baseline from wells that can have no amplification, i.e. wells without RNA. For each fluorescence curve, estimate the signal variance as the residual variance from the best fitting straight line (Here "best" is meant in the least squares sense.)

If SNR is less than a specified threshold, the fluorescence curve is close to linear and no amplification is present. Then there is no point of departure from the baseline and the concentration in the sample may be declared as zero.

If the SNR is above the threshold, amplification is present and a concentration can be estimated.

Thresholds for the (dimensionless) SNR are selected to provide clear discrimination between "amplified" and "non amplified" curves. For example, the following ranges for thresholds are effective for the markers.

| Fluor | Gene | Range |
|-------|------|-------|
| JOE | MDK | 40-120 |
| JOE | CDC | 35-70 |
| JOE | IL8R | 30-60 |
| FAM | IGF | 50-80 |
| FAM | HOXA | 50-150 |
| FAM | XENO | 50-80 |

Model

Estimate a sigmoidal model for each fluorescence curve. Any suitable parametric form of model can be used, but it must be able to model the following features:

linear baseline that may have a non-zero slope,
asymmetries about the mid point.
asymptotes at lower and upper levels
smooth increase from baseline to upper asymptote An example of a model that achieves these requirements is $$g_t(\theta) = A + A_s t + \frac{D}{\left(1 + \left(\frac{t}{B}\right)^E\right)^F}$$

We call this the "6PL model". The parameter vector $\theta = [A, A_s, D, B, E, F]$ is subject to the following constraints to ensure that $g_t(\theta)$ is an increasing function of t and has the empirical properties of a fluorescence curve.

$$D > 0, B > 0, E < 0, F < 0$$

The other two parameters determine the base line $A + A_s t$, and these parameters do not need explicit constraints though A is always positive and the slope parameter $A_s$ is always small.

The parameter D determines the level of amplification above the baseline. The remaining parameters B,E,F have no intrinsic interpretation in themselves but control the shape of the curve. These parameters are also the only parameters that influence the estimate of $C_p$. When $A_s = 0$ this is known as the five-parameter logistic function (5PL) and if, in addition, F=1 this model reduces four-parameter logistic model (4PL), Gottschalk and Dunn (2005), Spiess et al. (2008).

Initialization

Initial values for non-linear estimation are set as $A_s = 0$, $F = 1$
$A = \text{mean} (y, \ldots, y_5)$
$D = \text{range} (y_1, \ldots, y_k)$
B=cycle corresponding to half height
E is initialized by converting $g_t(\theta)$ into a linear form having set the values of the remaining parameters to their initial values defined above. Linearization obtains $$E \log\left(1 + \frac{t}{B}\right) = \log\left(\frac{D}{y_t - A}\right)$$

Now estimate E by regression of $$\log\left(\frac{D}{y_t - A}\right)_{on} \log\left(1 + \frac{t}{B}\right)$$

for t selected so that $$A + \frac{D}{10} < y_t < A + \frac{9D}{10}$$

An alternative form of this model that leads to an almost identical analysis (with its own initialization) is $$A + A_1 st + D/(1 + \exp((tB)/E)^t F$$

When $A_s = 0$ this is sometimes known as the Richards equation, Richards (1959)

Estimation Criterion

Estimate parameters to minimize a penalized sum of squares criterion $$\sum_t (y_t - g_t(\theta))^2 + \lambda(\theta)$$

Here $\lambda(\theta)$ is a non-negative function that penalizes large values of some (or all) of the parameters in $\theta$. This method is known as regularization or ridge regression (Hoerl, 1962) and may be derived from a Bayesian viewpoint by setting a suitable prior distribution for the parameter vector $\theta$. A satisfactory choice for the penalty is $$\lambda(\theta) = \lambda(B^2 + D^2 + E^2 + F^2).$$

Large values of $\lambda$ bias the parameter estimates towards zero and reduce the variance of the parameter estimates. Conversely, small (or zero) $\lambda$ leads to unstable parameter estimates and convergence difficulties in minimization algorithms. The choice of $\lambda$ is a compromise between bias and variance or stability. Empirical evidence shows that a satisfactory compromise between bias and variance may be achieved if $\lambda$ is chosen in the range $$0.01 > \lambda > 0.0001.$$

This choice also ensures convergence of the optimization algorithm.

Algorithm Choice

For any choice of $\lambda$ in the above range, the description in the previous paragraph completely defines the parameter estimates. A non-linear least squares procedure based on the classical Gauss-Newton procedure (such as the Levenberg-Marquardt algorithm as implemented in More, 1978) has been successfully used and is a suitable approach. General purpose optimizing algorithms such as Nelder and Mead, 1965, or Broyden-Fletcher algorithm as implemented by Byrd, et al., 1995) have also been successfully trialed in this context.

$C_p$ Estimate $C_p$ is the point t that maximizes the second derivative of $g_t(\theta)$. Each fluorescence curve yields a $C_p$ that characterizes the concentration of the target gene. The average of the estimated $C_p$'s for each set of technical replicates is computed and used in the subsequent analysis.

1. Standard Curves

Absolute or relative concentrations are derived from a comparison with standard curves on the same PCR plate.

Model dilution series using the linear model $$C_p = R + S \log_{10} \text{Conc}$$

where Conc is an absolute or relative concentration of the standard. The intercept and slope parameters are plate specific. Model the between-plate variability in the intercept and slope parameters by setting population models $$R \sim N(\mu_R, \sigma_R^2)$$

$$S \sim N(\mu_S, \sigma_S^2)$$

where the parameters $\mu_R, \sigma_R^2, \mu_S, \sigma_S^2$ are set on the basis of prior data as described below. Then for a given plate R and S can be interpreted as observations from these populations.

For replicate i of standard at concentration $\text{Conc}_j$ the following model can be used $$C_p(i,j) = R + S \log_{10} \text{Conc}_j + \in_{ij}$$

where $\in_{ij} \sim N(0, \sigma_j^2)$. Note that the variance of the residuals depends on $C_p$. Empirical estimates of $\text{Var}(\in_{ij})$ are given in Table 2. Estimate the parameters R and S using by maximizing the likelihood function. Interpret the slope parameter in terms of the efficiency of the PCR process through $$S = -\frac{1}{\log_{10} \text{Efficiency}}$$

This model has a Bayesian interpretation: Give vague (non-informative) prior distributions to the parameters $\mu_R, \sigma_R^2, \mu_S, \sigma_S^2$. Then the population models for R and S and for $C_p(i,j)$ fully determine a probability model for the prior data. A Markov chain Monte Carlo (MCMC) algorithm (Lunn et al., 2009) allows estimation of $\mu_R, \sigma_R^2, \mu_S, \sigma_S^2$. If the prior distribution is omitted, a traditional frequentist interpretation results. Following this estimation procedure it is possible to obtain the gene-dependent population parameter estimates in Table 3.

TABLE 2

Variance of residuals

| $C_p$ | $\sigma^2$ |
|---|---|
| 12 | 0.0100 |
| 13 | 0.0108 |
| 14 | 0.0119 |
| 15 | 0.0134 |
| 16 | 0.0155 |
| 17 | 0.0184 |
| 18 | 0.0224 |
| 19 | 0.0279 |
| 20 | 0.0356 |
| 21 | 0.0466 |
| 22 | 0.0625 |
| 23 | 0.0860 |
| 24 | 0.1212 |
| 25 | 0.1750 |
| 26 | 0.2591 |
| 27 | 0.3931 |
| 28 | 0.6112 |
| 29 | 0.9741 |

TABLE 3

Population parameters for slopes and intercepts of standard curves.

| | $\mu_R$ | $\sigma_R^2$ | $\mu_S$ | $\sigma_S^2$ |
|---|---|---|---|---|
| MDK | 19.49 | 0.5112 | −3.426 | 0.0481 |
| CDC | 18.91 | 0.2343 | −3.414 | 0.0198 |
| IL8R | 31.43 | 0.0919 | −3.192 | 0.0017 |
| IGF | 20.63 | 0.3835 | −3.275 | 0.0247 |
| HOXA | 22.51 | 0.1544 | −3.270 | 0.0037 |

The estimates of intercept and slope of the standard curve are denoted by $\hat{R}$ and $\hat{S}$.

2. Relative Concentrations $\Delta C_p$

Use the standard curve to compute $C_{p(REF)}$ at the concentration $\text{Conc}_{REF}$ from $$C_{p(REF)} = \hat{R} + \hat{S} \log_{10} \text{Conc}_{REF}$$

The relative concentration of a sample is given by $$\Delta C_p = \frac{C_p - C_{p(REF)}}{\hat{S}} = \log_{10} \frac{\text{Conc}_{SAMPLE}}{\text{Conc}_{REF}}$$

Alternatively $\hat{S}$ may be approximated at a fixed level corresponding to a PCR efficiency of 2. Then $\hat{S} = -1/\log_{10}(2) = -3.32$. Use the same notation $\Delta C_P$ for either choice. The resulting $\Delta C_P$ estimates, one for each gene, are inputs to the discriminant function in the next step.

3. Discriminant Function

The $\Delta C_P$ values correspond to a relative biomarker value with plate-to-plate variation removed. Examination of the 5 $\Delta C_P$ values in comparison with each other (for example, see FIG. 2), shows how tumor samples typically have different biomarker values than non-tumor samples. Furthermore, while there is overlap in the areas for tumor and normal, a large number of samples are effectively well separated. Under these circumstances, many different statistical classifiers could be used to separate the normal from the tumor samples. We show here that a sample of several classifiers do work to separate these samples. We used 5 different classification methods: 1) Linear Discriminant Analysis (LDA), 2) Logistic Regression (Log Reg); 3) Support Vector Machines (SVM); 4) K-nearest-neighbor (KNN) based on 5 neighbors (KN5N); and 5) Recursive partitioning trees (TREE) (Cite: Venables & Ripley and Dalgaard).

Creation of a classifier requires a dataset containing the biomarker values for a large number of samples which should represent the ultimate population to be tested by the classifier. For example, if a classifier is to be used for screening an at-risk population (eg age 50 and older, smokers), then the set of data required for creating the classifier (called the "training set") should mirror that population and contain only samples from people older than 50 who smoke. Typically to obtain measurement precision of smaller than 10% error for parameters like sensitivity and specificity, the training set needs to be larger than 300 samples.

Estimation of the effectiveness of a classifier can be made using cross-validation. In cross-validation (Wikipedia: Cross-validation), the dataset is divided into a small number of equally sized partitions (typically 3 to 10). One section is left out and the remaining sections used to build a classifier; then the left out section is tested by the new classifier and its predictions noted. This is done for each section in turn and all the predictions combined and analysed to compute the characteristics of the classifier:

Sensitivity, Specificity, etc. If the cross-validation is performed by partitioning the data into 10 parts, it is called 10-fold cross-validation; similarly, 3 parts would be 3-fold cross-validation. If the data are partitioned into as many classes are there are samples, this is called "leave one out cross-validation". By testing on data not used to build the classifier, this method provides an estimate of the classifier performance in the absence of additional samples.

We have built classifiers using all 15 combinations of the 4 biomarkers, MDK, IGFBP5, CDC2, and HOXA13, all with and without the IL8Rb biomarker, using the clinical trial dataset described elsewhere in this document (Example 1) and tested those 30 classifiers using 10-fold cross-validation. This was done for each of the 5 classifier types listed above and the ROC curves computed. All work was performed using the R Statistical Programming Environment (CITE). These results (FIG. 14) show that in most cases, the classifier with IL8Rb is more sensitive for values of specificity which are useful diagnostically (False Positive Rate of 0 to 20%; Specificity from 100 to 80%). The Area Under the Curve (AUC) for the region with diagnostic utility of specificities is used to quantify how well classifiers perform with larger values indicating better classifier performance FIG. 15a tabulates the AUC for each classifier and biomarker combination, while FIG. 15b shows the amount of increase in AUC for each condition when IL8Rb is added. In most cases, the addition of IL8Rb improves the ability to make accurate diagnoses Specific sensitivity values for diagnostically useful specificity values are tabulated for all the classifiers in FIG. 16. In addition, FIG. 17 tabulates the amount of gain in sensitivity or specificity which the addition of IL8Rb provides.

The utility of the classifier is created when, having created it and tested it, it is used to test a new sample. To simplify the interpretation of results, a cut-off score or threshold is established; samples on one side of the cut-off are considered positive and on the other side, negative for tumors. Additional cut-offs may be established for example to indicate increasing levels of certainty of results. In this case, we have established a cut-off which gives a false positive rate of 15% in our training set. Using our cross-validated ROC curves, we can then estimate our sensitivity. Typically, we also establish a cut-off at a positive predictive value of 75%. To use these cut-offs we establish a "negative" result for scores less than the cut-off established by the 85% specificity. Scores greater than the 75% PPV are called "positive" and score between the two are called "indeterminate" or "suspicious".

Antibodies to IL8Rb Marker

In additional aspects, this invention includes manufacture of antibodies against IL8Rb. The marker IL8Rb can be produced in sufficient amount to be suitable for eliciting an immunological response. In some cases, a full-length IL8Rb can be used, and in others, a peptide fragment of a IL8Rb may be sufficient as an immunogen. The immunogen can be injected into a suitable host (e.g., mouse, rabbit, etc) and if desired, an adjuvant, such as Freund's complete adjuvant or Freund's incomplete adjuvant can be injected to increase the immune response. It can be appreciated that making antibodies is routine in the immunological arts and need not be described herein further. As a result, one can produce antibodies, including monoclonal or phage-display antibodies, against IL8Rb.

In yet further embodiments, antibodies can be made against the protein or the protein core of the tumour markers identified herein or against an oligonucleotide sequence unique to a IL8Rb. Although certain proteins can be glycosylated, variations in the pattern of glycosylation can, in certain circumstances, lead to mis-detection of forms of IL8Rb that lack usual glycosylation patterns. Thus, in certain aspects of this invention, IL8Rb immunogens can include deglycosylated IL8Rb or deglycosylated IL8Rb fragments. Deglycosylation can be accomplished using one or more glycosidases known in the art. Alternatively, IL8Rb cDNA can be expressed in glycosylation-deficient cell lines, such as prokaryotic cell lines, including E. coli and the like.

Vectors can be made having IL8Rb-encoding oligonucleotides therein. Many such vectors can be based on standard vectors known in the art. Vectors can be used to transfect a variety of cell lines to produce IL8Rb-producing cell lines, which can be used to produce desired quantities of IL8Rb for development of specific antibodies or other reagents for detection of IL8Rb or for standardizing developed assays for IL8Rb.

Kits

Based on the discoveries of this invention, several types of test kits can be envisioned and produced. First, kits can be made that have a detection device pre-loaded with a detection molecule (or "capture reagent"). In embodiments for detection of IL8Rb mRNA, such devices can comprise a substrate (e.g., glass, silicon, quartz, metal, etc) on which oligonucleotides as capture reagents that hybridize with the mRNA to be detected is bound. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Antibodies can also be used in kits as capture reagents. In some embodiments, a substrate (e.g., a multiwell plate) can have a specific IL8Rb and BTM capture reagents attached thereto. In some embodiments, a kit can have a blocking reagent included. Blocking reagents can be used to reduce non-specific binding. For example, non-specific oligonucleotide binding can be reduced using excess DNA from any convenient source that does not contain IL8Rb and BTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect marker associated molecules can be used and be considered within the scope of this invention.

Antibodies can also be used when bound to a solid support, for example using an antibody chip, which would allow for the detection of multiple markers with a single chip.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Detection of IL8Rb and BTMs in a sample can be preformed using any suitable technique, and can include, but are not limited to, oligonucleotide probes, qPCR or antibodies raised against cancer markers.

It will be appreciated that the sample to be tested is not restricted to a sample of the tissue suspected of being an inflammatory disease or tumour. The marker may be secreted into the serum or other body fluid. Therefore, a sample can include any bodily sample, and includes biopsies, blood, serum, peritoneal washes, cerebrospinal fluid, urine and stool samples.

It will also be appreciated that the present invention is not restricted to the detection of cancer in humans, but is suitable for the detection of cancer in any animal, including, but not limited to dogs, cats, horses, cattle, sheep, deer, pigs and any other animal known to get cancer.

General Tests for Inflammatory Disease or Cancer Markers in Body Fluids

In general, methods for assaying for oligonucleotides, proteins and peptides in these fluids are known in the art. Detection of oligonucleotides can be carried out using hybridization methods such as Northern blots, Southern blots or microarray methods, or qPCR. Methods for detecting proteins include such as enzyme linked immunosorbent assays (ELISA), protein chips having antibodies, suspension beads radioimmunoassay (RIA), Western blotting and lectin binding. However, for purposes of illustration, fluid levels of a disease markers can be quantified using a sandwich-type enzyme-linked immunosorbent assay (ELISA). For plasma assays, a 5 uL aliquot of a properly diluted sample or serially diluted standard marker and 75 uL of peroxidase-conjugated anti-human marker antibody are added to wells of a microtiter plate. After a 30 minute incubation period at 30° C., the wells are washed with 0.05% Tween 20 in phosphate-buffered saline (PBS) to remove unbound antibody. Bound complexes of marker and anti-marker antibody are then incubated with o-phenylendiamine containing $H_2O_2$ for 15 minutes at 30° C. The reaction is stopped by adding 1 M $H_2SO_4$, and the absorbance at 492 nm is measured with a microtiter plate reader.

It can be appreciated that anti-IL8Rb antibodies can be monoclonal antibodies or polyclonal antisera. It can also be appreciated that any other body fluid can be suitably studied.

It is not necessary for a marker to be secreted, in a physiological sense, to be useful. Rather, any mechanism by which a marker protein or gene enters the serum can be effective in producing a detectable, quantifiable level of the marker. Thus, normal secretion of soluble proteins from cells, sloughing of membrane proteins from plasma membranes, secretion of alternatively spliced forms of mRNA or proteins expressed therefrom, cell death (either apoptotic) can produce sufficient levels of the marker to be useful.

There is increasing support for the use of serum markers as tools to diagnose and/or evaluate efficacy of therapy for a variety of cancer types.

Yoshikawa et al., (Cancer Letters, 151: 81-86 (2000) describes tissue inhibitor of matrix metalloproteinase-1 in plasma of patients with gastric cancer.

Rudland et al., (Cancer Research 62: 3417-3427 (2002) describes osteopontin as a metastasis associated protein in human breast cancer.

Buckhaults et al., (Cancer Research 61:6996-7001 (2002) describes certain secreted and cell surface genes expressed in colorectal tumours.

Kim et al., (JAMA 287(13):1671-1679 (2002) describes osteopontin as a potential diagnostic biomarker for ovarian cancer.

Hotte et al., (AJ. American Cancer Society 95(3):507-512 (2002) describes plasma osteopontin as a protein detectable in human body fluids and is associated with certain malignancies.

Martin et al., (Prostate Cancer Prostatic Dis. Mar. 9, 2004 (PMID: 15007379) (Abstract) described use of human kallikrein 2, prostate-specific antigen (PSA) and free PSA as markers for detection of prostate cancer.

Hall et al (Laryngoscope 113(1):77-81 (2003) (PMID: 12679418) (Abstract) described predictive value of serum thyroglobulin in thyroid cancer.

Mazzaferri et al., (J. Clin. Endocrinol. Metab. 88(4):1433-1441 (2003) (Abstract) describes thyroglobulin as a potential monitoring method for patients with thyroid carcinoma.

Whitley et al, (Dim Lab. Med. 24(1):29-47 (2004) (Abstract) describes thyroglobulin as a serum marker for thyroid carcinoma.

Kuo et al (Clin. Chim Acta. 294(1-2):157-168 (2000) (Abstract) describes serum matrix metalloproteinase-2 and -9 in HCF- and HBV-infected patients.

Koopman et al., (Cancer Epidemiol. Biomarkers Prev 13(3): 487-491 (2004) (Abstract) describes osteopontin as a biomarker for pancreatic adenocarcinoma.

Pellegrini et al., (Cancer Immunol. Immunother. 49(7):388-394 (2000) (Abstract) describes measurement of soluble carcinoembryonic antigen and TIMP 1 as markers for pre-invasive colorectal cancer.

Melle et al., (Clin. Chem. 53(4), 629-635 (2007) (Abstract) describes HSP27 as a serum marker for pancreatic adenocarcinoma.

Leman et al., (Urology, 69(4) 714-20 (2007) (Abstract) describes EPCA-2 as a serum marker for prostate cancer.

Tsigkou et al., (I Clin Endocrinol Metab, 92(7) 2526-31 (2007) (Abstract) describes total inhibin as a potential serum marker for ovarian cancer.

Marchi et al., (Cancer 112, 1313-1324 (2008) (Abstract) describes ProApolipoprotein Al as a serum marker of brain metastases in lung cancer patients.

EXAMPLES

The examples described herein are for purposes of illustrating embodiments of the invention. Other embodiments, methods and types of analyses are within the scope of persons of ordinary skill in the molecular diagnostic arts and need not be described in detail hereon. Other embodiments within the scope of the art are considered to be part of this invention.

Example 1

Methods

Patients: Between April 2008 and September 2009, 471 patients presenting with macroscopic haematuria, but no prior history of urinary tract malignancy, were recruited at eleven urology clinics in New Zealand and Australia. Each patient provided a urine sample immediately prior to undergoing cystoscopy and any additional diagnostic procedures. A diagnosis was made by three months following enrollment in the study. Of these 471 patients, gene expression data on all five study genes was successfully obtained for 442 patients using the methods described below. The characteristics of these patients are shown in Table 4.

TABLE 4

Characteristics of the study population. The table shows the number of patients in each of the main diagnostic categories at three months after the patient's initial presentation with gross hematuria.

| Diagnosis | Number |
| --- | --- |
| Benign prostatic hyperplasia | 18 |
| Cystitis | 18 |
| Exercise-induced hematuria | 3 |
| Non-specific kidney disease | 3 |
| Non-specific neoplasia | 3 |
| Non-specific prostate disease | 63 |
| Vascular prostate | 49 |

TABLE 4-continued

Characteristics of the study population. The table shows the number of patients in each of the main diagnostic categories at three months after the patient's initial presentation with gross hematuria.

| Diagnosis | Number |
| --- | --- |
| Other urological cancer (non-TCC) | 5 |
| Superficial vessels | 3 |
| Urethral stricture | 6 |
| Urinary tract infection | 18 |
| Urolithiasis | 25 |
| Warfarin use | 10 |
| Unknown etiology | 155 |
| Miscellaneous | 7 |
| TCC | 56 |
| Total | 442 |

Urine Analysis:

Urine samples were analysed by central review cytology (Southern Community Laboratories, Dunedin, New Zealand). The diagnostic tests NMP22 BladderChek (Matritech) and NMP22 ELISA (Matritech) were carried out according to the manufacturer's instructions at the clinical site (BladderChek) or by Southern Community Laboratories (NMP22 ELISA).

RNA Quantification:

2 mls or urine from each patient was mixed with RNA extraction buffer containing 5.64M guanidine thiocyanate, 0.5% sarkosyl and 50 mM NaoAc pH6.5. Total RNA was then extracted by Trizol extraction (Invitrogen) and the RNeasy procedure (Qiagen), as previously described1. RNA was eluted from the columns in 35 ul water and 3 ul was used in each subsequent monoplex or duplex quantitative reverse transcription polymerase chain reaction (qRT-PCR) assay. Each 16 ul qRT-PCR reaction contained 0.3 U RNAse-OUT (Invitrogen), 0.225 uM each Taqman probe, 1.25 U Superscript III (Invitrogen), 0.275 uM each primer, 1.5 U Fast Start Taq polymerase (Roche), 10 mM DTT, 0.375 mM dNTPs, 4.5 mM MgSO4, 1.6 ul 10× Fast Start PCR buffer (Roche) and 2.6 ul GC Rich solution (Roche). Primers and fluorescently dual-labeled probes were obtained from Integrated DNA Technologies (Coralville USA) for each of the five study genes: MDK, CDC2, HOXA13, IGFBP5 and IL8Rb. Primer/probe sequences are shown in Table 2. Reactions were set up in 96 well plates and cycled as follows on a Roche Light Cycler® 480: 50° C., 15 mins; 95° C. 8 mins; 10 cycles of 95° C. 15 sec, 60° C. 2 mins and 30 cycles of 95° C. 15 secs, 60° C. 1 min. Standard curves of 1/16 serial dilutions of a reference RNA (derived from pooled cell line RNAs) were included on each plate to generate range of 0.3 pg/ul to 20 ng/μl. Data was collected at the extension phase of the final 30 thermocycles and exported as a raw text file.

TABLE 5

Primer and probe sequences used for the qRT-PCR quantification of the five RNA markers.

| Marker | Forward Seq | Reverse Seq | Probe |
| --- | --- | --- | --- |
| MDK | TGC ACC CCC AAG ACC AAA (Seq ID No 3) | TGA TTA AAG CTA ACG AGC AGA CAG AA (Seq ID No 4) | CCT TCC CTT TCT TGG CTT TGG CCT TT (Seq ID No 5) |
| IGFBP5 | CGT TGT ACC TGC CCA ATT GTG A (Seq ID No 6) | GGG ACG CAT CAC TCA ACG TT (Seq ID No 7) | AAG AGA AAG CAG TGC AAA CCT TCC CGT (Seq ID No 8) |
| CDC2 | GCC GCC GCG GAA TAA T (Seq ID No 9) | TGT CTA CCC TTA TAC ACA ACT CCA TAG G (Seq ID No 10) | AGC CGG GAT CTA CCA TAC CCA TTG ACT AAC T (Seq ID No 11) |
| HOXA13 | TGG AAC GGC CAA ATG TAC TG (Seq ID No 12) | TGG CGT ATT CCC GTT CAA GT (Seq ID No 13) | ACT CTG CCC GAC GTG GTC TCC CA (Seq ID No 14) |
| IL8Rb | CCT TGA GGC ACA GTG AAG ACA TC (Seq ID No 15) | CCT GTA GGA CAC CTC CAG AAG AG (Seq ID No 16) | TGG CCA CTC CAA TAA CAG CAG GTC ACA (Seq ID No 17) | qRT-PCR Data Analysis:

Raw fluorescence data was exported from the Roche LightCycler® 480 as a tab-delimited file containing cycle number versus two channels of fluorescence data for all wells on the plate. The data were processed using an R program that applied colour compensation ([Bemard1999]) to the data to correct for bleed over from one fluorescent channel into another. It then fitted a 5-point logistic model to estimate the $C_P$ using the second derivative maximum ([Spiess2008]).

All samples and controls were applied in duplicate to the PCR plates. The $C_P$ values from the duplicate wells were averaged before use. If the difference between the two $C_P$ values exceeded 3 units, that sample was repeated. To provide standardization across PCR plates, $C_P$'s were expressed as $\Delta C_P$'s relative to a reference RNA (derived from pooled cell line RNAs) at 20 ng/μl:

$$\Delta C_P = C_P(\text{sample}) - C_P(\text{reference RNA})$$

Statistical Analysis:

qRT-PCR $\Delta C_P$ values from MDK, CDC2, HOXA13, IGFBP5 and IL8Rb were used to generate classifiers to separate samples containing TCCs from samples containing no TCCs, based on Linear Discriminant Analysis or Logistic Regression ([Venables2002]). In both cases, interactions between genes were permitted in the classifier models. The generation of the LDA followed standard procedures, as described, for example in "Modern Applied Statistics with S, 4th edition" by W. N. Venables and B. D. Ripley (2002), Springer. The dataset from the study was cleaned of any incomplete data then the R Statistical Environment (R Development Core Team (2009) and the function "lda" from the package MASS (Venables and Ripley (2002)) were used to generate and test the linear discriminant on the clinical trial data.

The generation of the Logistic Regression classifier was performed in a similar manner to the generation of the LDA. Again, the study data was cleaned of incomplete data. A logistic regression classifier was created using R; no additional packages were required. Logistic regression was performed as described by Dalgaard (2008). Comparison among classifiers was made using ROC curves, using the R package, ROCR (Sing et al. 2009). Confidence intervals for ROC curves were generated using the methods of Macskassy et al ([Macskassy2005]).

The following algorithms were generated:

Linear Discriminant Classifier

The first classifier, a linear discriminant, (called LDA-3), is based on five gene values (normalized to a Reference value by subtracting the reference value) allowing for multiway interactions between the genes. The classifier was built in R using the 'lda( )' function from the package called "MASS". (R version 2.9.1; MASS version 7.2-49). The classifier was built using the following equation:

lda3←lda(TCC.YN~MDK*IGF*CDC*HOXA*IL8R, data=uRNA.Trial), where lda3 is the created model; TCC.YN is the true value for "presence of TCC in urine" as determined by our gold-standard, cystoscopy; MDK, IGF, CDC, HOXA and IL8R are the normalized gene Cp value; and uRNA.Trial is a data frame contain the values for the genes and TCC.YN from the clinical trial. Use of the ASTERISK (*) in the formula does not signify multiplication, but rather means "interacting terms" in the classifier.

Evaluation of the classifier score takes as input a new data frame containing the five gene values as well as the classifier, lda3, to output a classifier score:

score←c(predict(lda3, new.data)$x)

where score is the output used from the classifier to predict the presence of TCCs; lda3 is the classifier created above and new.data is a data frame containing the measured values of the five genes called by the same names as used in classifier creation. The syntax, '$x' and c( ), is present to extract the score specifically from the large amount of information returned by the predict function.

Setting the score cut off to 0.112 and above, sets our specificity to 85% for presence of TCCs in the urine sample.

The coefficients for LDA-3 are:

| | |
|---|---|
| MDK.d.R100 | 5.333639e+00 |
| IGF.d.R100 | 3.905978e+00 |
| CDC.d.R100 | 6.877143e−01 |
| HOXA.d.R100 | 6.073742e+00 |
| IL8R.d.R100 | −1.229466e+00 |
| MDK.d.R100:IGF.d.R100 | −7.420480e−01 |
| MDK.d.R100:CDC.d.R100 | −2.611158e−01 |
| IGF.d.R100:CDC.d.R100 | −1.965410e−01 |
| MDK.d.R100:HOXA.d.R100 | −8.491556e−01 |
| IGF.d.R100:HOXA.d.R100 | −4.037102e−01 |
| CDC.d.R100:HOXA.d.R100 | −3.429627e−01 |
| MDK.d.R100:IL8R.d.R100 | 1.903118e−01 |
| IGF.d.R100:IL8R.d.R100 | 2.684005e−01 |
| CDC.d.R100:IL8R.d.R100 | −1.229809e−01 |
| HOXA.d.R100:IL8R.d.R100 | 2.909062e−01 |
| MDK.d.R100:IGF.d.R100:CDC.d.R100 | 4.108895e−02 |
| MDK.d.R100:IGF.d.R100:HOXA.d.R100 | 7.664999e−02 |
| MDK.d.R100:CDC.d.R100:HOXA.d.R100 | 4.832034e−02 |
| IGF.d.R100:CDC.d.R100:HOXA.d.R100 | 2.116340e−02 |
| MDK.d.R100:IGF.d.R100:IL8R.d.R100 | −3.750854e−02 |
| MDK.d.R100:CDC.d.R100:IL8R.d.R100 | 1.664612e−02 |
| IGF.d.R100:CDC.d.R100:IL8R.d.R100 | 2.089442e−03 |
| MDK.d.R100:HOXA.d.R100:IL8R.d.R100 | −1.539486e−02 |
| IGF.d.R100:HOXA.d.R100:IL8R.d.R100 | −3.894153e−02 |
| CDC.d.R100:HOXA.d.R100:IL8R.d.R100 | 6.295032e−03 |
| MDK.d.R100:IGF.d.R100:CDC.d.R100:HOXA.d.R100 | −4.359738e−03 |
| MDK.d.R100:IGF.d.R100:CDC.d.R100:IL8R.d.R100 | −2.019317e−04 |
| MDK.d.R100:IGF.d.R100:HOXA.d.R100:IL8R.d.R100 | 3.746882e−03 |
| MDK.d.R100:CDC.d.R100:HOXA.d.R100:IL8R.d.R100 | −2.902150e−03 |
| IGF.d.R100:CDC.d.R100:HOXA.d.R100:IL8R.d.R100 | 4.799489e−04 |
| MDK.d.R100:IGF.d.R100:CDC.d.R100:HOXA.d.R100:IL8R.d.R100 | 7.512308e−05 |

Logistic Regression Classifier

A second classifier based on Logistic Regression was derived from the same cleaned dataset as LDA-3. Instead of using the lda( ) function, however, we used the glm( ) function from the package stats (included with a base install of R) as shown below:

lr1←glm(TCC.YN~CDC*IGF*HOXA*IL8R*MDK, family=binomial("logit"), data=uRNA.Trial))

here lr1 is the classifier created and the other parameters are as described for the linear discriminant. Once again, full interaction is specified using the (*) operator.

Classification is performed in a manner very similar to that for LDA-3:

score←predict(lr1, new.data, type='response')

where score is the value used to classify urine samples based on the measurement of the five genes in new.data, as above. The cut off for lr1 is set to 0.102 to achieve a specificity of 85%; values about the cut off are considered to be positive to TCCs.

The coefficients for the classifier are:
−103.0818143+
3.9043769*CDC.d.R100+
13.1120675*IGF.d.R100+
17.4771819*HOXA.d.R100+
−10.7711519*IL8R.d.R100+
21.1027595*MDK.d.R100+
−0.5938881*CDC.d.R100*IGF.d.R100+
−1.0736184*CDC.d.R100*HOXA.d.R100+
−1.3340189*IGF.d.R100*HOXA.d.R100+
0.3126461*CDC.d.R100*IL8R.d.R100+
1.4597355*IGF.d.R100*IL8R.d.R100+
1.8739459*HOXA.d.R100*IL8R.d.R100+
−1.035054*CDC.d.R100*MDK.d.R100+
−2.5885156*IGF.d.R100*MDK.d.R100+
−2.7013483*HOXA.d.R100*MDK.d.R100+
1.4546134*IL8R.d.R100*MDK.d.R100+
0.0767503*CDC.d.R100*IGF.d.R100*HOXA.d.R100+
−0.0663361*CDC.d.R100*IGF.d.R100*IL8R.d.R100+
−0.1015552*CDC.d.R100*HOXA.d.R100*IL8R.d.R100+
−0.2110656*IGF.d.R100*HOXA.d.R100*IL8R.d.R100+
0.1361215*CDC.d.R100*IGF.d.R100*MDK.d.R100+
0.1601118*CDC.d.R100*HOXA.d.R100*MDK.d.R100+
0.259745*IGF.d.R100*HOXA.d.R100*MDK.d.R100+
−0.0106468*CDC.d.R100*IL8R.d.R100*MDK.d.R100+
−0.1947899*IGF.d.R100*IL8R.d.R100*MDK.d.R100+
−0.185286*HOXA.d.R100*IL8R.d.R100*MDK.d.R100+
0.0136603*CDC.d.R100*IGF.d.R100*HOXA.d.R100*IL8R.d.R100+
−0.0151368*CDC.d.R100*IGF.d.R100*HOXA.d.R100*MDK.d.R100+
0.0056651*CDC.d.R100*IGF.d.R100*IL8R.d.R100*MDK.d.R100+
0.0030538*CDC.d.R100*HOXA.d.R100*IL8R.d.R100*MDK.d.R100+
0.0232556*IGF.d.R100*HOXA.d.R100*IL8R.d.R100*MDK.d.R100+
−0.000867*CDC.d.R100*IGF.d.R100*HOXA.d.R100*IL8R.d.R100*MDK.d.R100

Results qRT-PCR Analysis of Urine Samples:

To obtain an overview of the effect of IL8Rb on TCC detection, two dimensional scatter plots were constructed using qRT-PCR data obtained from the urine of patients with either TCC (n=56) or the non-malignant conditions urolithiasis (n=25), urinary tract infection (n=18) or cystitis (n=18). The scatter plots were constructed using pairs of genes from a four gene signature (MDK, CDC2, HOXA13, IGFBP5). IL8Rb was then substituted for one gene of each pair and the data re-plotted. These plots are shown in FIG. 2a-f. Substitution of IL8Rb for IGFBP5 and HOXA13 in plots with MDK (FIGS. 2a-c) showed improved separation between samples from patients with TCC and those with non-malignant conditions. The same trend was observed in plots with CDC2 in which IL8Rb was substituted for IGFBP5 and HOXA13 (FIGS. 2d-f).

Figure 3A:
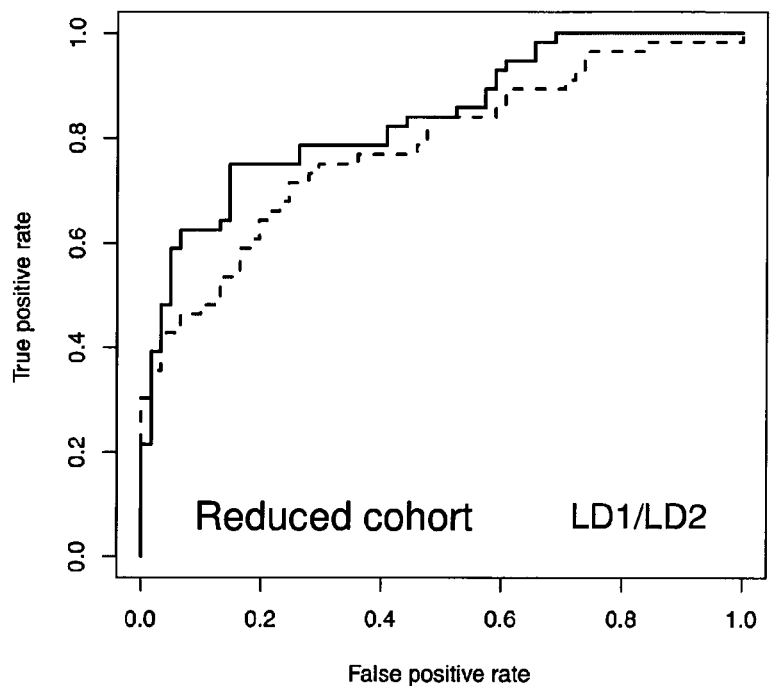
FIGS. 3a-3b ROC curve analysis (sensitivity vs specificity) showing the effect of including IL8Rb in the diagnostic algorithms derived using linear discriminate analysis (LD) and linear regression (LR). The ROC curves are derived from patients with TCC (n=56) and the non-malignant diseases cystitis, urinary tract infection and urolithiasis (n=61).
Figure 3B:
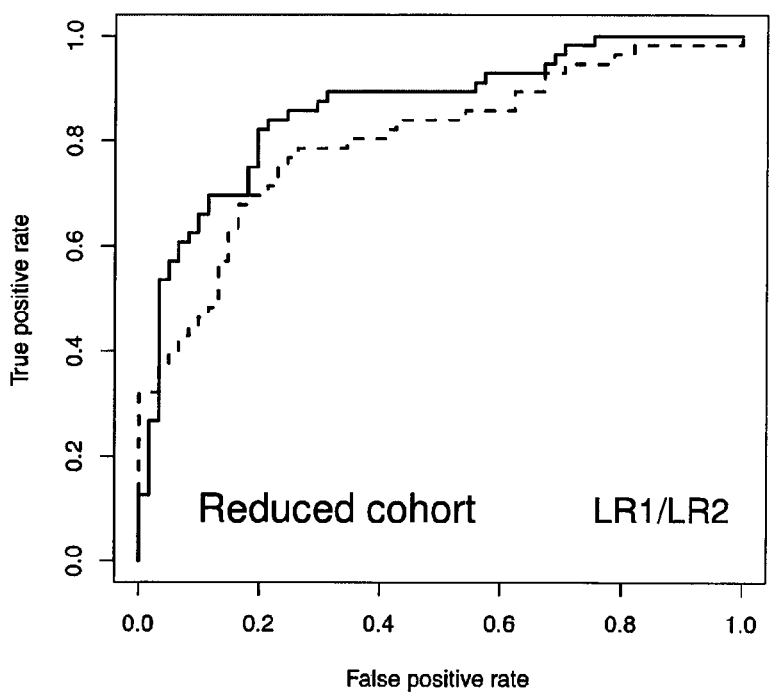

The contribution of IL8Rb to the correct diagnosis of TCC in patients presenting with gross hematuria was then quantified by ROC curve analysis. qRT-PCR data for each gene in the signature (MDK, CDC2, IGFBP5 and HOXA13) and IL8Rb was used to develop linear discriminate algorithms that maximised the discrimination between the patients with TCC and those without. Two linear discriminate algorithms were developed using the entire cohort of 442 samples: LD1, which used the qRT-PCR data from MDK, CDC2, HOXA13 and IGFBP5 and LD2, which used MDK, CDC2, HOXA13, IGFBP5 and IL8Rb. LD1 and LD2 were then used to generate ROC curves showing the sensitivity and specificity of TCC detection in the group of patients with confirmed TCC (n=56) or the non-malignant conditions urolithiasis (n=25), urinary tract infection (n=18) or cystitis (n=18). FIG. 3a shows the ROC curves for LD1 and LD2. The area under the ROC curve for LD1 was 78% compared to 84% for LD2.

As an alternative to linear discriminate analysis, logistic regression was used as an independent method to develop an algorithm for the discrimination between patients with TCC and those with non-malignant disease. As for the linear discriminate analysis, the logistic regression algorithms were developed using the entire cohort of 442 samples. The ROC curves obtained using logistic regression and the 56 TCC and 61 non-malignant samples described above are shown in FIG. 3b. The area under the ROC curve for LR1 (obtained using qRT-PCR data from MDK, CDC2, HoxA13 and IGFBP5) was 80% compared to 86% for LR2 (obtained using qRT-PCR data from MDK, CDC2, HOXA13, IGFBP5 and IL8Rb). This data clearly illustrates that inclusion of IL8Rb in methods for the detection of TCC using urine samples can lead to improved discrimination between patients with TCC and non-malignant diseases such as cystitis, urinary tract infection and urolithiasis.

Figure 4A:
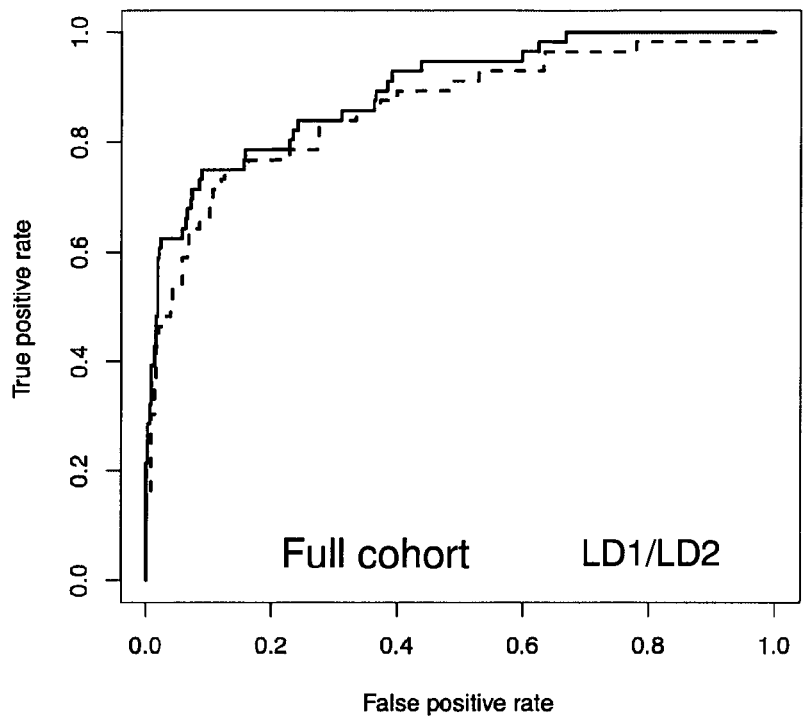
FIGS. 4a-4b Extended ROC curve analysis showing the effect of including IL8Rb in the diagnostic algorithms derived using linear discriminate analysis (LD) and linear regression (LR). The ROC curves are derived from patients with TCC (n=56) and, unlike FIGS. 3a-3b, any non-malignant disease in the cohort (n=386).
Figure 4B:
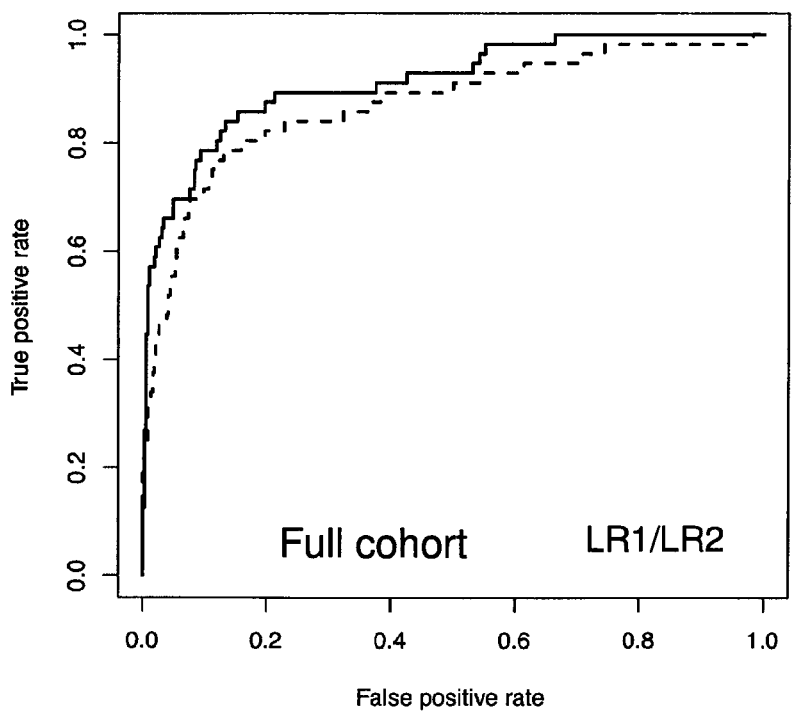

To confirm the improved accuracy afforded by IL8Rb for the discrimination between patients with TCC and urolithiasis, urinary tract infection or cystitis was maintained in an unselected cohort of patients comprising a larger number and diversity of non-malignant patients, the ROC curve analyses were repeated with the entire cohort of 442 samples described in Table 1. In this analysis, the area under the curve for LD1 and LD2 was 86 and 89%, respectively (FIG. 4a). Similarly, the area under the curve for LR1 was 87% and for LR2 91% (FIG. 4b). This result confirms that IL8Rb leads to improved accuracy in the detection of TCC using urine samples.

This improvement in cancer detection due to the inclusion of IL8Rb was further illustrated by applying LD1/LD2 and LR1/LR2 to the 442 patient cohort and then determining the sensitivity of detection of stage Ta TCC alone. Stage Ta tumours are smaller, more differentiated tumours that are typically more difficult to detect than higher stage tumours. LD1 detected 18/31 (58%) of the Ta tumours compared to 19/31 (61%) for LD2 at a specificity of 85%. LR1 detected 21/31 (68%) compared to 24/31 (77%) for LR2 (specificity of 85%). This data shows that the inclusion of IL8Rb into the LD and LR algorithms increased the sensitivity of detection of stage Ta tumours by up to 9%. In comparison to these RNA tests, the three other bladder cancer tests in this study showed markedly lower accuracy for the detection of Ta tumours: urine cytology (39% sensitivity, 94% specificity), NMP22 ELISA (35% sensitivity, 88% specificity) and NMP22 (BladderChek® "a registered trademark of Matritech, Inc. of Massachusetts, United States") (39% sensitivity, 96% specificity).

IL8Rb as an Aid in the Diagnosis of Inflammation of the Urinary Tract

To determine the ability of IL8Rb to be used in the diagnosis of patients with inflammation of the urinary tract due to causes such as cystitis or urinary tract infections, the urine levels of IL8Rb mRNA in haematuria patients diagnosed with benign prostate hyperplasia, non-specific prostate disease, vascular prostate, hematuria secondary to warfarin use, and cystitis/urinary tract infection were determined by qRT-PCR. The mean IL8Rb ΔCt levels for each of these conditions were −3.12, −3.10, −2.84, −1.98 and −5.27, respectively. The difference between the mean of the IL8Rb level in patients with cystitis/urinary tract infection and the other non-malignant states combined was determined to be significant (p=0.001) using the Wilcoxon rank sum test. Box plots portraying this data are shown in FIG. 5. This data shows an elevation of IL8Rb levels in the majority of patients diagnosed with either cystitis or urinary tract infection compared to the other non-malignant conditions examined Overlap between plots is likely to be explained by a combination of three factors: (i) the inability of standard clinical practice to correctly diagnose each condition, (ii) co-morbidity (eg infection and benign prostate hyperplasia), and (iii) the normal association of high urine neutrophil counts in a subset of patients with benign prostate hyperplasia, non-specific prostate disease, vascular prostate or hematuria secondary to warfarin use. Regardless, given the strict association between inflammation and neutrophil numbers, the quantification of IL8Rb in urine provides an accurate method of detecting inflammation of the urinary tract, be it as a consequence of infection or in association with other non-malignant conditions.

Example 2

Methods

Study Population

A consecutive series of patients without a prior history of TCC were recruited prospectively from nine urology clinics in New Zealand and two in Australia between 28 Apr. 2008 and 11 Aug. 2009. The patient set included the patients used in example 1, but included an additional 46 patients, whose data was not available for the first analysis. The further studying also includes further analysis of the results obtained.

The samples were collected and RNA collected and tested as described in Example 1.

RNA Test Development uRNA® consists of four mRNA markers, CDC2, HOXA13, MDK and IGFBP5. These markers were selected on the basis of their low expression in blood and inflammatory cells and over-expression in TCC.[2] In this cohort study, we prospectively specified a linear discriminate algorithm (uRNA-D) that combined the four markers into a single score. uRNA-D was independent, being developed on an earlier dataset. It was not however, derived using a strictly characterised patient group representing the intended target population for the test. As a consequence, the study protocol also defined the development of a new algorithm (Classifier-D) for the use of the five markers CDC2, HOXA13, MDK, IGFBP5 and IL8Rb using data obtained from the patients recruited to the current cohort study.

In addition to Classifier-D, a second algorithm (Classifier-S) was derived using the cohort study data to enable identification of tumours that were either of advancing stage (≥stage 1) or high grade (WHO/ISUP 1998 classification). Algorithm-S comprised all five markers, including CDC2 and HOXA13 which had previously been shown to be differentially expressed between Stage Ta tumours and those ≥stage 1.

Classifier Development

Development of two classifiers for the use of the five markers CDC2, HOXA13, MDK, IGFBP5 and IL8Rb (Classifier-D and Classifier-S) were based on data obtained in this study, in accordance with the methods outlined in this specification. Briefly, logistic regression models were made using the statistical programming environment, R (R Development Core Team (2011). R: A language and environment for statistical computing. R Foundation for Statistical Computing, Vienna, Austria. ISBN 3-900051-07-0, URL http://www.R-project.org/). Models made using $\Delta C_P$ values for each of the five markers and their two way interactions (eg. MDK×CDC2, MDK×IGFBP5, etc) were evaluated for their ability to classify; those with the lowest AIC values were evaluated in a leave-one-out cross validation procedure for their sensitivity when the specificity was set to 85%. Several models demonstrated comparable performance for each of Classifier-D and Classifier-S, with the model with the fewest numbers of parameters being selected.

Statistical Methods

Where a diagnostic test was specified in the protocol, proportions and 95% confidence intervals were calculated for sensitivity and specificity. Received operating characteristic (ROC) curves were plotted and compared using the Stata roctab and roccomp commands (Statacorp and Delong). For Classifier-D confidence intervals are not appropriate, but Fishers exact or Chi squared tests (where sample sizes allow) were used to test for an association between TCC or patient characteristics and chances of true positive or false positive results. Logistic regression models were used to explore factors associated with false positive and false negative results. All analyses were carried out in Stata version 11.2.

Results

Figure 8:
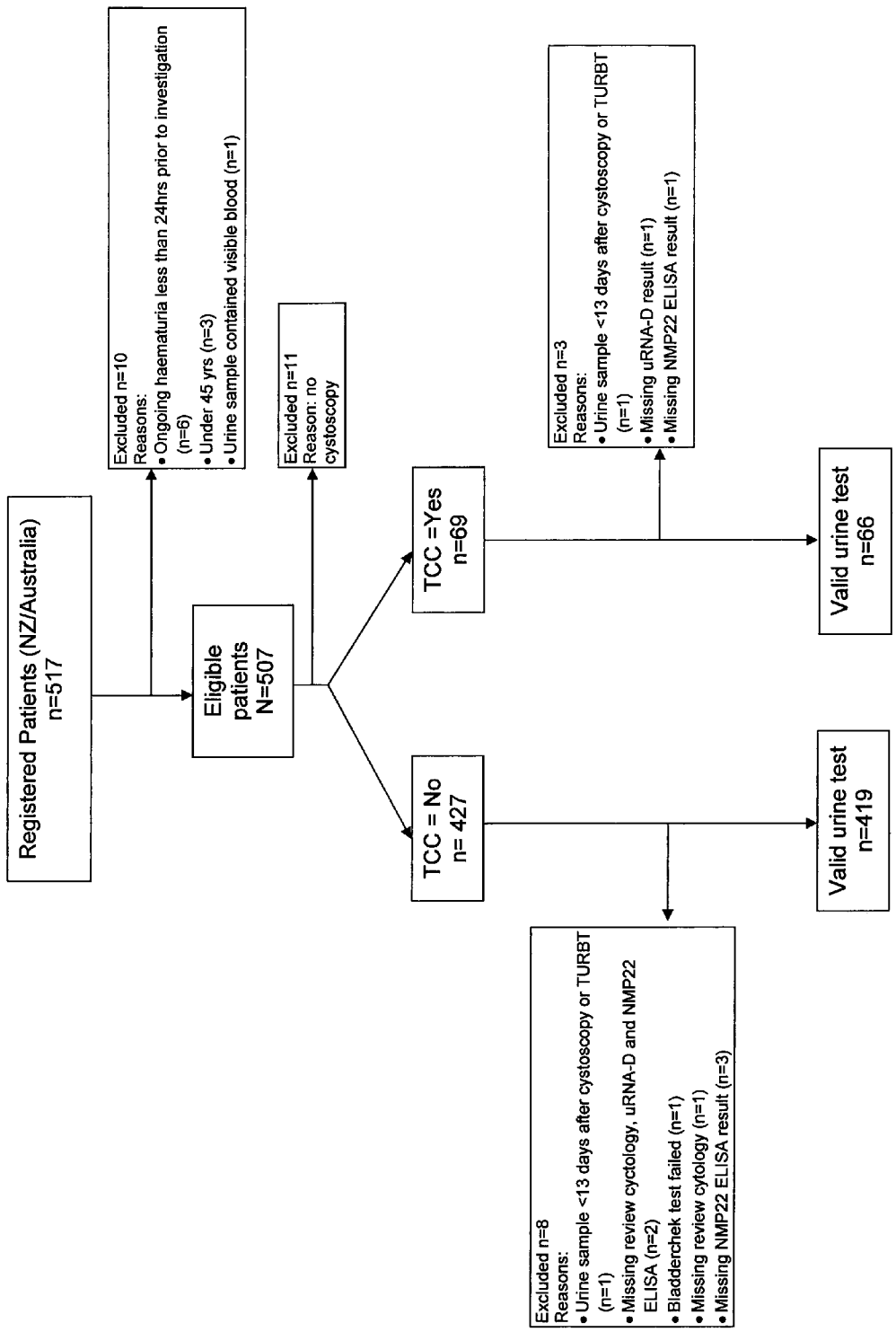
FIG. 8 shows a flow chart for the patient recruitment procedures and numbers for Example 2.
Figure 14A:
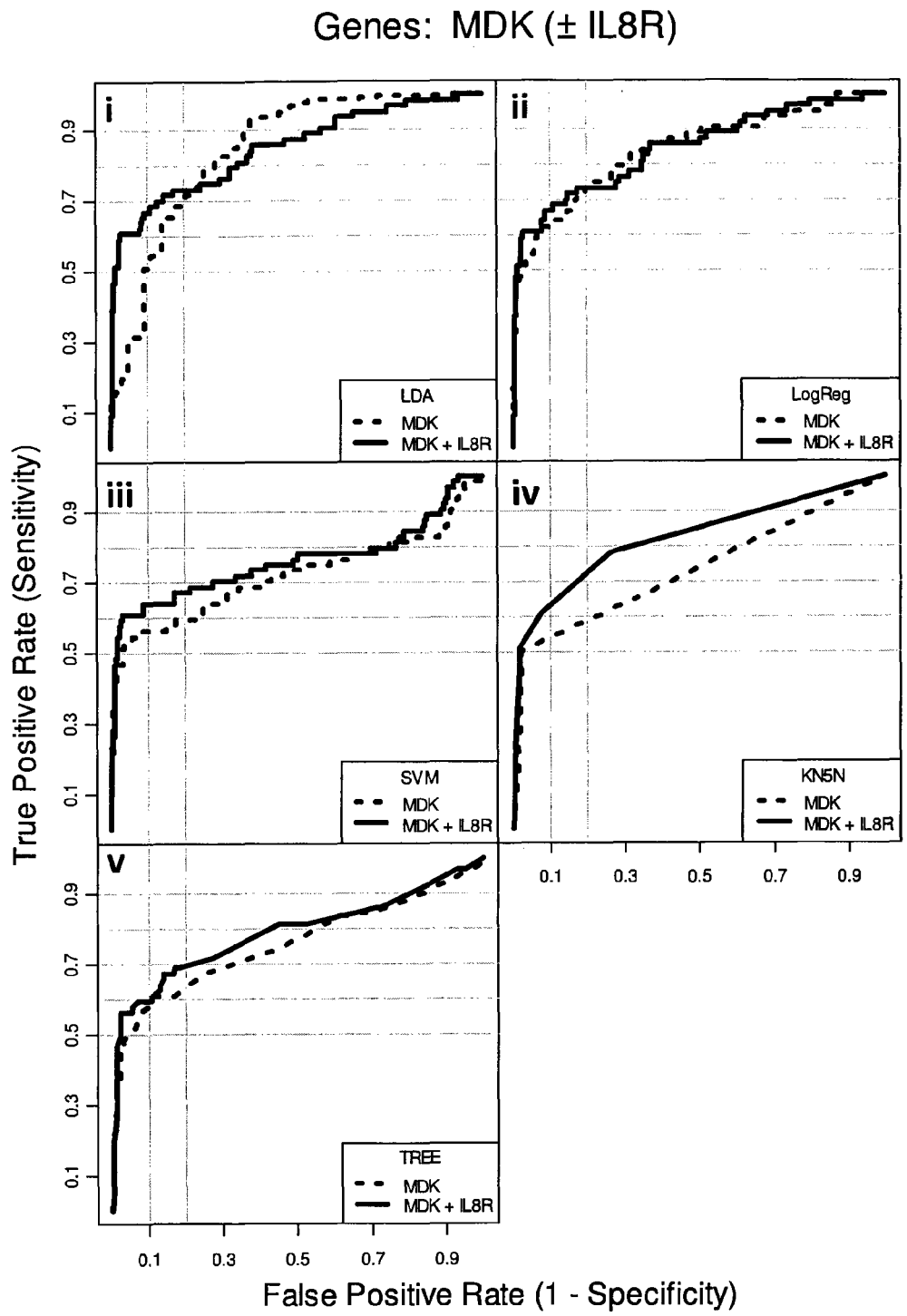
FIGS. 14a-14o show ROC curves for the combinations of markers.
Figure 14B:
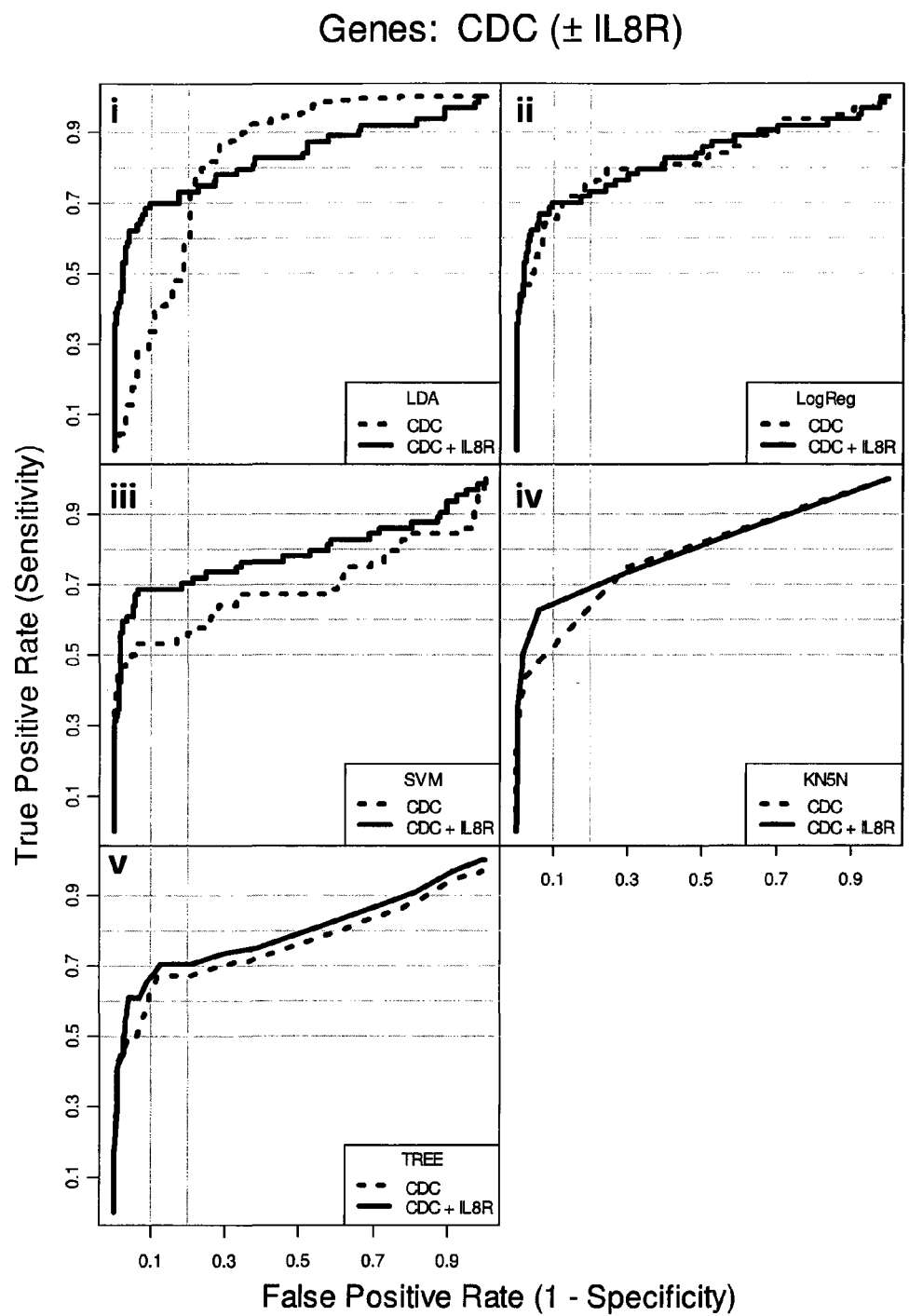
Figure 14C:
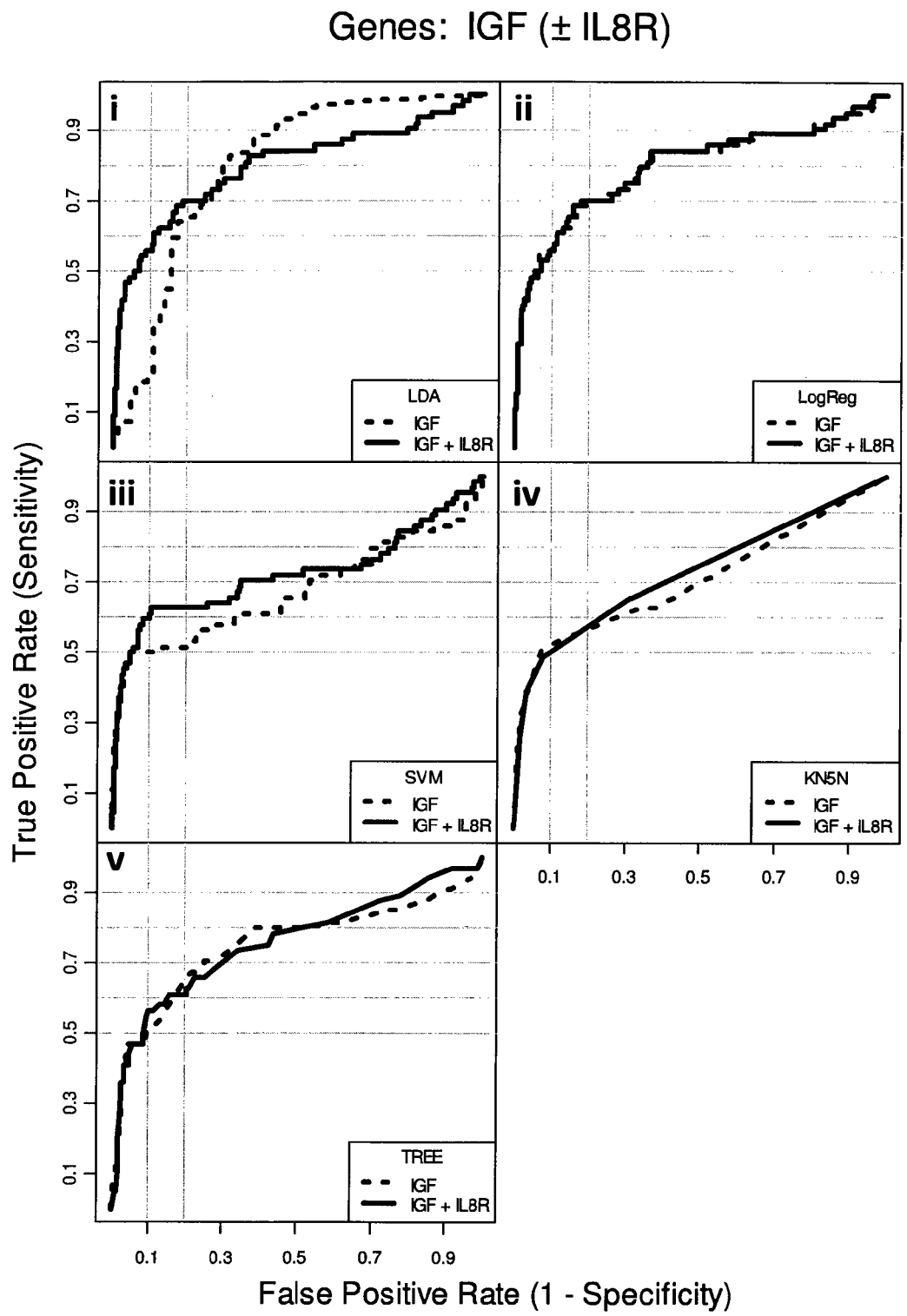
Figure 14D:
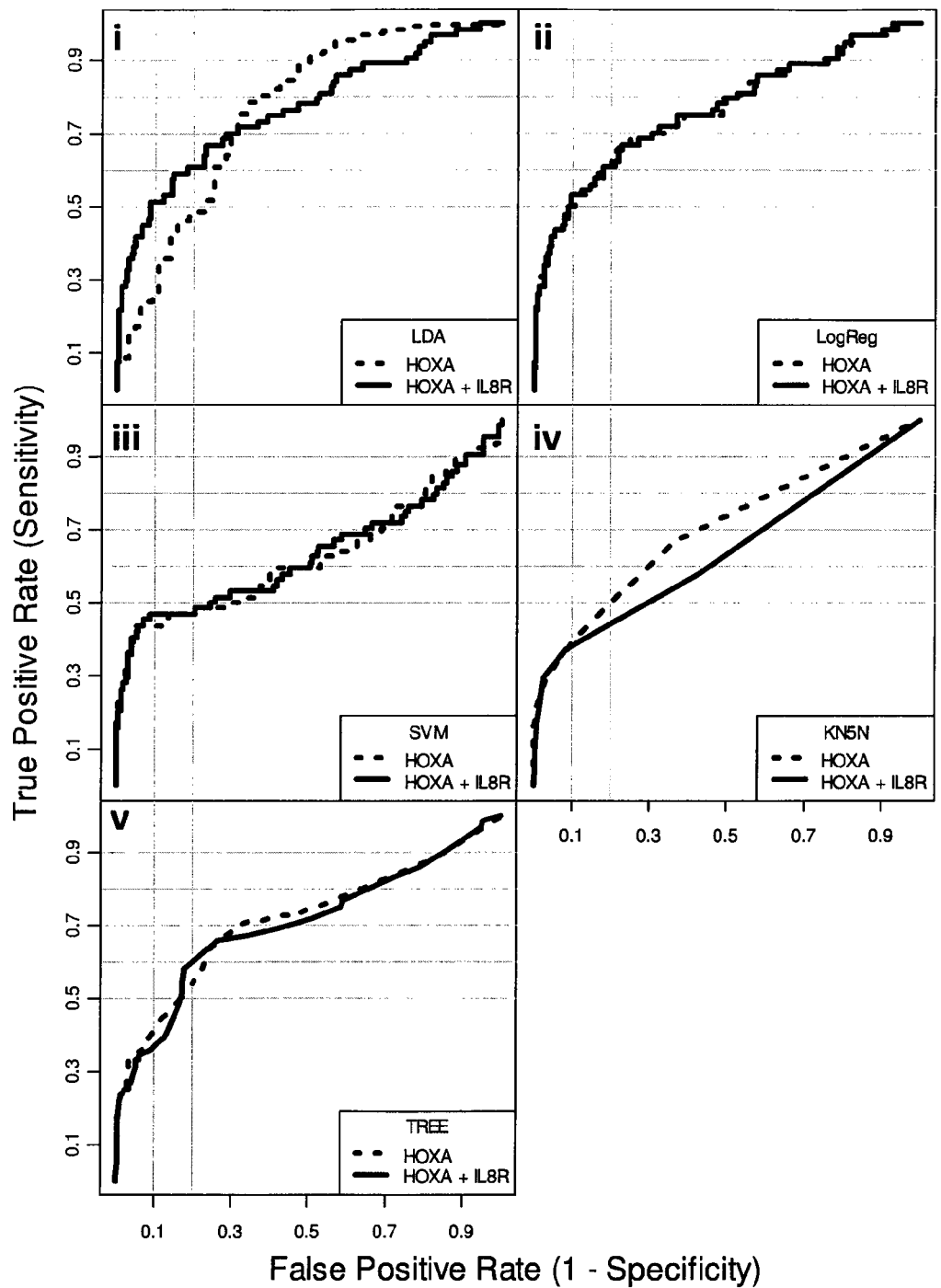
Figure 14E:
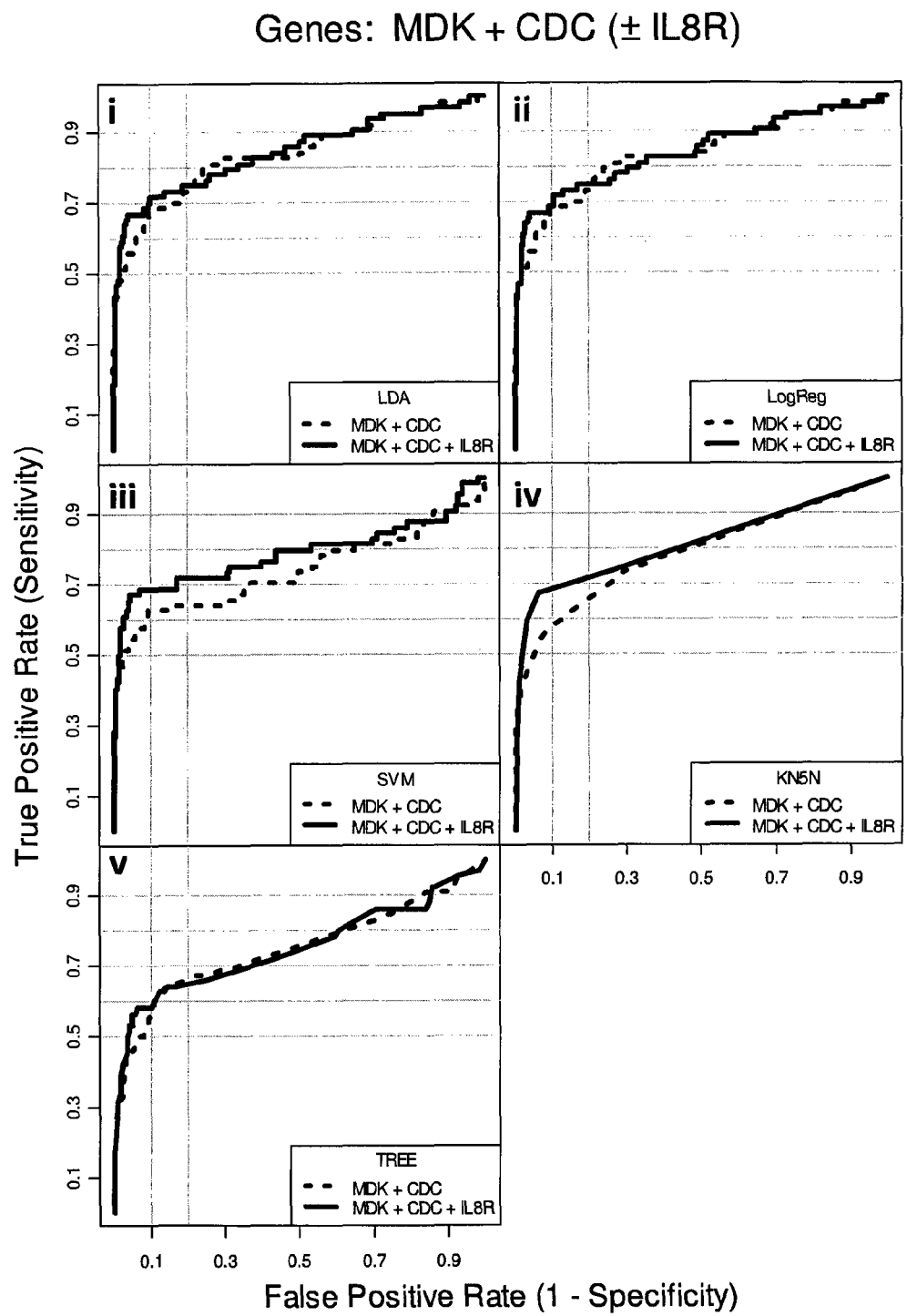
Figure 14F:
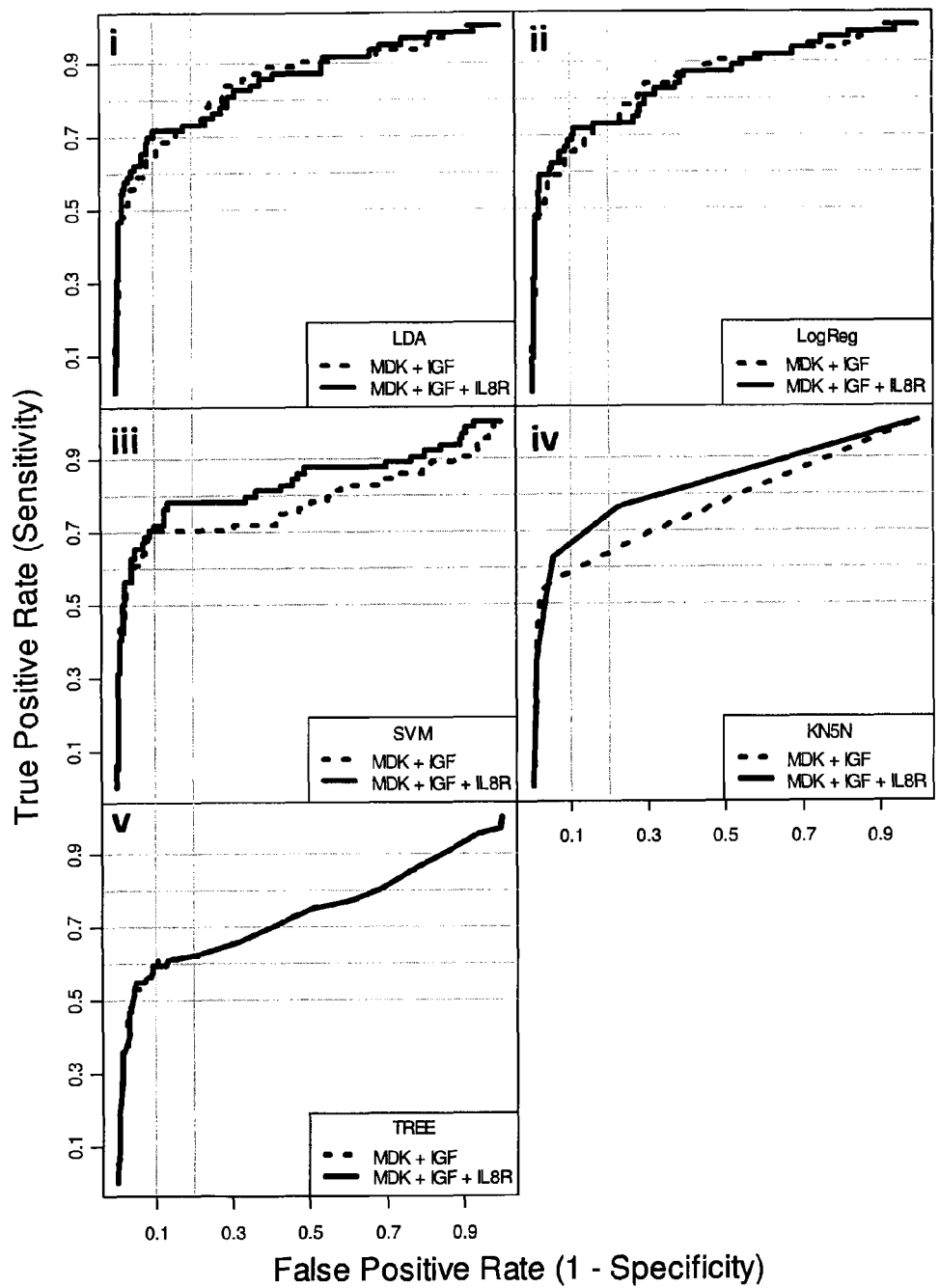
Figure 14G:
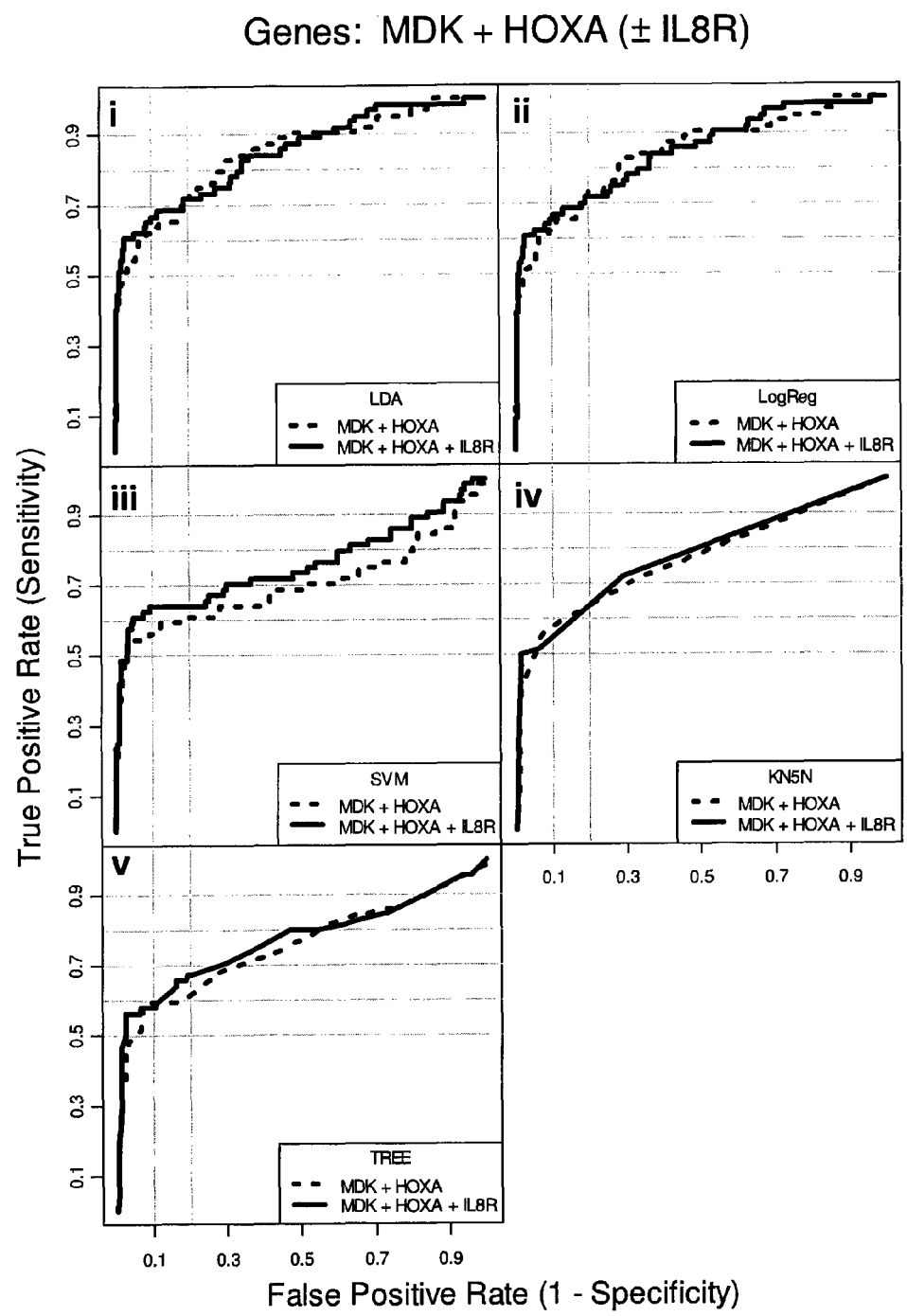
Figure 14H:
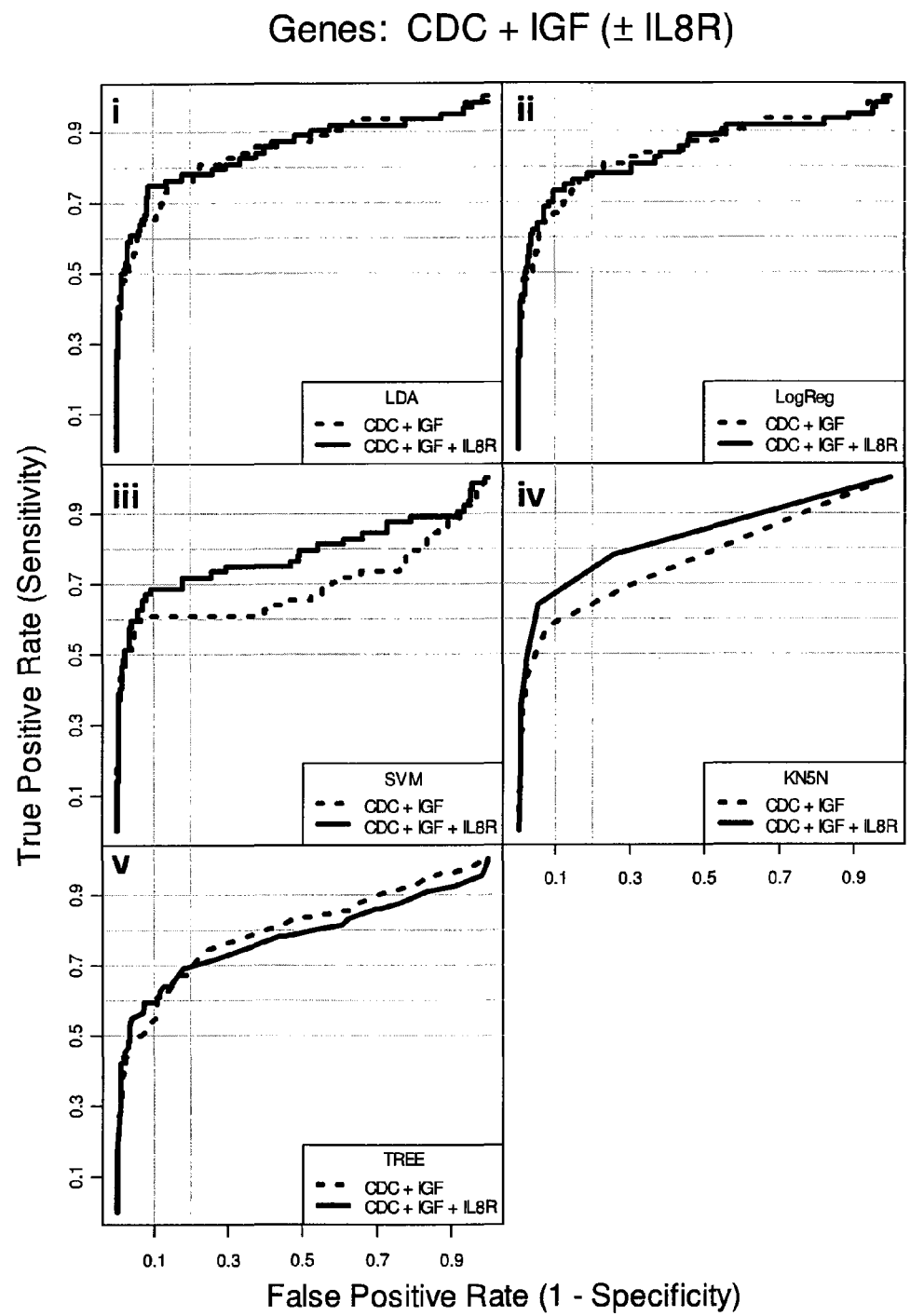
Figure 14I:
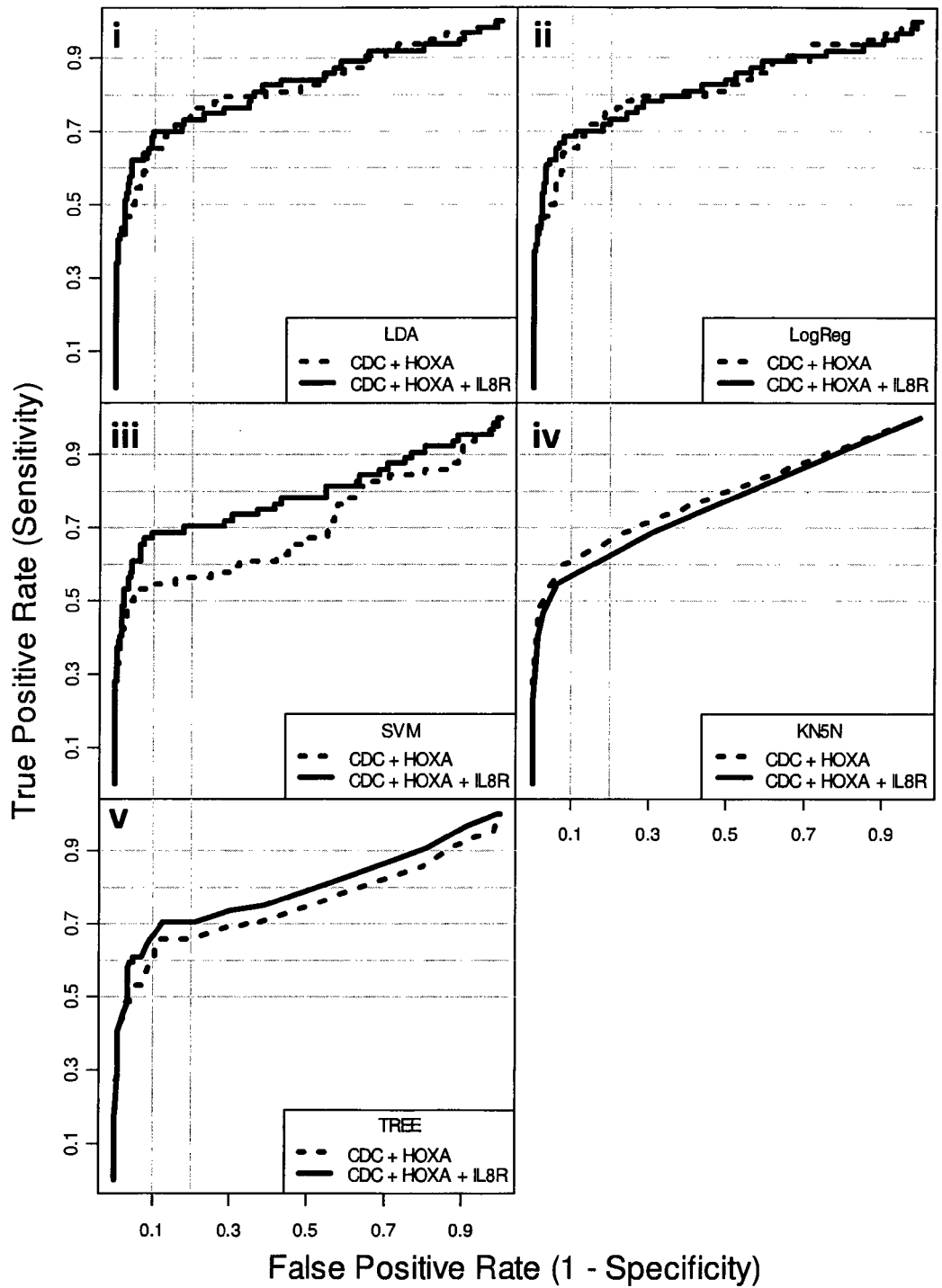
Figure 14J:
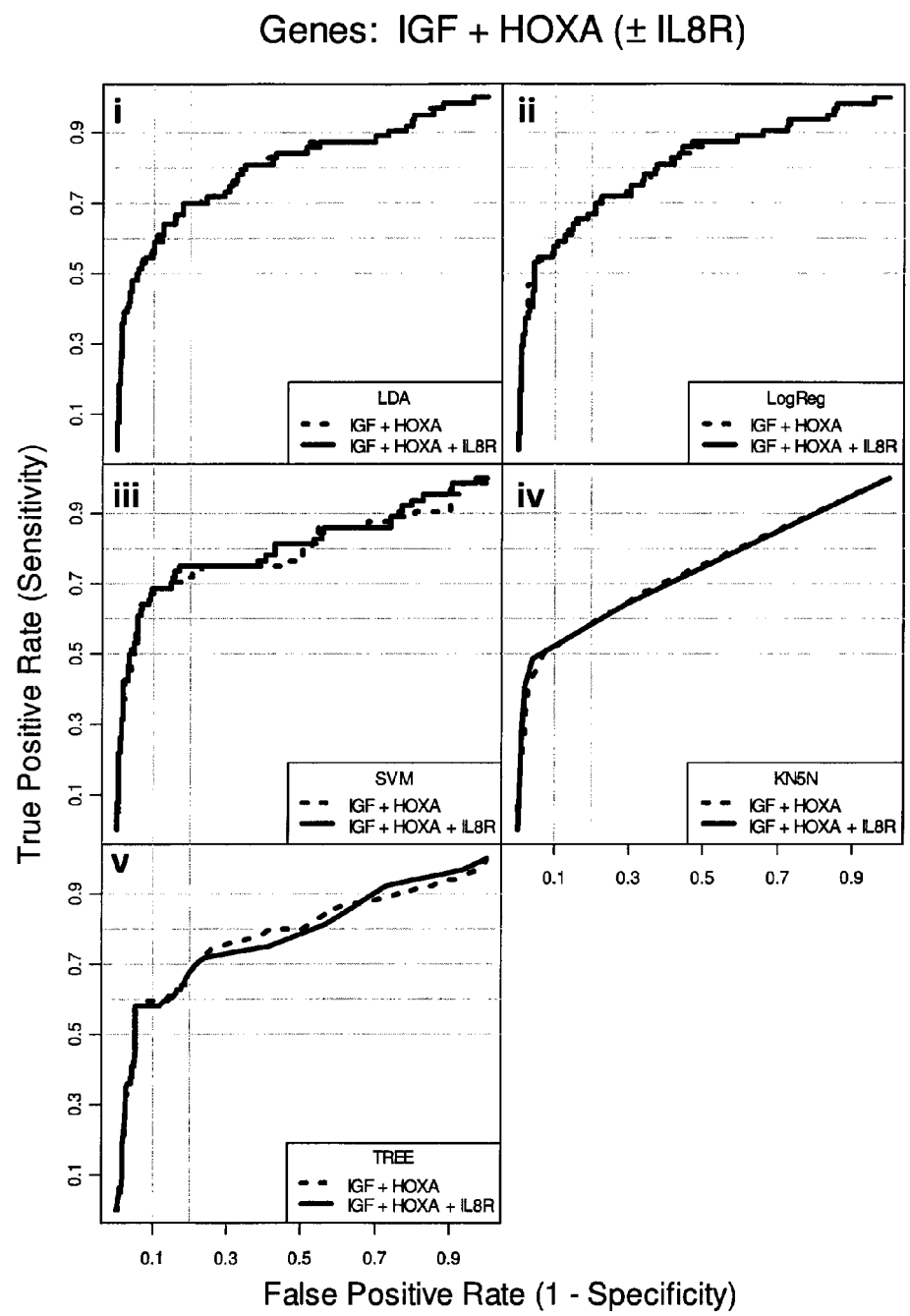
Figure 14K:
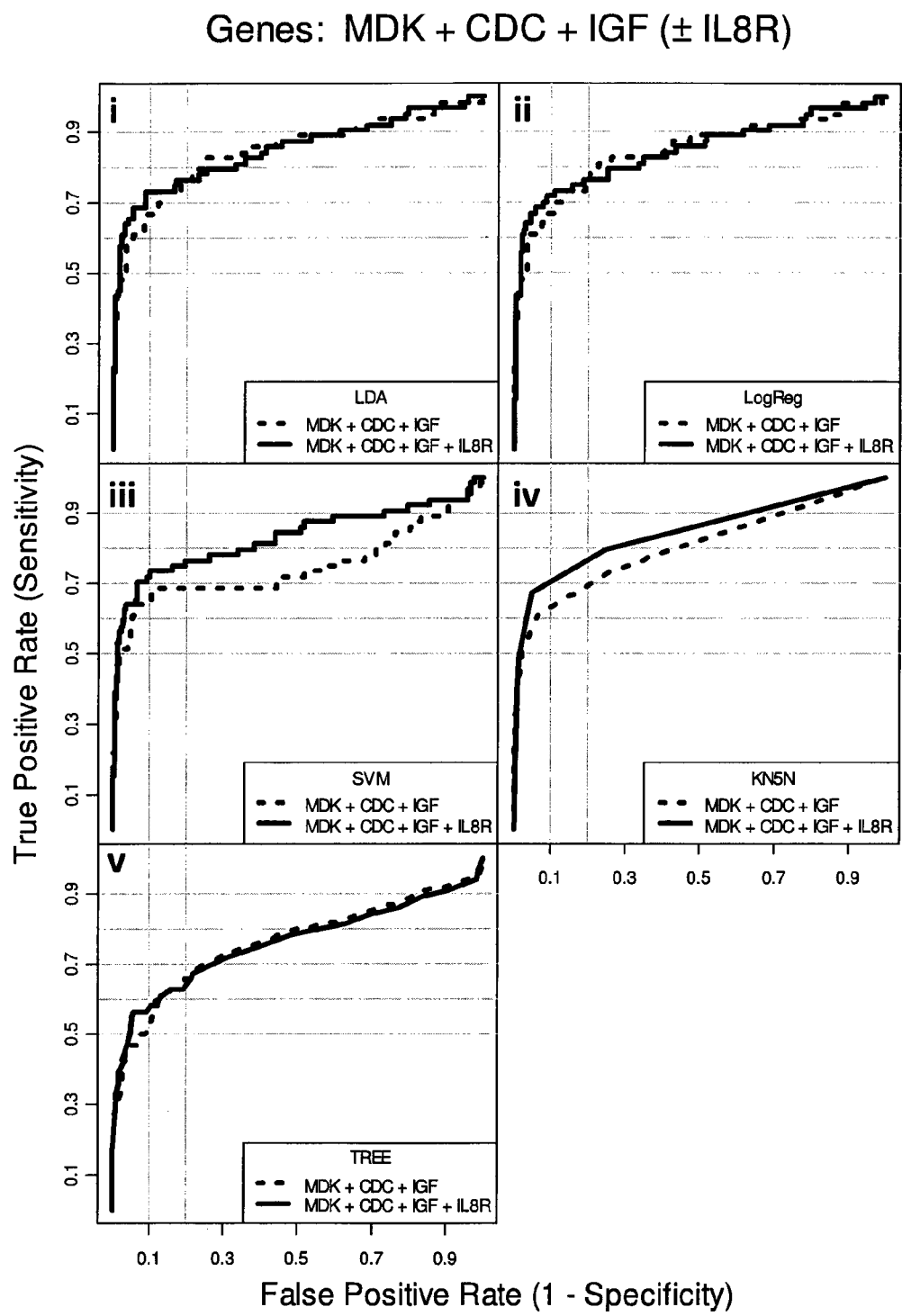
Figure 14I:
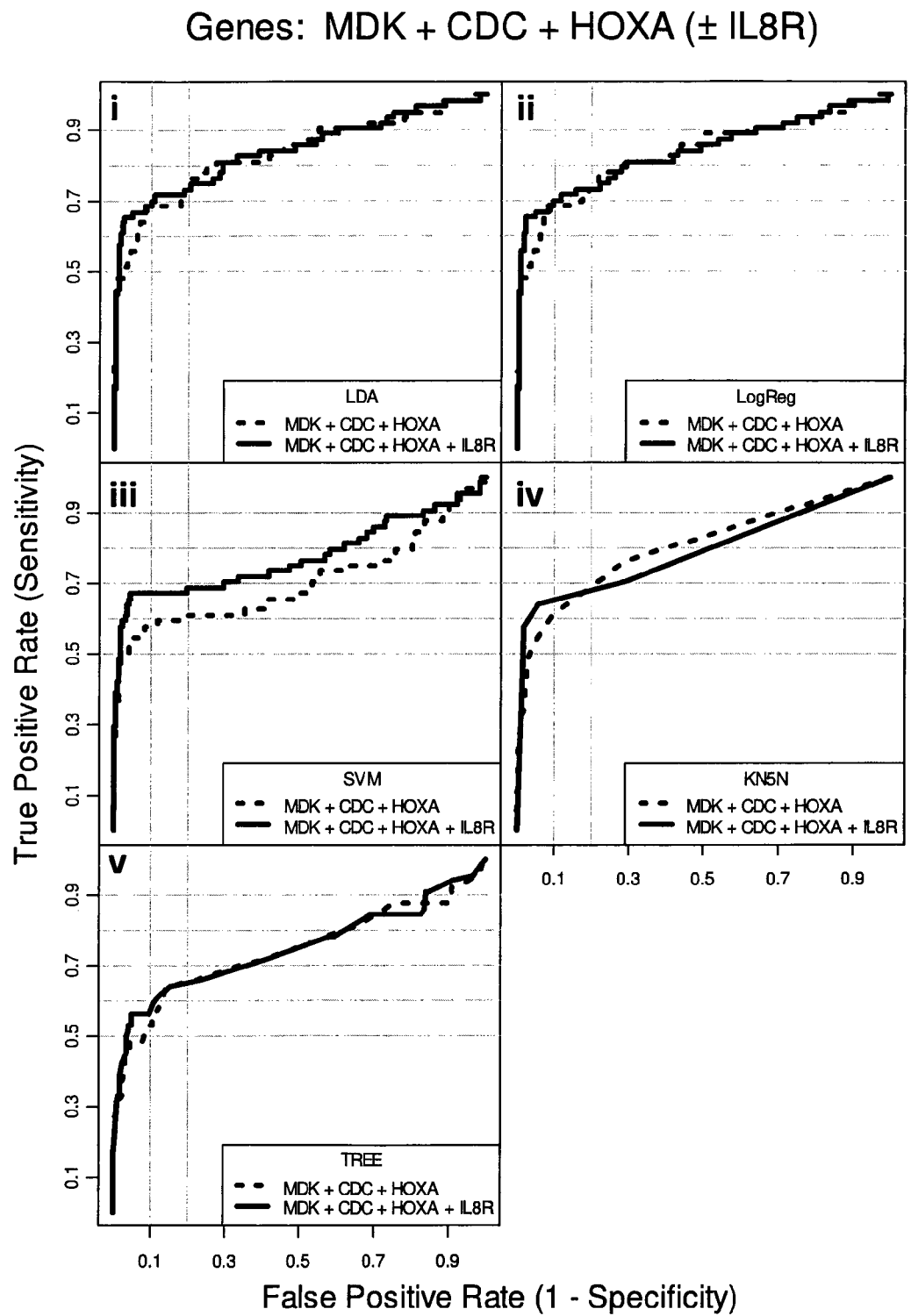
Figure 14M:
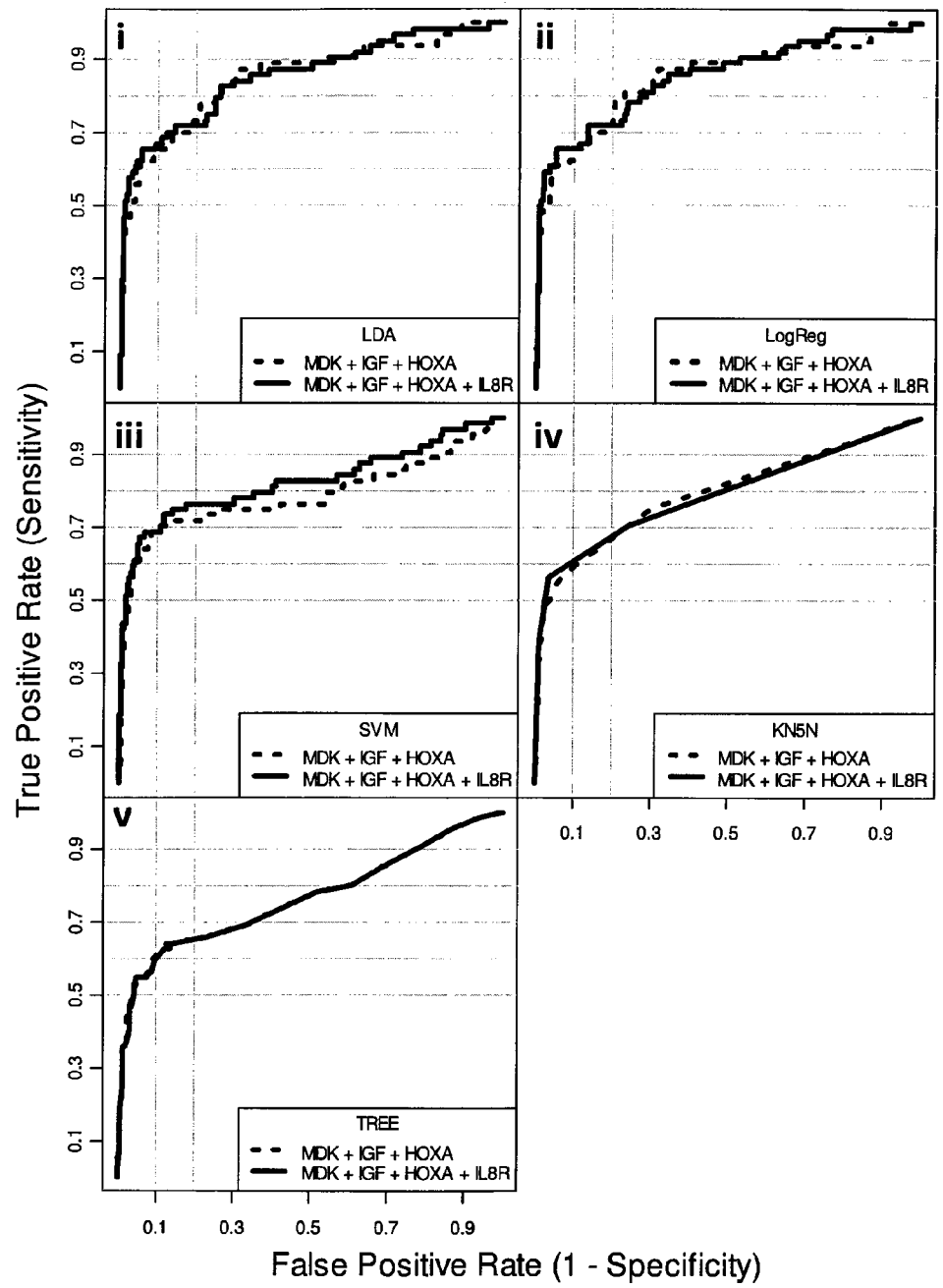
Figure 14N:
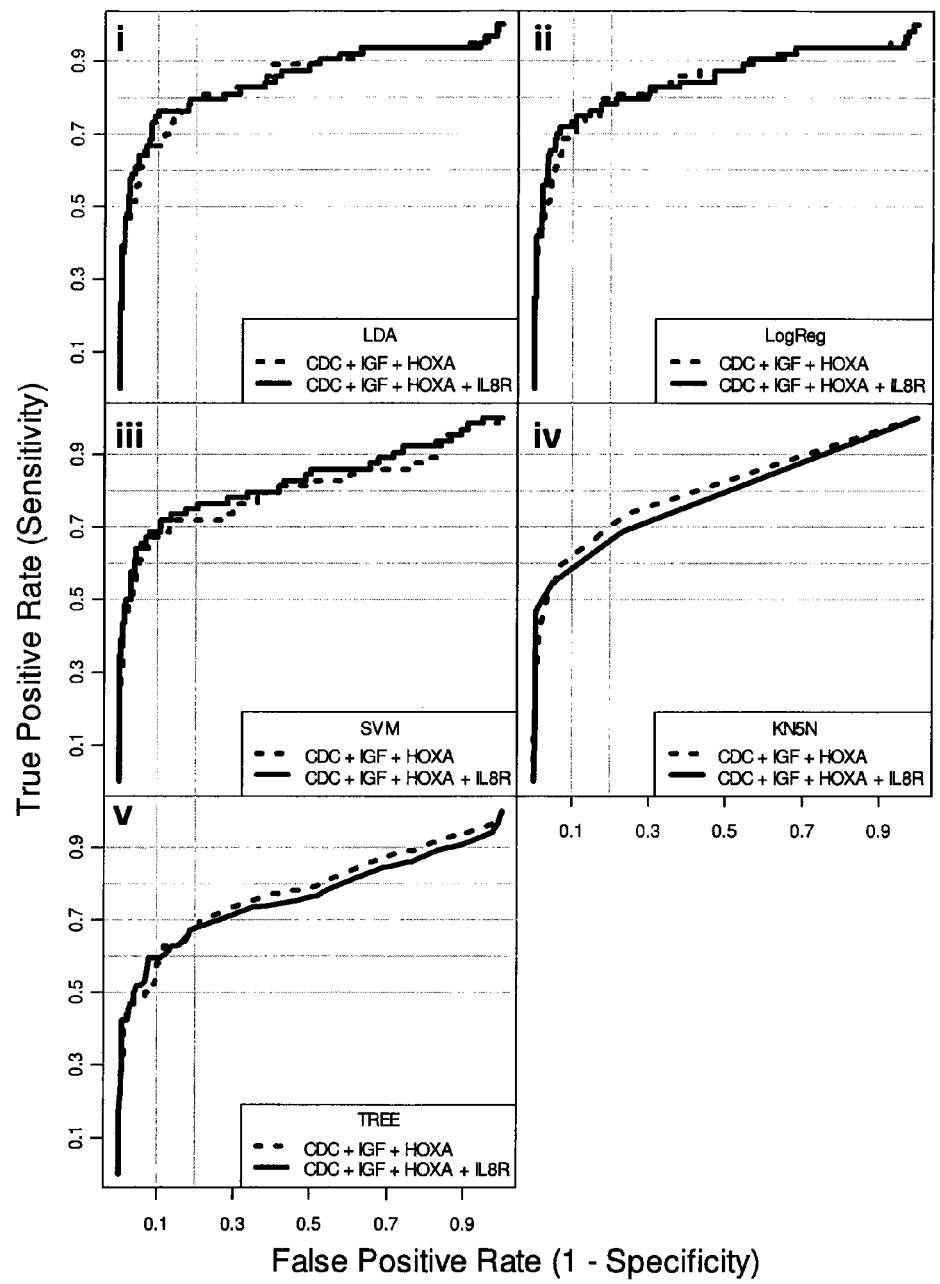
Figure 14O:
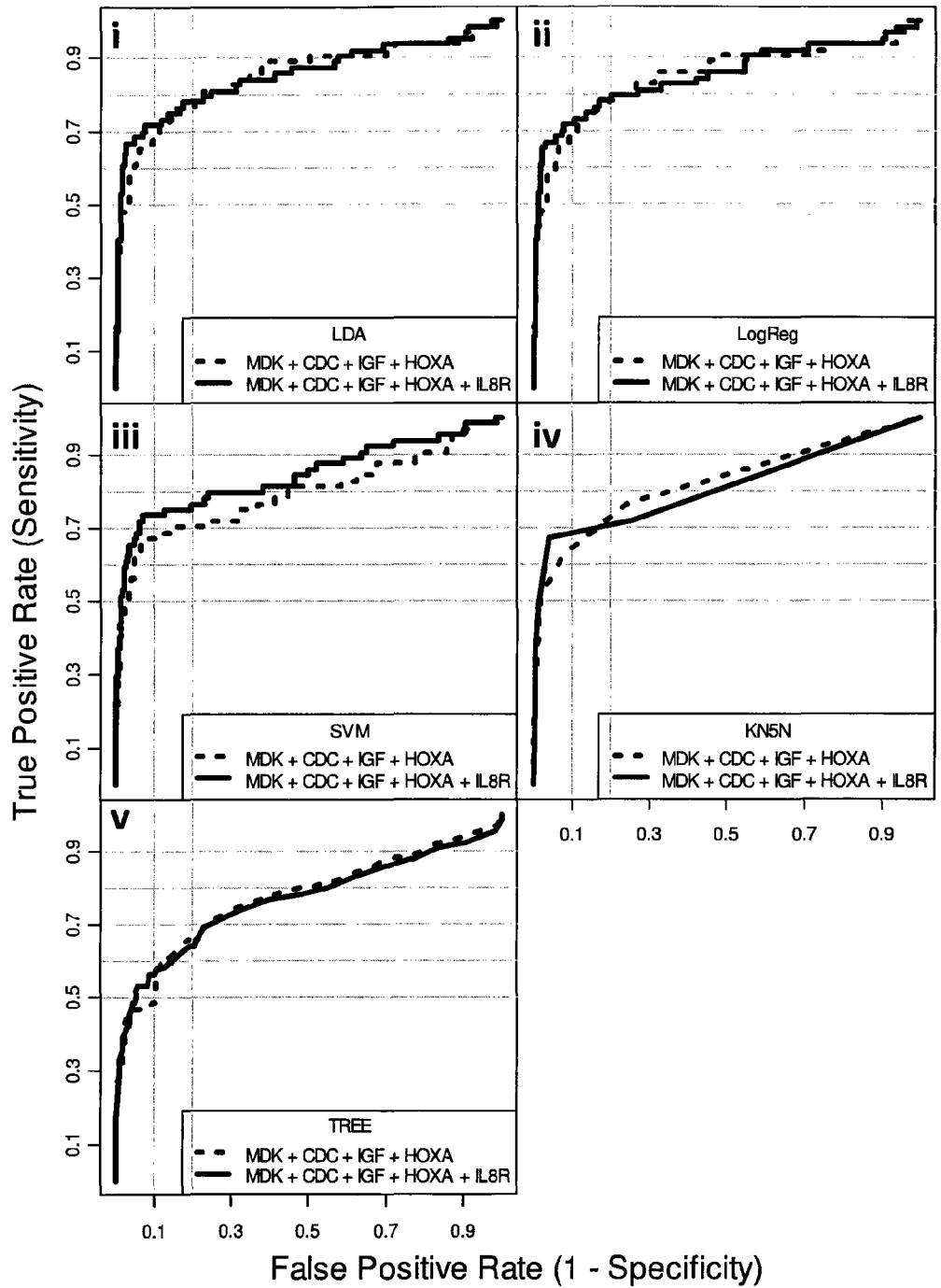

A total of 517 patients were initially recruited to the study; 4% of patients were excluded because they were found to be ineligible (n=10), did not undergo cystoscopy (n=9), TCC status was not stated (n=2) or they did not provide an acceptable urine sample (n=2) (FIG. 8). A further 10 patients were excluded from the analysis because they did not have results for one or more of the urine tests. The baseline demographic and clinical characteristics of the 485 remaining patients are shown in FIG. 9.

The prevalence of TCC in the cohort was 13.6%. Two were missing a review stage (both were Ta by local review) and two were not given a review grade (one was grade 1 by the local pathologist, the other low). Of the 66 tumours, 55 were superficial (stage Ta, T1 or Tis) and 11 were muscle invasive (T2). No patients had detectable metastases or involvement of regional lymph nodes. Using the 1973 grading system, 24 were classified as grade 3, 38 grade 2, three grade 1 and one unknown. With the WHO98 system, 29 were classified as high grade, four mixed, 32 low grade and one unknown. In addition to the TCCs, two patients were diagnosed with a papilloma, and seven with other neoplasms (five of these urological).

The cutoff for the uRNA-D test was determined on the study cohort, with specificity set at 85%. With this cutoff, uRNA-D detected 41 of the 66 TCC cases (sensitivity of 62%), compared with NMP22™ ELISA (50%), Bladderchek™ (38%) and cytology (56%). The RNA test developed on the cohort data Classifier-D detected 54 of the TCC cases (82%) at a specificity of 85% and 48 (73%) at a specificity of 90%. uRNA-D and NMP22™ ELISA values can be directly compared as both tests were fully specified prior to the study. FIG. 2a shows the ROC curves; the area under the curves (AUCs) are 0.81 and 0.73 respectively (p=0.03). The ROC curve for Classifier-D was 0.87 (FIG. 11b), and the improvement in performance relative to uRNA-D appears to be mostly in the range of clinically relevant specificities (above 80%).

Overall, Classifier-D detected 97% of the high/grade 3 tumours, compared to uRNA-D (83%), cytology (83%), NMP22 ELISA (69%) and Bladderchek (38%). Classifier-D was also more sensitive for the detection of low grade tumours (69%), with the other tests ranging from 28-41% (FIG. 12). Classifier-D was positive for all the TCC cases of Stage ≥1 plus both Tis, but the sensitivity was 68% for stage Ta (p=0.016, FIG. 12). This was still substantially higher than the other tests, with uRNA-D being the next highest at 41%. TCC patients with microhaematuria evident in their urine sample were more likely to have their TCC detected by including IL8Rb than those without microhaematuria (p<0.0005), though this is likely to be at least partially a result of the higher proportion of high stage and grade TCCs among those with microhaematuria. Numbers were insufficient to explore this further in regression analyses.

Of the 12 cases missed by Classifier-D, all were stage Ta and all except one were low grade (WHO ISUP 1998). Only two of the twelve (both low grade, stage Ta TCC) were picked up by another test (one by both NMP22™ ELISA and BladderChek™ and one by uRNA-D). Of the 12 cases missed by Classifier-D, all were stage Ta and all except one were low grade (WHO ISUP 1998). Only two of the twelve (both low grade, stage Ta TCC) were picked up by another test (one by both NMP22™ ELISA and BladderChek™ and one by uRNA-D). Cytology did not pick up any TCCs that Classifier-D missed.

Patient A: High Grade renal pelvic T2 tumour, no concurrent Tis, no size given.

Patient B: High grade Bladder T3a no concurrent Tis, 2×3 cm

Patient C: a high grade tumour measuring 4.8×5.6 cm with extensive stromal and muscularis propria invasion, extending to the perivescical fat with no evidence of metastasis.

The specificity of the urine tests among those with alternative diagnoses and according to urine sample characteristics are shown in FIG. 13. Control patients with microhaematuria were more likely to have false positive tests than those without microhaematuria (p=0.002), and there was a suggestion that patients with calculi may as well, although the differences in specificity by diagnosis were not statistically significant overall (p=0.12). There were five patients with other urological cancers; only one of these gave a positive Classifier-D test result. Results from fitting logistic regression models were similar. In a logistic regression model with diagnosis and microhaematuria, the association with microhaematuria status remained significant (p=0.006) and, when compared directly to no diagnosis those with calculi had a 2.7 fold increased odds of a false positive test (95% CI (1.1 to 6.4), p=0.03). Age did not affect the specificity of the test.

Microhaematuria detected in the urine sample was the only factor clearly associated with test sensitivity. The predictive value of a positive test in this cohort was 63% for those with microhaematuria and 24% for those without, largely reflecting the greater prevalence of TCC in the patients with microhaematuria (39% vs 6%).

There were 54 patients with TCC in whom the Classifier-D test was positive. These patients were classified into severe and less severe TCC using Classifier-S. Severe TCC was defined as stage ≥1 or grade 3 at any stage. At a specificity of 90%, Classifier-S correctly classified 32/35 (91%) of the severe TCC cases.

REFERENCES

Altekruse S F, Kosary C L, Krapcho M, Neyman N, Aminou R, Waldron W, Ruhl J, Howlader N, Tatalovich Z, Cho H, Mariotto A, Eisner M P, Lewis D R, Cronin K, Chen H S, Feuer E J, Stinchcomb D G, Edwards B K (eds). *SEER Cancer Statistics Review*, 1975-2007, National Cancer Institute. Bethesda, Md., http://seer.cancer.gov/csr/1975_2007/, based on November 2009 SEER data submission, posted to the SEER web site, 2010.

Byrd, R. H., Lu, P., Nocedal, J. and Zhu, C. (1995) A limited memory algorithm for bound constrained optimization. *SIAM J. Scientific Computing*, 16, 1190-1208.

Dalgaard (2008). "Introductory Statistics with R, 2nd edition"; Peter Dalgaard, Chapter 13 (2008), Springer, ISBN 978-0-387-79053-4.

DeLong, E. R., D. M. DeLong, and D. L. Clarke-Pearson. 1988. Comparing the areas under two or more correlated receiver operating characteristic curves: A nonparametric approach. Biometrics 44: 837-845.

Gottschalk, P. G. and Dunn, J. R. (2005) The five-parameter logistic: A characterization and comparison with the four-parameter logistic. Analytic Biochemistry, 343, 54-65. Doi:10.1016/j.ab.2005.04.035

Hoerl, A. E. (1962) Application of ridge analysis to regression problems. *Chemical Engineering Progress*, 58, 54-59.

Holyoake A, O'Sullivan P, Pollock R, Best T, Watanabe J, Kajita Y, et al. Development of a multiplex RNA urine test for the detection and stratification of transitional cell carcinoma of the bladder. Clin Cancer Res. 2008 Feb. 1; 14(3):742-9.

Lunn, D., Spiegelhalter, D., Thomas, A. and Best, N. (2009) The BUGS project: Evolution, critique and future directions (with discussion), *Statistics in Medicine* 28: 3049-3082.

Moré, J. J. (1978) The Levenberg-Marquardt algorithm: implementation and theory, in Lecture Notes in Mathematics 630: Numerical Analysis, G. A. Watson (Ed.), Springer-Verlag: Berlin, pp. 105-116.

Nelder, J. A. and Mead, R. (1965) A simplex algorithm for function minimization. *Computer Journal* 7, 308-31.

(R Development Core Team (2009). R: A language and environment for statistical computing. R Foundation for Statistical Computing, Vienna, Austria. ISBN 3-900051-07-0, URL http://www.R-project.org/)

Richards, F. J. (1959) A flexible growth function for empirical use. *Journal of Experimental Botany*. 10, 290-300.

Sing et al (2009). (Tobias Sing, Oliver Sander, Niko Beerenwinkel and Thomas Lengauer (2009). ROCR: Visualizing the performance of scoring classifiers. R package version 1.0-4. http://CRAN.R-project.org/package=ROCR).

Speiss, A.-N., Feig, C. and Ritz, C. (2008) Highly accurate sigmoidal fitting of real-time RCR data by introducing a parameter for asymmetry. BMC Bioinformatics, 9, 221. Doi:10.1186/1471-2105-9-211.

Sprenger H, Lloyd A R, Lautens L L, Bonner T I, Kelvin D J. Structure, genomic organization, and expression of the human interleukin-8 receptor B gene. J Biol Chem. 1994 Apr. 15; 269(15):11065-72.

StataCorp. 2009. *Stata Statistical Software: Release* 11. College Station, Tex.: StataCorp LP.

Venables, W. N. & Ripley, B. D. (2002). Modern Applied Statistics with S. Fourth Edition. Springer, New York. ISBN 0-387-95457-0.

We claim:

1. A method for treating bladder cancer or an inflammatory condition of the bladder in a patient based on detecting genetic markers for bladder cancer and for an inflammatory condition of the bladder in said patient, comprising:
   a) providing a sample of urine from said patient;
   b) detecting the level of human neutrophil marker C-X-C Motif Chemokine Receptor 2 (CXCR2; alias interleukin 8 receptor B (IL8Rb) in said sample;
   c) detecting the amounts of the markers midkine (MDK), homeobox A13 (HOXA13), cyclin dependent kinase 1 (CDK1; alias cell division cycle protein 2 homolog (CDC2)), and insulin-like growth factor binding protein (IGFBP5) in said sample;
   d) comparing said levels of CXCR2 (IL8Rb), MDK, CDK1 (CDC2), HOXA13 and IGFBP5 in said patient's sample to the levels of CXCR2 (IL8Rb), MDK, CDK1 (CDC2), HOXA13, and IGFBP5 in samples of urine from a reference population of subjects not having bladder cancer, wherein said comparing is made by: calculating a value representing the ratio $\Delta Cp$ for expression of each marker in said patient's sample divided by the expression of each marker in samples from a population of subjects not having bladder cancer using the formula:

$\Delta C_p = \log_{10} \text{Conc}_{SAMPLE}/\text{Conc}_{REF}$, so the resulting $\Delta C_p$ estimates, one for each marker, reflect the ratios in marker expression between the patient's sample and the reference samples;
   e) if the level of CXCR2 (IL8Rb) in said patient's sample is elevated compared to the level of CXCR2 (IL8Rb) in samples of urine from said population of subjects not having bladder cancer and the urine levels of CDC2, MDK, HOXA13, and IGFBP5 are not elevated, said patient does not have bladder cancer, and has an inflammatory condition of the bladder;
   f) if the level of CXCR2 (IL8Rb) in said patient's sample of urine is not elevated compared to the levels of CXCR2 (IL8Rb) in samples from said population of subjects not having bladder cancer, and the levels of one or more of MDK, CDK1 (CDC2), HOXA13, and IGFBP5 in said patient's sample are elevated compared to levels of MDK, CDK1 (CDC2), HOXA13, and IGFBP5 in the samples of urine from said population of subjects not having bladder cancer, said subject has bladder cancer;
   g) if the patient has an inflammatory condition of the bladder in step e), said patient is treated with an anti-inflammatory agent; and
   h) if the patient has bladder cancer in step f), said patient is treated with surgery to remove the tumor.

2. The method of claim 1, wherein the level of expression of CXCR2 (IL8Rb) is detected using a polymerase chain reaction (PCR) using a forward primer having the sequence of SEQ ID NO:15.

3. The method of claim 1, wherein the level of expression of CXCR2 (IL8Rb) is detected using a polymerase chain reaction (PCR) using a reverse primer having the sequence of SEQ ID NO:16.

4. The method of claim 1, wherein the level of expression of CXCR2 (IL8Rb) is detected using a polymerase chain reaction (PCR) using a probe having the sequence of SEQ ID NO:17.

5. The method of claim 1, wherein the level of expression of MDK is detected using a polymerase chain reaction (PCR) using a forward primer having the sequence of SEQ ID NO:3.

6. The method of claim 1, wherein the level of expression of MDK is detected using a polymerase chain reaction (PCR) using a reverse primer having the sequence of SEQ ID NO:4.

7. The method of claim 1, wherein the level of expression of MDK is detected using a polymerase chain reaction (PCR) using a probe having the sequence of SEQ ID NO:5.

8. The method of claim 1, wherein the level of expression of IGFBP5 is detected using a polymerase chain reaction (PCR) using a forward primer having the sequence of SEQ ID NO:6.

9. The method of claim 1, wherein the level of expression of IGFPB5 is detected using a polymerase chain reaction (PCR) using a reverse primer having the sequence of SEQ ID NO:7.

10. The method of claim 1, wherein the level of expression of IGFBP5 is detected using polymerase chain reaction (PCR) using a probe having the sequence of SEQ ID NO:8.

11. The method of claim 1, wherein the level of expression of CDK1 (CDC2) is detected using a polymerase chain reaction (PCR) using a forward primer having the sequence of SEQ ID NO:9.

12. The method of claim 1, wherein the level of expression of CDK1 (CDC2) is detected using a polymerase chain reaction (PCR) using a reverse primer having the sequence of SEQ ID NO:10.

13. The method of claim 1, wherein the level of expression of CDK1 (CDC2) is detected using a polymerase chain reaction (PCR) using a probe having the sequence of SEQ ID NO:11.

14. The method of claim 1, wherein the level of expression of HOXA13 is detected using a polymerase chain reaction (PCR) using a forward primer having the sequence of SEQ ID NO:12.

15. The method of claim 1, wherein the level of expression of HOXA13 is detected using a polymerase chain reaction (PCR) using a reverse primer having the sequence of SEQ ID NO:13.

16. The method of claim 1, wherein the level of expression of HOXA13 is detected using a polymerase chain reaction (PCR) using a probe having the sequence of SEQ ID NO:14.

17. The method of claim 1, wherein expression of said genetic markers is carried out by detecting the amounts of mRNA in said sample.

18. The method of claim 1, wherein expression of said genetic markers is carried out by detecting the amounts of cDNA generated from mRNA in said sample.

19. The method of claim 1, wherein expression of said genetic markers is carried out by detecting the amounts of marker proteins in said sample.

* * * * *

SEQUENCE LISTING

<160> NUMBER OF SEQ ID NOS: 17

<210> SEQ ID NO 1
<211> LENGTH: 360
<212> TYPE: PRT
<213> ORGANISM: Homo sapiens

<400> SEQUENCE: 1

```
Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360
```

<210> SEQ ID NO 2
<211> LENGTH: 2880
<212> TYPE: DNA
<213> ORGANISM: Homo sapiens

<400> SEQUENCE: 2

| | | | | | |
|---|---|---|---|---|---|
| aggttcaaaa | cattcagaga | cagaaggtgg | atagacaaat | ctccaccttc agactggtag | 60 |
| gctcctccag | aagccatcag | acaggaagat | gtgaaaatcc | ccagcactca tcccagaatc | 120 |
| actaagtggc | acctgtcctg | ggccaaagtc | ccaggacaga | cctcattgtt cctctgtggg | 180 |
| aatacctccc | caggagggca | tcctggattt | ccccttgca | acccaggtca gaagtttcat | 240 |
| cgtcaaggtt | gtttcatctt | ttttttcctg | tctaacagct | ctgactacca cccaaccttg | 300 |
| aggcacagtg | aagacatcgg | tggccactcc | aataacagca | ggtcacagct gctcttctgg | 360 |
| aggtgtccta | caggtgaaaa | gcccagcgac | ccagtcagga | tttaagttta cctcaaaaat | 420 |
| ggaagatttt | aacatggaga | gtgacagctt | gaagatttc | tggaaggtg aagatcttag | 480 |
| taattacagt | tacagctcta | ccctgccccc | ttttctacta | gatgccgccc catgtgaacc | 540 |
| agaatccctg | gaaatcaaca | agtattttgt | ggtcattatc | tatgccctgg tattcctgct | 600 |
| gagcctgctg | ggaaactccc | tcgtgatgct | ggtcatctta | tacagcaggg tcggccgctc | 660 |
| cgtcactgat | gtctacctgc | tgaacctagc | cttggccgac | ctactctttg ccctgacctt | 720 |
| gcccatctgg | gccgcctcca | aggtgaatgg | ctggattttt | ggcacattcc tgtgcaaggt | 780 |
| ggtctcactc | ctgaaggaag | tcaacttcta | tagtggcatc | ctgctactgg cctgcatcag | 840 |
| tgtggaccgt | tacctggcca | ttgtccatgc | cacacgcaca | ctgacccaga gcgctactt | 900 |
| ggtcaaattc | atatgtctca | gcatctgggg | tctgtccttg | ctcctggccc tgcctgtctt | 960 |
| acttttccga | aggaccgtct | actcatccaa | tgttagccca | gcctgctatg aggacatggg | 1020 |
| caacaataca | gcaaactggc | ggatgctgtt | acggatcctg | ccccagtcct ttggcttcat | 1080 |
| cgtgccactg | ctgatcatgc | tgttctgcta | cggattcacc | ctgcgtacgc tgtttaaggc | 1140 |
| ccacatgggg | cagaagcacc | gggccatgcg | ggtcatcttt | gctgtcgtcc tcatcttcct | 1200 |
| gctctgctgg | ctgcccctaca | acctggtcct | gctggcagac | accctcatga ggacccaggt | 1260 |
| gatccaggag | acctgtgagc | gccgcaatca | catcgaccgg | gctctggatg ccaccgagat | 1320 |
| tctgggcatc | cttcacagct | gcctcaaccc | cctcatctac | gccttcattg ccagaagtt | 1380 |
| tcgccatgga | ctcctcaaga | ttctagctat | acatggcttg | atcagcaagg actccctgcc | 1440 |
| caaagacagc | aggccttcct | tgttggctc | ttcttcaggg | cacacttcca ctactctcta | 1500 |
| agacctcctg | cctaagtgca | gccccgtggg | gttcctccct | tctcttcaca gtcacattcc | 1560 |
| aagcctcatg | tccactggtt | cttcttggtc | tcagtgtcaa | tgcagccccc attgtggtca | 1620 |
| caggaagtag | aggaggccac | gttcttacta | gtttcccttg | catggtttag aaagcttgcc | 1680 |
| ctggtgcctc | accccttgcc | ataattacta | tgtcatttgc | tggagctctg cccatcctgc | 1740 |
| ccctgagccc | atggcactct | atgttctaag | aagtgaaaat | ctacactcca gtgagacagc | 1800 |
| tctgcatact | cattaggatg | gctagtatca | aagaaagaa | atcaggctg ccaacgggg | 1860 |
| tgaaaccctg | tctctactaa | aaatacaaaa | aaaaaaaaa | attagccggg cgtggtggtg | 1920 |
| agtgcctgta | atcacagcta | cttgggaggc | tgagatggga | gaatcacttg aacccgggag | 1980 |
| gcagaggttg | cagtgagccg | agattgtgcc | cctgcactcc | agcctgagcg acagtgagac | 2040 |
| tctgtctcag | tccatgaaga | tgtagaggag | aaactggaac | tctcgagcgt tgctgggggg | 2100 |
| gattgtaaaa | tggtgtgacc | actgcagaag | acagtatggc | agctttcctc aaaacttcag | 2160 |

```
acatagaatt aacacatgat cctgcaattc cacttatagg aattgaccca caagaaatga    2220
aagcagggac ttgaacccat atttgtacac caatattcat agcagcttat tcacaagacc    2280
caaaaggcag aagcaaccca atgttcatc aatgaatgaa tgaatggcta agcaaaatgt    2340
gatatgtacc taacgaagta tccttcagcc tgaaagagga atgaagtact catacatgtt    2400
acaacacgga cgaaccttga aaactttatg ctaagtgaaa taagccagac atcaacagat    2460
aaatagttta tgattccacc tacatgaggt actgagagtg aacaaattta cagagacaga    2520
aagcagaaca gtgattacca gggactgagg ggaggggagc atgggaagtg acggtttaat    2580
gggcacaggg tttatgttta ggatgttgaa aaagttctgc agataaacag tagtgatagt    2640
tgtaccgcaa tgtgacttaa tgccactaaa ttgacactta aaaatggttt aaatggtcaa    2700
ttttgttatg tatattttat atcaatttaa aaaaaaacct gagccccaaa aggtatttta    2760
atcaccaagg ctgattaaac caaggctaga accacctgcc tatattttt gttaaatgat    2820 ttcattcaat atctttttt taataaacca tttttacttg ggtgtttata aaaaaaaaaa    2880
```

<210> SEQ ID NO 3
<211> LENGTH: 18
<212> TYPE: DNA
<213> ORGANISM: Artificial sequence
<220> FEATURE:
<223> OTHER INFORMATION: Synthetic

<400> SEQUENCE: 3
tgcaccccca agaccaaa                                                    18

<210> SEQ ID NO 4
<211> LENGTH: 26
<212> TYPE: DNA
<213> ORGANISM: Artificial sequence
<220> FEATURE:
<223> OTHER INFORMATION: Synthetic

<400> SEQUENCE: 4
tgattaaagc taacgagcag acagaa                                           26

<210> SEQ ID NO 5
<211> LENGTH: 26
<212> TYPE: DNA
<213> ORGANISM: Artificial sequence
<220> FEATURE:
<223> OTHER INFORMATION: Synthetic

<400> SEQUENCE: 5
ccttcccttt cttggctttg gccttt                                           26

<210> SEQ ID NO 6
<211> LENGTH: 22
<212> TYPE: DNA
<213> ORGANISM: Artificial sequence
<220> FEATURE:
<223> OTHER INFORMATION: Synthetic

<400> SEQUENCE: 6
cgttgtacct gcccaattgt ga                                               22

<210> SEQ ID NO 7
<211> LENGTH: 20
<212> TYPE: DNA
<213> ORGANISM: Artificial sequence
<220> FEATURE:

<223> OTHER INFORMATION: Synthetic

<400> SEQUENCE: 7
gggacgcatc actcaacgtt                                               20

<210> SEQ ID NO 8
<211> LENGTH: 27
<212> TYPE: DNA
<213> ORGANISM: Artificial sequence
<220> FEATURE:
<223> OTHER INFORMATION: Synthetic

<400> SEQUENCE: 8
aagagaaagc agtgcaaacc ttcccgt                                       27

<210> SEQ ID NO 9
<211> LENGTH: 16
<212> TYPE: DNA
<213> ORGANISM: Artificial sequence
<220> FEATURE:
<223> OTHER INFORMATION: Synthetic

<400> SEQUENCE: 9
gccgccgcgg aataat                                                   16

<210> SEQ ID NO 10
<211> LENGTH: 28
<212> TYPE: DNA
<213> ORGANISM: Artificial sequence
<220> FEATURE:
<223> OTHER INFORMATION: Synthetic

<400> SEQUENCE: 10
tgtctaccct tatacacaac tccatagg                                      28

<210> SEQ ID NO 11
<211> LENGTH: 31
<212> TYPE: DNA
<213> ORGANISM: Artificial sequence
<220> FEATURE:
<223> OTHER INFORMATION: Synthetic

<400> SEQUENCE: 11
agccgggatc taccataccc attgactaac t                                  31

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
tggaacggcc aaatgtactg                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
tggcgtattc ccgttcaagt                                               20

```
<210> SEQ ID NO 14
<211> LENGTH: 23
<212> TYPE: DNA
<213> ORGANISM: Artificial sequence
<220> FEATURE:
<223> OTHER INFORMATION: Synthetic

<400> SEQUENCE: 14
actctgcccg acgtggtctc cca                                              23

<210> SEQ ID NO 15
<211> LENGTH: 23
<212> TYPE: DNA
<213> ORGANISM: Artificial sequence
<220> FEATURE:
<223> OTHER INFORMATION: Synthetic

<400> SEQUENCE: 15
ccttgaggca cagtgaagac atc                                              23

<210> SEQ ID NO 16
<211> LENGTH: 23
<212> TYPE: DNA
<213> ORGANISM: Artificial sequence
<220> FEATURE:
<223> OTHER INFORMATION: Synthetic

<400> SEQUENCE: 16
cctgtaggac acctccagaa gag                                              23

<210> SEQ ID NO 17
<211> LENGTH: 27
<212> TYPE: DNA
<213> ORGANISM: Artificial sequence
<220> FEATURE:
<223> OTHER INFORMATION: Synthetic

<400> SEQUENCE: 17
tggccactcc aataacagca ggtcaca                                          27
```